(12) United States Patent
Zhu

(10) Patent No.: US 7,498,414 B2
(45) Date of Patent: Mar. 3, 2009

(54) HUMAN ANTIBODIES SPECIFIC TO KDR AND USES THEREOF

(75) Inventor: Zhenping Zhu, Oakland, NJ (US)

(73) Assignee: ImClone Systems Incorporated, New York, NY (US)

(*) Notice: Subject to any disclaimer, the term of this patent is extended or adjusted under 35 U.S.C. 154(b) by 5 days.

(21) Appl. No.: 10/506,997

(22) PCT Filed: Mar. 4, 2003

(86) PCT No.: PCT/US03/06459

§ 371 (c)(1),
(2), (4) Date: May 23, 2005

(87) PCT Pub. No.: WO03/075840

PCT Pub. Date: Sep. 18, 2003

(65) Prior Publication Data

US 2005/0234225 A1     Oct. 20, 2005

Related U.S. Application Data

(60) Provisional application No. 60/361,783, filed on Mar. 4, 2002.

(51) Int. Cl.
  C07K 16/00   (2006.01)
(52) U.S. Cl. .................................. 530/387.1; 530/350
(58) Field of Classification Search ...................... None
See application file for complete search history.

(56) References Cited

U.S. PATENT DOCUMENTS

| | | |
|---|---|---|
| 4,683,295 A | 7/1987 | Carson |
| 4,714,680 A | 12/1987 | Civin |
| 4,965,204 A | 10/1990 | Civin |
| 5,035,994 A | 7/1991 | Civin |
| 5,061,620 A | 10/1991 | Tsukamoto et al. |
| 5,130,144 A | 7/1992 | Civin |
| 5,328,695 A | 7/1994 | Lucas et al. |
| 5,530,101 A | 6/1996 | Queen et al. |
| 5,543,503 A | 8/1996 | Chuntharapai et al. |
| 5,548,065 A | 8/1996 | Lemischka |
| 5,558,864 A | 9/1996 | Bendig et al. |
| 5,599,703 A | 2/1997 | Davis et al. |
| 5,672,499 A | 9/1997 | Anderson et al. |
| 5,674,722 A | 10/1997 | Mulligan et al. |
| 5,735,541 A | 4/1998 | Fritschi et al. |
| 5,792,395 A | 8/1998 | Ito et al. |
| 5,837,242 A | 11/1998 | Holliger et al. |
| 5,840,299 A | 11/1998 | Bendig et al. |
| 5,843,633 A | 12/1998 | Yin et al. |
| 5,851,999 A | 12/1998 | Ullrich et al. |
| 5,861,301 A | 1/1999 | Terman et al. |
| 5,981,569 A | 11/1999 | App et al. |
| 6,004,554 A | 12/1999 | Thorpe et al. |
| 6,075,181 A * | 6/2000 | Kucherlapati et al. ......... 800/25 |
| 6,204,011 B1 | 3/2001 | Kendall et al. |
| 6,245,759 B1 | 6/2001 | Bilodeau et al. |
| 6,297,238 B1 | 10/2001 | Doyle et al. |
| 6,342,219 B1 | 1/2002 | Thorpe et al. |
| 6,448,277 B2 | 9/2002 | Altmann et al. |
| 6,519,852 B1 | 2/2003 | Chen |
| 6,617,160 B1 | 9/2003 | Shitara et al. |
| 6,703,020 B1 | 3/2004 | Thorpe et al. |
| 6,844,779 B2 | 1/2005 | McEwen |
| 6,986,890 B1 | 1/2006 | Shitara et al. |
| 7,052,693 B2 | 5/2006 | Shitara et al. |
| 2001/0021382 A1 | 9/2001 | Ferrara et al. |
| 2003/0018545 A1 | 1/2003 | Yonezawa et al. |
| 2003/0191055 A1 | 10/2003 | Epstein et al. |
| 2004/0259156 A1 | 12/2004 | Zhu |

FOREIGN PATENT DOCUMENTS

WO   WO02/70008   *   3/2001

OTHER PUBLICATIONS

Brekken et al. Cancer Research. vol. 60, p. 5117-5124, Sep. 15, 2000.*
Lu, et al., "Selection of high affinity human neutralizing antibodies to VEGFR2 from a large antibody phage display library for antiangiogenesis therapy.", Int. J. Cancer, Jan. 2002, vol. 97, pp. 393-399.
Shaheen, R.M., et al.: "Inhibited Growth of Colon Cancer Carcinomatosis by Antibodies to Vascular Endothelial and Epidermal Growth Factor Receptors", British J. Cancer, London, GB, Aug. 2001, 85(4):584-589.
Marks, J.D., et al.: "By-Passing Immunization: Building High Affinity Human Antibodies by Chain Shuffling" Bio/Technol., Nature Pub. Co., N.Y., US, Jul. 1992, 10(7):779-783.
Hoogenboom, H.R., et al.: "Natural and Designer Binding Sites Made By Phage Display Technology" Immunol. Today, Elsevier Pub., Cambridge, GB, Aug. 2000, 21(8):371-378.
Jones, et al., Proc. Nat'l Acad. Sci. USA 85:3377-81 (1988).
Jones, Genetics. 85:12 (1977),
Jordan, et al., Cell 61:953-963 (1990).
Kabrun, et al., Development 124:2039-48 (1997).
Kapainen, et al., J. Exp. Med. 178-2077-88 (1993).

(Continued)

*Primary Examiner*—Larry R. Helms
*Assistant Examiner*—Meera Natarajan
(74) *Attorney, Agent, or Firm*—Lerner, David, Littenberg, Krumholz & Mentlik, LLP

(57) ABSTRACT

The invention provides an antibodies that bind to KDR with an affinity comparable to or higher than human VEGF, and that neutralizes activation of KDR. Antibodies include whole immunoglobulins, monovalent Fabs and single chain antibodies, multivalent single chain antibodies, diabodies, triabodies, and single domain antibodies. The invention further provides nucleic acids and host cells that encode and express these antibodies. The invention further provides a method of neutralizing the activation of KDR, a method of inhibiting angiogenesis in a mammal and a method of inhibiting tumor growth in a mammal.

53 Claims, 10 Drawing Sheets

OTHER PUBLICATIONS

Katoh, et al., "Cancer Research" American Association for Cancer Research 55:5687-92 (1995).
Kawamoto, et al., American Journal of Pathology. 151(6):1523-1530.
Kiessling, et al., Neoplasia 6(3):213-223 (May/Jun. 2004).
Kim, et al., Nature 36:841-844 (1993).
Kim, K.J., et al., Growth Factors 7:53-64 (1992).
Kingsmann et al., Gene. 7:141, (1979).
Klagsbrun, M. and D'Amore, P., Annual Rev. Physiol. 53:217-239 (1991).
Kobrin, et al., J. Immunology 146:2017-2020 (1991).
Kohler and Milstein Nature 256:495-497 (1975).
Lamoyi, et al., J. Immunological Methods 56:235-243 (1983).
Larrivee, et al., International Journal of Molecular Medicine 5:447-456 (2000).
Lawrence, et al., FEBS Letters 425:479-484 (1998).
Lederman, et al., Molecular Immunology 11:1171-1181 (1991).
Leff "Found at long Last, All-potent Blood Stem Cell Bodes Well for Clinical Transfusion, Therapies" Science vol. 10, (172) 1-5 (1999).
Lemischka, et al., Cell 45:917-927 (1986).
Leung, et al., Science 246:1306-1309 (1989).
Li, et al., Journal of Cellular Biochemistry Suppl (15F):251 (1991).
Li, et al., Proceedings of the National Academy fo Science 77(6):3211-3214 (1980).
Loken, et al., Blood 69:255-263 (1987).
Lou, Drug Discov. Today 6(24):1288-1294 (2001).
Low, et al., Journal of Molecular Biology 250:359-368 (1996).
MacCallum et al., Journal of Molecular Biology 262:732-745 (1996).
Maeda, et al., Hum. Antibod. Hybridomas 2:124-134 (1991).
Martin, et al., Cell 63:203-211(1990).
Masek, et al., Experimental Hematology 22:1203-1209 (1994).
Matthews, et al., Cell 65:1143-1152 (1991).
Matthews, et al., Proc. Natl. Acad. Sci. USA 88:9026-9030 (1991).
Millauer, et al., Cell 72:835-846 (1993).
Price, et al., "Role of Vascular Endothelial Growth Factor in the Stimulation of Cellular Invasion and Signaling of Breast Cancer Cells" Cell Growth and Differentiation 12:129-135 (2001).
Rafii, et al., "Rapid Communication" Blood 84(1):10-19 (1994).
Rafii, S. et al., "Vascular and Haematopoietic Stem Cells: Novel Targets for Anti-Angiogenesis Therapy" Nature 2:826-835 (2002).
Robb, et al., Bioessays 20:611-614 (1998).
Rockwell, et al., Molecular and Cellular Differentiation 3:315-335 (1995).
Rockwell, et al., Molecular and Cellular Differentiation 3:91-109 (1995).
Rohwedel, Developmental Biology 164:87-101 (1994).
Rosnet, et al., Oncogene 6:1641-1650 (1991).
Rosnet, Genomic 9:380-385 (1991).
Rudikoff, et al., Proc. Natl. Acad. Sci USA 79(6):1979-1983 (1982).
Sambrook, et al., Molecular Cloning: A Laboratory Manual, 2~, Cold Spring Harbor Laboratory Press.
Sarzani, et al., Biochem Biophys Res Comm. 186(2):706-714 (1992).
Siemeister, et al., Cancer and Metastasis Reviews 17:241-248 (1998).
Shalaby, et al., "A Requirement for FLK-1 in Primitive and Definitive Hematopoesis and Vasculogenesis" Cell 89:981-990 (1997).
Shibuya, et al., Oncogene 5:519-524 (1990).
Shweiki, et al., Nature 359: 843-845 (1992).
Skolnick, et al., Tibtech 18:34-38 (2000).
Spangrude, et al., Science 241:58-62 (1988).
Speirs, et al., British J. of Cancer 90(5/6): 899-903 (1999).
Stemple, Cell 71:973-985 (1992).
Stinchomb, et al., Nature 282:39 (1979).
Streeten, et al., Proc. Nat'l. Acad. Sci. 86:916-920 (1989).
Suda, et al., Int'l Journal of Hematology 71:99-107 (2000).
Szilvassy, et al., Blood 74:930-939 (1989).
Terman, et al., Biochem Biophys. Res.Comm. 187(3):1579 (1992).
Terman, et al., Oncogene 6:1677-1683 (1991).
Urlab and Chasm, Proc. Natl. Acad. Sci. USA 77:4216 (1980).
Vittet, et al., Blood 88(9):3421-3431 (1996).
Wade, Nicholas "Brain Stem Cell is Discovered Twice" New York Times (Jun. 15, 1996).
Waldmann, Science 252:1657-1662 (1991).
Wek et al., Proc. Nat'l Acad. Sci, USA 86:4579-4583 (1989).
Wilks, Proceedings of the National Academy of Sciences 86:1603-1607 (1989).
Williams, et al., Cell 63:163-174 (1990).

* cited by examiner

HUMAN ANTIBODIES SPECIFIC TO KDR AND USES THEREOF

CROSS-REFERENCE TO RELATED APPLICATIONS

This application is a U.S. National Phase Application of International. Application No. PCT/US03/06459, filed Mar. 4, 2003, which claims priority of U.S. Provisional Application Ser. No. 60/361,783, filed Mar. 4, 2002.

FIELD OF THE INVENTION

The present invention is directed to human antibodies that bind to KDR, that block binding of KDR to vascular endothelial growth factor receptor (VEGFR), and that neutralize activation of KDR. The antibodies are used for treating neoplastic diseases and hyperproliferative disorders and can be used alone or in combination with other VEGFR antagonists and with epidermal growth factor receptor (EGFR) antagonists.

BACKGROUND OF THE INVENTION

Angiogenesis is a highly complex process of developing new blood vessels that involves the proliferation and migration of, and tissue infiltration by capillary endothelial cells from pre-existing blood vessels, cell assembly into tubular structures, joining of newly forming tubular assemblies to closed-circuit vascular systems, and maturation of newly formed capillary vessels.

Angiogenesis is important in normal physiological processes including embryonic development, follicular growth, and wound healing, as well as in pathological conditions such as tumor growth and in non-neoplastic diseases involving abnormal neovascularization, including neovascular glaucoma (Folkman, J. and Klagsbrun, M., Science, 235:442-7 (1987). Other disease states include but are not limited to, neoplastic diseases, including but not limited to solid tumors, atherosclerosis and other inflammatory diseases such as rheumatoid arthritis, and ophthalmological conditions such as diabetic retinopathy and age-related macular degeneration. Conditions or diseases to which persistent or uncontrolled angiogenesis contribute have been termed angiogenic dependent or angiogenic associated diseases.

One means for controlling such diseases and pathological conditions comprises restricting the blood supply to those cells involved in mediating or causing the disease or condition, for example, by occluding blood vessels supplying portions of organs in which tumors are present. Such approaches require the site of the tumor to be identified and are generally limited to treatment to a single site, or a small number of sites. An additional disadvantage of direct mechanical restriction of a blood supply is that collateral blood vessels develop, often quite rapidly, restoring the blood supply to the tumor.

Other approaches have focused on the modulation of factors that are involved in the regulation of angiogenesis. While usually quiescent, vascular endothelial proliferation is highly regulated, even during angiogenesis. VEGF is a factor that has been implicated as a regulator of angiogenesis in vivo (Klagsbrun, M. and D'Amore, P., Annual Rev. Physiol., 53: 217-39 (1991)).

An endothelial-cell specific mitogen, VEGF, acts as an angiogenesis inducer by specifically promoting the proliferation of endothelial cells. It is a homodimeric glycoprotein consisting of two 23 kD subunits. Four different monomeric isoforms of VEGF resulting from alternative splicing of mRNA have been identified. These include two membrane bound forms ($VEGF_{206}$ and $VEGF_{189}$) and two soluble forms ($VEGF_{165}$ and $VEGF_{121}$). $VEGF_{165}$ is the most abundant isoform in all human tissues except placenta.

VEGF is expressed in embryonic tissues (Breier et al., Development, 114:521-32 (1992)), macrophages, and proliferating epidermal keratinocytes during wound healing (Brown et al., J. Exp. Med., 176:1375-9 (1992)), and may be responsible for tissue edema associated with inflammation (Ferrara et al., Endocr. Rev, 13:18-32 (1992)). In situ hybridization studies have demonstrated high levels of VEGF expression in a number of human tumor lines including glioblastoma multiforme, hemangioblastoma, other central nervous system neoplasms and AIDS-associated Kaposi's sarcoma (Plate, K. et al., Nature, 359:845-8 (1992); Plate, K. et al., Cancer Res., 53:5822-7 (1993); Berkman, R. et al., J. Clin. Invest., 91:153-9 (1993); Nakamura, S. et al., AIDS Weekly, 13 (1) (1992)). High levels of VEGF expression has also been found in atherosclerotic lesions, plaques and in inflammatory cells.

VEGF mediates its biological effect through high affinity VEGF receptors which are selectively expressed on endothelial cells during, for example, embryogenesis (Millauer, B. et al. Cell, 72:835-46 (1993)) and tumor formation, and which have been implicated in modulating angiogenesis and tumor growth. These receptors comprise a tyrosine kinase cytosolic domain that initiates the signaling pathway involved in cell growth.

VEGF receptors typically are class III receptor-type tyrosine kinases characterized by having several, typically 5 or 7, immunoglobulin-like loops in their amino-terminal extracellular receptor ligand-binding domains (Kaipainen et al., J. Exp. Med., 178:2077-88 (1993)). The other two regions include a transmembrane region and a carboxy-terminal intracellular catalytic domain interrupted by an insertion of hydrophilic interkinase sequences of variable lengths, called the kinase insert domain (Terman et al., Oncogene, 6:1677-83 (1991)). VEGF receptors include fms-like tyrosine kinase receptor (flt-1), or VEGFR-1, sequenced by Shibuya et al., Oncogene, 5:519-24 (1990), kinase insert domain-containing receptor/fetal liver kinase (KDR/flk-1), or VEGFR-2, described in WO 92/14248, filed Feb. 20, 1992, and Terman et al., Oncogene, 6:1677-83 (1991) and sequenced by Matthews et al., Proc. Natl. Acad. Sci. USA, 88:9026-30 (1991), although other receptors can also bind VEGF. Another tyrosine kinase receptor, VEGFR-3 (flt-4), binds the VEGF homologues VEGF-C and VEGF-D and is important in the development of lymphatic vessels.

Release of VEGF by a tumor mass stimulates angiogenesis in adjacent endothelial cells. When VEGF is expressed by the tumor mass, endothelial cells adjacent to the VEGF+ tumor cells will up-regulate expression of VEGF receptors, e.g., VEGFR-1 and VEGFR-2. It is generally believed that KDR/VEGFR-2 is the main VEGF signal transducer that results in endothelial cell proliferation, migration, differentiation, tube formation, increase of vascular permeability, and maintenance of vascular integrity. VEGFR-1 possesses a much weaker kinase activity, and is unable to generate a mitogenic response when stimulated by VEGF, although it binds to VEGF with an affinity that is approximately 10-fold higher than KDR VEGFR-1 has also been implicated in VEGF and placenta growth factor (P1GF) induced migration of monocytes and macrophages and production of tissue factor.

High levels of VEGFR-2, for example, are expressed by endothelial cells that infiltrate gliomas (Plate, K. et al. (1992)), and are specifically upregulated by VEGF produced by human glioblastomas (Plate, K. et al. (1993)). The finding of high levels of VEGR-2 expression in glioblastoma associated endothelial cells (GAEC) suggests that receptor activity is induced during tumor formation, since VEGFR-2 transcripts are barely detectable in normal brain endothelial cells, indicating generation of a paracrine VEGF/VEGFR loop. This upregulation is confined to the vascular endothelial cells in close proximity to the tumor. Blocking VEGF activity with neutralizing anti-VEGF monoclonal antibodies (mAbs) results in inhibition of the growth of human tumor xenografts in nude mice (Kim, K. et al. *Nature,* 362:841-4 (1993)), suggesting a direct role for VEGF in tumor-related angiogenesis.

Accordingly, VEGFR antagonists have been developed to treat vascularized tumors and other angiogenic diseases. These have included neutralizing antibodies that block signaling by VEGF receptors expressed on vascular endothelial cells to reduce tumor growth by blocking angiogenesis through an endothelial-dependent paracrine loop. See, e.g., U.S. Pat. No. 6,365,157 (Rockwell et al.), WO 00/44777 (Zhu et al.), WO 01/54723 (Kerbel); WO 01/74296 (Witte et al.), WO 01/90192 (Zhu), WO 03/002144 (Zhu), and WO 03/000183 (Carmeliet et al.).

VEGF receptors have also been found on some non-endothelial cells, such as tumor cells producing VEGF, wherein an endothelial-independent autocrine loop is generated to support tumor growth. For example, VEGF is almost invariably expressed by all established leukemic cell lines and freshly isolated human leukemias. Further, VEGFR-2 and VEGFR-1 are expressed by certain human leukemias. Fielder et al., *Blood* 89:1870-5 (1997); Bellamy et al., *Cancer Res.* 59728-33 (1999). It has been demonstrated that a VEGF/human VEGFR-2 autocrine loop mediates leukemic cell survival and migration in viio. Dias et al., *J. Clin. Invest.* 106:511-21 (2000); and WO01/74296 (Witte et al.). Similarly, VEGF production and VEGFR expression also have been reported for some solid tumor cell lines in vitro. (See, Sato, K. et al., *Tohoku J. Exp. Med.,* 185: 173-84 (1998); Ishii, Y., *Nippon Sanka Fujinka Gakkai Zasshi:* 47: 133-40 (1995); and Ferrer, F. A. et al, *Urology,* 54:567-72 (1999)). It has further been demonstrated that VEGFR-1 Mabs inhibit an autocrine VEGFR/human VEGFR-1 loop in breast carcinoma cells. Wu, et al., "Monoclonal antibody against VEGFR1 inhibits flt1-positive DU4475 human breast tumor growth by a dual mechanism involving anti-angiogenic and tumor cell growth inhibitory activities," AACR NCI EORTC International Conference on Molecular Targets and Cancer Therapeutics, Oct. 29-Nov. 2, 2001, Abstract #7.

There remains a need for agents0 which inhibit VEGF receptor activity to treat or prevent VEGF-receptor dependent diseases or conditions, by inhibiting, for example, pathogenic angiogenesis or tumor growth through inhibition of the paracrine and/or autocrine VEGF/VEGFR loop.

SUMMARY OF THE INVENTION

The present invention provides human antibodies, and portions thereof that bind to KDR, block binding of vascular endothelial growth factor (VEGF) to KDR, and neutralize activation of KDR. The antibodies are used for treating neoplastic diseases, including, for example, solid and non-solid tumors. The antibodies can also be used for treatment of hyperproliferative disorders. Accordingly, the invention provides methods of neutralizing the activation of KDR, methods of inhibiting tumor growth, including inhibition of tumor associated angiogenesis, and methods of treating other angiogenesis related disorders. The present invention provides kits having human antibodies or antibody fragments that bind to VEGR receptors.

The antibodies can be used alone or in combination with other VEGFR antagonists, and/or angiogenesis inhibitors such as, for example, epidermal growth factor receptor (EGFR) antagonists. The invention also provides nucleic acid molecules that encode the antibodies.

Abbreviations—VEGF, vascular endothelial growth factor; bFGF, basic fibroblast growth factor; KDR, kinase insert domain-containing receptor (also known as VEGF receptor 2); FLK-1, fetal liver kinase 1; scFv, single chain Fv; HUVEC, human umbilical vein endothelial cells; PBS, 0.01M phosphate buffered saline (pH 7.2); PBST, PBS containing 0.1% Tween-20; AP, alkaline phosphatase; EGF, epidermal growth factor; $V_H$ and $V_L$, variable domain of immunogloblin heavy and light chain, respectively.

DESCRIPTION OF THE FIGURES

FIG. 1A: BstN I digestion patterns of four neutralizing anti-KDR Fab. FIG. 1B: SDS-PAGE analysis of purified Fab fragments under nonreducing conditions. Lane 1, D1F7; Lane 2, D2C6; Lane 3, D1H4; Lane 4, D2H2.

FIG. 2A: Dose-dependent binding of human anti-KDR Fab to immobilized KDR. FIG. 2B: Inhibition of KDR binding to immobilized VEGF by anti-KDR Fab. FIG. 2C: Inhibition of Flk-1 binding to immobilized VEGF by anti-KDR Fab. Various amounts of Fab proteins were incubated with a fixed amount of KDR-AP (2B) or Flk-1-AP (2C) in solution at RT for 1 h.

FIG. 5A: VEGF promotes migration of HL60 and HEL cells in a dose dependent manner. FIG. 5B: inhibition of VEGF-stimulated migration of human leukemia cells by the anti-KDR Fab fragments. The amount of KDR-AP that bound to the immobilized VEGF was quantified by incubation of the plates with AP substrate and reading of A405 nm.

FIG. 6A: Dose-dependent binding of anti-KDR to immobilized KDR. Various amounts of antibodies were incubated at RT for 1 h in 96-well plates coated with KDR FIG. 6B: Inhibition of binding of KDR to immobilized VEGF by human anti-KDR antibodies. Various amounts of the antibodies were incubated with a fixed amount of KDR-AP in solution at RT for 1 hr.

FIG. 7A: Inhibition of binding of radiolabeled VEGF to cell-surface KDR by human anti-KDR antibodies. Various amounts of anti-KDR antibodies were mixed with 2 ng of $^{125}$I labeled VEGF$_{165}$ and added to a 80-90% confluent monolayer of HUVEC cells. The cells were incubated at RT for 2 h, washed and bound radioactivity was determined. FIG. 7B: Inhibition of VEGF-induced HUVEC mitogenesis by human anti-KDR antibodies. Various amounts of human anti-KDR antibodies were incubated with HUVEC cells for 1 h, followed by addition of VEGF. Cells were harvested and DNA incorporated radioactivity was determined.

FIG. 8A: selected mRNA levels were determined by RT-PCR. Lane 1: molecular weight markers; 1000, 850, 650, 500, 400 bp; Lane 2: negative control; Lane 3: HL60 cells (promyelocytic); Lane 4: HEL cells (megakaryocytic); Lane 5: U937 cells (hisitocytic); Lane 6: HUVEC. FIG. 8B: Secretion of VEGF by human leukemia cells cultured with 10% FCS or in serum-free media.

FIG. 9A: HL60 cells. FIG. 9B: HEL cells. FIG. 9C: U937 cells.

DETAILED DESCRIPTION OF THE INVENTION

Figure 1:
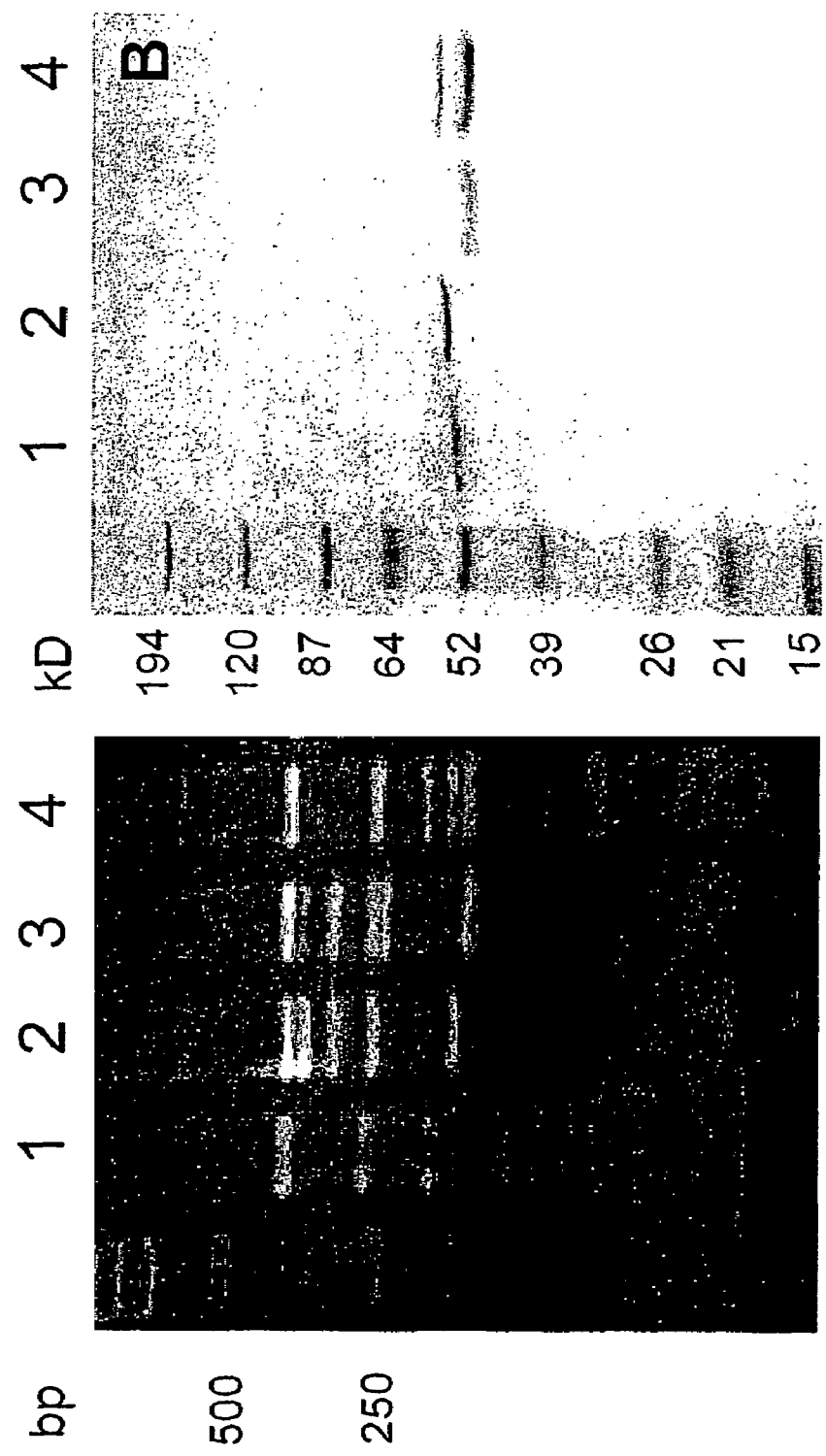
FIG. 1 shows the identification and expression of human anti-DKR Fab fragments.

The present invention provides antibodies that bind specifically to an extracellular domain of VEGFR-2 (KDR). The antibodies comprise human $V_H$ and $V_L$ framework regions (FWs) as well as human complementary determining regions (CDRs). Preferably, the entire $V_H$ and $V_L$ variable domains are human or derived from human sequences. For example, a variable domain of the invention may be obtained from a peripheral blood lymphocyte that contains a rearranged variable region gene. Alternatively, variable domain portions, such as CDR and FW regions, may be derived from different human sequences. In another example, a human $V_H$ variable domain is encoded by a human $V_H$ gene segment and a synthetic sequence for the CDR3H region (i.e., a synthetic $D_H$-$J_H$ gene segment. Likewise, a human $V_L$ variable domain may be encoded by a human $V_L$ gene segment and a synthetic sequence for the CDR3L region (i.e., a synthetic $J_L$ gene segment).

Antibodies of the present invention also include those for which binding characteristics have been improved by direct mutation, methods of affinity maturation, phage display, or chain shuffling. Affinity and specificity may be modified or improved by mutating CDRs and screening for antigen binding sites having the desired characteristics (see, e.g., Yang et al., *J. Mol. Biol.*, 254: 392-403 (1995)). CDRs are mutated in a variety of ways. One way is to randomize individual residues or combinations of residues so that in a population of otherwise identical antigen binding sites, all twenty amino acids are found at particular positions. Alternatively, mutations are induced over a range of CDR residues by error prone PCR methods (see, e.g., Hawkins et al., *J. Mol. Biol.*, 226: 889-896 (1992)). For example, phage display vectors containing heavy and light chain variable region genes may be propagated in mutator strains of *E. coli* (see, e.g., Low et al., *J. Mol. Biol.*, 250: 359-368 (1996)). These methods of mutagenesis are illustrative of the many methods known to one of skill in the art.

The antibodies bind to KDR and neutralize activation, for example, by blocking receptor dimerization and/or VEGF binding. Antibodies of the invention can be used to neutralize VEGFR activation in vitro or in vivo by binding to an extracellular domain of a VEGF receptor. Extracellular domains of a VEGF receptor include, for example, a ligand-binding domain on an extracellular portion of the receptor. In vivo, the antibodies inhibit angiogenesis, and/or reduce tumor growth.

Antibodies are proteins that recognize and bind to a specific antigen or substance. The antibodies of the present invention bind KDR at least as strongly as the natural ligand. Affinity, represented by the equilibrium constant for the dissociation of an antigen with an antibody (Kd), measures the binding strength between an antigenic determinant and an antibody binding site. Avidity is the measure of the strength of binding between an antibody with its antigen. Avidity is related to both the affinity between an epitope with its antigen binding site on the antibody, and the valence of the antibody. Valency refers to the number of antigen binding sites which an immunoglobulin has for a particular epitope. For example, a monovalent antibody has one binding site for a particular epitope. An antigenic determinant, or epitope, is the site on an antigen at which a given antibody binds. Typical values of K are $10^5$ to $10^{11}$ liters/mol. Any K less than $10^4$ liters/mol is considered to indicate binding which is nonspecific. The reciprocal of K is designated as $K_d$. ($K_d$ also may be referred to as the dissociation constant.) The lesser the value of the $K_d$, the stronger the binding strength between an antigenic determinant and the antibody binding site.

The natural ligand of KDR is human VEGF. VEGF binds KDR with an affinity ($K_d$) of about 0.93 nM. In order to hinder the binding of VEGF with KDR, an anti-KDR antibody should bind KDR at lease as strongly as VEGF. In other words, the anti-KDR antibody needs to successfully compete with VEGF with respect to binding KDR. An antibody with a $K_d$ of at most 5 nM is considered to bind as strongly as the natural ligand. The antibodies of the invention preferably bind KDR with an affinity of at most about 4 nM, more preferably with an affinity of at most about 3 nM, most preferably with an affinity of at most about 2 nM, and optimally with an affinity of at most about 1 nM. The avidity of bivalent antibodies will, of course, be greater than the affinity. Bivalent antibodies preferably bind KDR with an avidity greater than 0.5 nM, more preferably greater than 0.25 nM, and optimally greater than 0.1 nM.

The antibodies of the invention neutralize KDR. (See Examples.) In this specification, neutralizing a receptor means diminishing and/or inactivating the intrinsic kinase activity of the receptor to transduce a signal. A reliable assay for KDR neutralization is the inhibition of receptor phosphorylation.

The present invention is not limited by any particular mechanism of KDR neutralization. The mechanism followed by one antibody is not necessarily the same as that followed by another. Some possible mechanisms include preventing binding of the VEGF ligand to the extracellular binding domain of the KDR, and preventing dimerization or oligomerization of receptors. Other mechanisms cannot, however, be ruled out.

Antibodies of the invention include, but are not limited to, naturally occuring antibodies, bivalent fragments such as (Fab')$_2$, monovalent fragments such as Fab, single chain antibodies, single chain Fv (scFv), single domain antibodies, multivalent single chain antibodies, diabodies, triabodies, and the like that bind specifically with antigens.

Monovalent single chain antibodies (i.e., scFv) include an antibody variable heavy-chain fragment ($V_H$) linked to an antibody variable light-chain fragment ($V_L$) by a peptide linker which allows the two fragments to associate to form a functional antigen binding site (see, for example U.S. Pat. No.

4,946,778 (Ladner et al.), WO 88/09344, (Huston et al.). WO 92/01047 (McCafferty et al.) describes the display of scFv fragments on the surface of soluble recombinant genetic display packages, such as bacteriophage. A single chain antibody with a linker (L) can be represented as $V_L$-L-$V_H$ or $V_H$-L-$V_L$.

Each domain of the antibodies of this invention may be a complete antibody heavy or light chain variable domain, or it may be a functional equivalent or a mutant or derivative of a naturally occuring domain, or a synthetic domain constructed, for example, in vitro using a technique such as one described in WO 93/11236 (Griffiths et al.). For instance, it is possible to join together domains corresponding to antibody variable domains which are missing at least one amino acid. The important characterizing feature is the ability of each domain to associate with a complementary domain to form an antigen binding site. Accordingly, the terms "variable heavy/light chain fragment" should not be construed to exclude variants which do not have a material effect on how the invention works.

Functional equivalents of the invention include polypeptides with amino acid sequences substantially the same as the amino acid sequence of the variable or hypervariable regions of the full length KDR antibodies. "Substantially the same" amino acid sequence is defined herein as a sequence with at least 70%, preferably at least about 80%, and more preferably at least about 90% homology to another amino acid sequence, as determined by the FASTA search method in accordance with Pearson and Lipman, *Proc. Natl. Acad. Sci. USA* 85,2444-8 (1988).

Single domain antibodies have a single variable domain that is capable of efficiently binding antigen. Examples of antibodies wherein binding affinity and specificity are contributed primarilyby one or the other variable domain are known in the art. See, e.g., Jeffrey, P. D. et al., *Proc. Nat. Acad. Sci. USA* 90:10310-4 (1993), which discloses an anti-digoxin antibody which binds to digoxin primarily by the antibody heavy chain. Accordingly, single antibody domains can be identified that bind well to VEGF receptors. Such antibody domains can be obtained, for example, from naturally occurring antibodies, or Fab or scFv phage display libraries. It is understood that, to make a single domain antibody from an antibody comprising a $V_H$ and a $V_L$ domain, certain amino acid substitutions outside the CDR regions may be desired to enhance binding, expression or solubility. For example, it may be desirable to modify amino acid residues that would otherwise be buried in the $V_H$-$V_L$ interface.

More recently, antibodies that are homodimers of heavy chains have been discovered in camelids (camels, dromedaries and llamas). These heavy chain antibodies are devoid of light chains and the first constant domain. (See, e.g., Muyldermans, S., 2001, J. Biotechnol. 74:277-302) The reduced-size antigen binding fragments are well expressed in bacteria, bind to antigen with high affinity, and are very stable. Phage display libraries of single domain antibodies (i.e., having a single variable domain that can be a light chain or a heavy chain variable domain) can be produced and screened in the same manner as scFv and Fab libraries. Scaffolds for such single domain antibodies can be modified mouse or human variable domains. It is noted that single antibody domains can bind antigen in a variety of antigen binding modes. That is, the primary antibody-antigen interactions are not limited to amino acid residues corresponding to CDRs of $V_H$-$V_L$ containing antibodies, and consideration can be given to binding interactions outside of CDR residues when optimizing the binding characteristics of such antibodies.

Single chain antibodies lack some or all of the constant domains of the whole antibodies from which they are derived. Therefore, they may overcome some of the problems associated with the use of whole antibodies. For example, single-chain antibodies tend to be free of certain undesired interactions between heavy-chain constant regions and other biological molecules. Additionally, single-chain antibodies are considerably smaller than whole antibodies and may have greater permeability than whole antibodies, allowing single-chain antibodies to localize and bind to target antigen-binding sites more efficiently. Also, single chain antibodies can be produced on a relatively large scale in prokaryotic cells, thus facilitating their production. Furthermore, the relatively small size of single-chain antibodies makes them less likely to provoke an unwanted immune response in a recipient than whole antibodies.

The peptide linkers used to produce the single chain antibodies may be flexible peptides selected to assure that the proper three-dimensional folding of the $V_L$ and $V_H$ domains may occur once they are linked so as to maintain the target molecule binding-specificity of the full length anti-KDR antibody. Generally, the carboxyl terminus of the $V_L$ or $V_H$ sequence may be covalently linked by such a peptide linker to the amino acid terminus of a complementary $V_H$ or $V_L$ sequence. The linker is generally 10 to 50 amino acid residues. Preferably, the linker is 10 to 30 amino acid residues. More preferably the linker is 12 to 30 amino acid residues. Most preferably is a linker of 15 to 25 amino acid residues. An example of such linker peptides include (Gly-Gly-Gly-Gly-Ser)$_3$.

Single chain antibodies, each having one $V_H$ and one $V_L$ domain covalently linked by a first peptide linker, can be covalently linked by at least one more peptide linker to form a multivalent single chain antibody. Multivalent single chain antibodies allow for the construction of antibody fragments which have the specificity and avidity of whole antibodies, but lack the constant regions of the full length antibodies.

Multivalent antibodies may be monospecific or multispecific. The term specificity refers to the number of different types of antigenic determinants to which a particular antibody can bind. If the antibody binds to only one type of antigenic determinant, the antibody is monospecific. If the antibody binds to different types of antigenic determinants then the antibody is multispecific.

For example, a bispecific multivalent single chain antibody allows for the recognition of two different types of epitopes. The epitopes may both be on KDR. Alternatively, one epitope may be on KDR, and the other epitope may be on another antigen.

Each chain of a multivalent single chain antibody includes a variable light-chain fragment and a variable heavy-chain fragment, and is linked by a peptide linker to at least one other chain. The peptide linker is composed of at least fifteen amino acid residues. The maximum number of amino acid residues is about one hundred. In a preferred embodiment, the number of $V_L$ and $V_H$ domains is equivalent. Preferably, the peptide linker ($L_1$) joining the $V_H$ and $V_L$ domains to form a chain and the peptide linker ($L_2$) joining two or more chains to form a multivalent scFv have substantially the same amino acid sequence.

For example, a bivalent single chain antibody can be represented as follows: $V_L$-$L_1$-$V_H$-$L_2$-$V_L$-$L_1$-$V_H$; or $V_L$-$L_1$-$V_H$-$L_2$-$V_H$-$L_1$-$V_H$; or $V_H$-$L_1$-$V_L$-$L_2$-$V_H$-$L_1$-$V_L$; or $V_H$-$L_1$-$V_L$-$L_2$-$V_L$-$L_1$-$V_H$.

Multivalent single chain antibodies which are trivalent or greater have one or more antibody fragments joined to a bivalent single chain antibody by additional peptide linkers. One example of a trivalent single chain antibody is:

$V_L\text{-}L_1\text{-}V_H\text{-}L_2\text{-}V_L\text{-}L_1\text{-}V_H\text{-}L_2\text{-}V_L\text{-}L_1\text{-}V_H$.

Two single chain antibodies can be combined to form a diabody, also known as a bivalent dimer. Diabodies have two chains and two binding sites, and may be monospecific or bispecific. Each chain of the diabody includes a $V_H$ domain connected to a $V_L$ domain. The domains are connected with linkers that are short enough to prevent pairing between domains on the same chain, thus driving the pairing between complementary domains on different chains to recreate the two antigen-binding sites. Accordingly, one chain of a bispecific diabody comprises $V_H$ of a first specificity and $V_L$ of a second specificity, whereas the second chain comprises $V_H$ of the second specificity and $V_L$ of the first specificity. The peptide linker includes at least five amino acid residues and no more than ten amino acid residues, e.g. (Gly-Gly-Gly-Gly-Ser), (Gly-Gly-Gly-Gly-Ser)$_2$. (SEQ ID NO:19.) The diabody structure is rigid and compact. The antigen-binding sites are at opposite ends of the molecule.

Three single chain antibodies can be combined to form triabodies, also known as trivalent trimers. Triabodies are constructed with the amino acid terminus of a $V_L$ or $V_H$ domain directly fused to the carboxyl terminus of a $V_L$ or $V_H$ domain, i.e., without any linker sequence. The triabody has three Fv heads with the polypeptides arranged in a cyclic, head-to-tail fashion. A possible conformation of the triabody is planar with the three binding sites located in a plane at an angle of 120 degrees from one another. Triabodies may be monospecific, bispecific or trispecific.

Preferably the antibodies of this invention contain all six complementarity determining regions of the whole antibody, although antibodies containing fewer than all of such regions, such as three, four or five CDRs, are also functional.

To minimize the immunogenicity of antibodies that bind to VEGF receptors, the present invention provides antibodies which comprise human variable and constant domain sequences. The antibodies are derived from a human source and bind to an extacellular domain of KDR and neutralize activation of the receptor. DNA encoding human antibodies may be prepared by recombining DNA encoding human constant regions and DNA encoding variable regions derived from humans. For example, antibodies of the invention can be obtained by screening libraries consisting of combinations of human light chain and heavy chain variable domains. The nucleic acids from which the antibodies are expressed can be somatically mutated, or be germiline sequences derived from naive B cells.

DNA encoding human antibodies may be prepared by recombining DNA encoding human constant regions and variable regions, other than the CDRs, derived substantially or exclusively from the corresponding human antibody regions and DNA encoding CDRs derived from a human.

Suitable sources of DNAs that encode fragments of antibodies include any cell, such as hybridomas and spleen cells, that express the full length antibody. Another source is single chain antibodies produced from a phage display library as is known in the art.

The antibodies of this invention may be or may combine members of any immunoglobulin class, such as IgG, IgM, IgA, IgD, or IgE, and the subclasses thereof.

The protein used to identify VEFGR binding antibodies of the invention is usually KDR, and is normally limited to the extracellular domain of KDR. The KDR extracellular domain may be free or conjugated to another molecule.

In the examples below high affinity anti-KDR antibodies, which block VEGF binding to KDR, were isolated from a phage display library constructed from human heavy chain and light chain variable region genes. Over 90% of recovered clones after three rounds of selection are specific to KDR. The binding affinities for KDR of the screened Fabs are in the nM range, which are as high as those of several bivalent anti-KDR monoclonal antibodies produced using hybridoma technology.

The antibodies of this invention may be fused to additional amino acid residues. Such residues may be a peptide tag, perhaps to facilitate isolation, or they may be a signal sequence for secretion of the polypeptide from a host cell upon synthesis. Suitably, secretory leader peptides are used, being amino acids joined to the N-terminal end of a polypeptide to direct movement of the polypeptide out of the cytosol.

The present invention also provides nucleic acids which comprise a sequence encoding a polypeptide according to the invention, and diverse repertoires of such nucleic acid.

Antibodies of the invention neutralize activation of KDR. One measure of KDR neutralization is inhibition of the tyrosine kinase activity of the receptor. Tyrosine kinase inhibition can be determined using well-known methods. The antibodies of the present invention generally cause inhibition or regulation of phosphorylation events. Accordingly, phosphorylation assays are useful in determining antibodies useful in the context of the present invention. Tyrosine kinase inhibition may be determined by measuring the autophosphorylation level of recombinant kinase receptor, and/or phosphorylation of natural or synthetic substrates. Phosphorylation can be detected, for example, using an antibody specific for phosphotyrosine in an ELISA assay or on a western blot. Some assays for tyrosine kinase activity are described in Panek et al., *J. Pharmacol. Exp. Thera.*, 283: 1433-44 (1997) and Batley et al., *Life Sci.*, 62: 143-50 (1998).

In addition, methods for detection of protein expression can be utilized, wherein the proteins being measured are regulated by KDR tyrosine kinase activity. These methods include immunohistochemistry (IHC) for detection of protein expression, fluorescence in situ hybridization (FISH) for detection of gene amplification, competitive radioligand binding assays, solid matrix blotting techniques, such as Northern and Southern blots, reverse transcriptase polymerase chain reaction (RT-PCR) and ELISA. See, e.g., Grandis et al., *Cancer*, 78:1284-92. (1996); Shimizu et al., *Japan J. Cancer Res.*, 85:567-71 (1994); Sauter et al., *Am. J. Path.*, 148:1047-53 (1996); Collins, Glia, 15:289-96 (1995); Radinsky et al., *Clin. Cancer Res.*, 1:19-31 (1995); Petrides et al., *Cancer Res.*, 50:3934-39 (1990); Hoffmann et al., *Anticancer Res.*, 17:4419-26 (1997); Wikstrand et al., *Cancer Res.*, 55:3140-48 (1995).

In vivo assays can also be utilized. For example, receptor tyrosine kinase inhibition can be observed by mitogenic assays using cell lines stimulated with receptor ligand in the presence and absence of inhibitor. For example, HUVEC cells (ATCC) stimulated with VEGF can be used to assay VEGFR inhibition. Another method involves testing for inhibition of growth of VEGF-expressing tumor cells, using for example, human tumor cells injected into a mouse. See, U.S. Pat. No. 6,365,157 (Rockwell et al.).

In the methods of the present invention, a therapeutically effective amount of an antibody of the invention is administered to a mammal in need thereof. The term "administering" as used herein means delivering the antibodies of the present invention to a mammal by any method that may achieve the result sought. They may be administered, for example, intravenously or intramuscularly. Although human antibodies of the invention are particularly useful for administration to humans, they may be administered to other mammals as well.

The term "mammal" as used herein is intended to include, but is not limited to, humans, laboratory animals, domestic pets and farm animals. "Therapeutically effective amount" means an amount of antibody of the present invention that, when administered to a mammal, is effective in producing the desired therapeutic effect, such as inhibiting kinase activity.

While not intended to be bound to any particular mechanism, the diseases and conditions which may be treated or prevented by the present methods include, for example, those in which pathogenic angiogenesis or tumor growth is stimulated through a VEGFR paracrine and/or autocrine loop.

Neutralization of activation of a VEGF receptor in endothelial or non-endothelial cells, such as tumor cells, may be performed in vitro or in vivo. Neutralizing VEGF activation of a VEGF receptor in a sample of VEGF-receptor expressing cells comprises contacting the cells with an antagonist, e.g., an antibody, of the invention. The cells are contacted in vitro with the antagonist, e.g., the antibody, before, simultaneously with, or after, adding VEGF to the cell sample.

In vivo, an antibody of the invention is contacted with a VEGF receptor by administration to a mammal, preferably a human. An in vivo neutralization method is useful for inhibiting tumor growth, angiogenesis associated with tumor growth, or other pathologic condition associated with angiogenesis, in a mammal. Accordingly, the antibodies of the invention are anti-angiogenic and anti-tumor immunotherapeutic agents.

Tumors which may be treated include primary tumors and metastatic tumors, as well as refractory tumors. Refractory tumors include tumors that fail to respond or are resistant to treatment with chemotherapeutic agents alone, antibodies alone, radiation alone or combinations thereof. Refractory tumors also encompass tumors that appear to be inhibited by treatment with such agents, but recur up to five years, sometimes up to ten years or longer after treatment is discontinued.

Antibodies of the present invention are useful for treating tumors that express VEGF receptors, especially KDR. Such tumors are characteristically sensitive to VEGF present in their environment, and may further produce and be stimulated by VEGF in an autocrine stimulatory loop. The method is therefore effective for treating a solid or non-solid tumor that is not vascularized, or is not yet substantially vascularized. Examples of solid tumors which may be accordingly treated include breast carcinoma, lung carcinoma, colorectal carcinoma, pancreatic carcinoma, glioma and lymphoma. Some examples of such tumors include epidermoid tumors, squamous tumors, such as head and neck tumors, colorectal tumors, prostate tumors, breast tumors, lung tumors, including small cell and non-small cell lung tumors, pancreatic tumors, thyroid tumors, ovarian tumors, and liver tumors. Other examples include Kaposi's sarcoma, CNS neoplasms, neuroblastomas, capillary hemangioblastomas, meningiomas and cerebral metastases, melanoma, gastrointestinal and renal carcinomas and sarcomas, rhabdomyosarcoma, glioblastoma, preferably glioblastoma multiforme, and leiomyosarcoma. Examples of vascularized skin cancers for which the antagonists of this invention are effective include squamous cell carcinoma, basal cell carcinoma and skin cancers that can be treated by suppressing the growth of malignant keratinocytes, such as human malignant keratinocytes.

Examples of non-solid tumors include leukemia, multiple myeloma and lymphoma. Some examples of leukemias include acute myelogenous leukemia (AML), chronic myelogenous leukemia (CML), acute lymphocytic leukemia (ALL), chronic lymphocytic leukemia (CLL), erythrocytic leukemia or monocytic leukemia. Some examples of lymphomas include Hodgkin's and non-Hodgkin's lymphoma.

Experimental results described below demonstrate that antibodies of the invention specifically block VEGF induced stimulation of KDR (VEGFR-2) in leukemia cells. In vivo studies also described below show that the antibodies were able to significantly inhibit tumor growth in nude mice.

A cocktail of VEGF receptor antagonists, e.g., monoclonal antibodies, provides an especially efficient treatment for inhibiting the growth of tumor cells. The cocktail may include non-antibody VEGFR antagonists and may have as few as 2, 3 or 4 receptor antagonists, and as many as 6, 8 or 10.

In another aspect of the invention, anti-KDR antibodies are used to inhibit angiogenesis. VEGFR stimulation of vascular endothelium is associated with angiogenic diseases and vascularization of tumors. Typically, vascular endothelium is stimulated in a paracrine fashion by VEGF from other sources (e.g., tumor cells).

Accordingly, the human anti-KDR antibodies are effective for treating subjects with vascularized tumors or neoplasms or angiogenic diseases. Such tumors and neoplasms include, for example, malignant tumors and neoplasms, such as blastomas, carcinomas or sarcomas, and highly vascular tumors and neoplasms. Cancers that may be treated by the methods of the present invention include, for example, cancers of the brain, genitourinary tract, lymphatic system, stomach, renal, colon, larynx and lung and bone. Non-limiting examples further include epidernoid tumors, squamous tumors, such as head and neck tumors, colorectal tumors, prostate tumors, breast tumors, lung tumors, including lung adenocarcinoma and small cell and non-small cell lung tumors, pancreatic tumors, thyroid tumors, ovarian tumors, and liver tumors. The method is also used for treatment of vascularized skin cancers, including squamous cell carcinoma, basal cell carcinoma, and skin cancers that can be treated by suppressing the growth of malignant keratinocytes, such as human malignant keratinocytes. Other cancers that can be treated include Kaposi's sarcoma, CNS neoplasms (neuroblastomas, capillary hemangioblastomas, meningiomas and cerebral metastases), melanoma, gastrointestinal and renal carcinomas and sarcomas, rhabdomyosarcoma, glioblastoma, including glioblastoma multiforme, and leiomyosarcoma.

A further aspect of the present invention includes methods of treating or preventing pathologic conditions characterized by excessive angiogenesis, involving, for example, vascularization and/or inflammation, such as atherosclerosis, rheumatoid arthritis (RA), neovascular glaucoma, proliferative retinopathy including proliferative diabetic retinopathy, macular degeneration, hemangiomas, angiofibromas, and psoriasis. Other non-limiting examples of non-neoplastic angiogenic disease are retinopathy of prematurity (retrolental fibroplastic), corneal graft rejection, insulin-dependent diabetes mellitus, multiple sclerosis, myasthenia gravis, Chron's disease, autoimmune nephritis, primary biliary cirrhosis, acute pancreatitis, allograph rejection, allergic inflammation, contact dermatitis and delayed hypersensitivity reactions, inflammatory bowel disease, septic shock, osteoporosis, osteoarthritis, cognition defects induced by neuronal inflammation, Osler-Weber syndrome, restinosis, and fungal, parasitic and viral infections, including cytomegaloviral infections.

The identification of such disease is well within the ability and knowledge of one skilled in the art. For example, human individuals who are either suffering from a clinically significant neoplastic or angiogenic disease or who are at risk of developing clinically significant symptoms are suitable for administration of the present VEGF receptor antibodies. A clinician skilled in the art can readily determine, for example, by the use of clinical tests, physical examination and medical/family history, if an individual is a candidate for such treatment.

Moreover, included within the scope of the present invention is use of the present antibodies in vivo and in vitro for investigative or diagnostic methods, which are well known in the art.

The present anti-KDR antibodies can be administered for therapeutic treatments to a patient suffering from a tumor or angiogenesis associated pathologic condition in an amount sufficient to prevent, inhibit, or reduce the progression of the tumor or pathologic condition. Progression includes, e.g, the growth, invasiveness, metastases and/or recurrence of the tumor or pathologic condition. An amount adequate to accomplish this is defined as a therapeutically effective dose. Amounts effective for this use will depend upon the severity of the disease and the general state of the patient's own immune system. Dosing schedules will also vary with the disease state and status of the patient, and will typically range from a single bolus dosage or continuous infusion to multiple administrations per day (e.g., every 4-6 hours), or as indicated by the treating physician and the patient's condition. It should be noted, however, that the present invention is not limited to any particular dose.

In an embodiment of the invention, anti-KDR antibodies can be administered in combination with one or more other antineoplastic agents. For examples of combination therapies, see, e.g., U.S. Pat. No. 6,217,866 (Schlessinger et al.) (Anti-EGFR antibodies in combination with antineoplastic agents); WO 99/60023 (Waksal et al.) (Anti-EGFR antibodies in combination with radiation). Any suitable antineoplastic agent can be used, such as a chemotherapeutic agent or radiation. Examples of chemotherapeutic agents include, but are not limited to, cisplatin, doxorubicin, paclitaxel, irinotecan (CPT-11), topotecan or a combination thereof. When the antineoplastic agent is radiation, the source of the radiation can be either external (external beam radiation therapy—EBRT) or internal (brachytherapy—BT) to the patient being treated. The dose of antineoplastic agent administered depends on numerous factors, including, for example, the type of agent, the type and severity tumor being treated and the route of administration of the agent. It should be emphasized, however, that the present invention is not limited to any particular dose.

Further, anti-KDR antibodies of the invention may be administered with antibodies that neutralize other receptors involved in tumor growth or angiogenesis. One example of such a receptor is the VEGFR-1/Flt-1 receptor. In an embodiment of the invention, an anti-KDR antibody is used in combination with a receptor antagonist that binds specifically to VEGFR-1. Particularly preferred are antigen-binding proteins that bind to the extracellular domain of VEGFR-1 and block binding by one or both of its ligands, VEGF and P1GF, and/or neutralize VEGF-induced or P1GF-induced activation of VEGFR-1. For example, mAb 6.12 is a scFv that binds to soluble and cell surface-expressed VEGFR-1. ScFv 6.12 comprises the $V_L$ and $V_H$ domains of mouse monoclonal antibody mAb 6.12. A hybridoma cell line producing mAb 6.12 has been deposited as ATCC number PTA-3344 under the provisions of the Budapest Treaty on the International Recognition of the Deposit of Microorganisms for the Purposes of Patent Procedure and the regulations thereunder (Budapest Treaty).

Another example of such a receptor is EGFR. In an embodiment of the present invention, an anti-KDR antibody is used in combination with an EGFR antagonist. An EGFR antagonist can be an antibody that binds to EGFR or a ligand of EGFR and inhibits binding of EGFR to its ligand. Ligands for EGFR include, for example, EGF, TGF-α amphiregulin, heparin-binding EGF (HB-EGF) and betarecullulin. EGF and TGF-α are thought to be the main endogenous ligands that result in EGFR-mediated stimulation, although TGF-α has been shown to be more potent in promoting angiogenesis. It should be appreciated that the EGFR antagonist can bind externally to the extracellular portion of EGFR, which may or may not inhibit binding of the ligand, or internally to the tyrosine kinase domain. Examples of EGFR antagonists that bind EGFR include, without limitation, biological molecules, such as antibodies (and functional equivalents thereof) specific for EGFR, and small molecules, such as synthetic kinase inhibitors that act directly on the cytoplasmic domain of EGFR.

Other examples of growth factor receptors involved in tumorigenesis are the receptors for platelet-derived growth factor (PDGFR), insulin-like growth factor (IGFR), nerve growth factor (NGFR), and fibroblast growth factor (FGFR).

In an additional alternative embodiment, the VEGFR antagonist can be administered in combination with one or more suitable adjuvants, such as, for example, cytokines (IL-10 and IL-13, for example) or other immune stimulators. See, e.g., Larrivée et al., supra. It should be appreciated, however, that administration of only an anti-KDR antibody is sufficient to prevent, inhibit, or reduce the progression of the tumor in a therapeutically effective manner.

In a combination therapy, the anti-KDR antibody is administered before, during, or after commencing therapy with another agent, as well as any combination thereof, i.e., before and during, before and after, during and after, or before, during and after commencing the antineoplastic agent therapy. For example, the anti-KDR antibody may be administered between 1 and 30 days, preferably 3 and 20 days, more preferably between 5 and 12 days before commencing radiation therapy.

In the present invention, any suitable method or route can be used to administer anti-KDR antibodies of the invention, and optionally, to coadminister antineoplastic agents and/or antagonists of other receptors. Routes of administration include, for example, oral, intravenous, intraperitoneal, subcutaneous, or intramuscular administration. The dose of antagonist administered depends on numerous factors, including, for example, the type of antagonists, the type and severity tumor being treated and the route of administration of the antagonists. It should be emphasized, however, that the present invention is not limited to any particular method or route of administration.

It is noted that an anti-KDR antibody of the invention can be administered as a conjugate, which binds specifically to the receptor and delivers a toxic, lethal payload following ligand-toxin internalization.

It is understood that the anti-KDR antibodies of the invention, where used in a mammal for the purpose of prophylaxis or treatment, will be administered in the form of a composition additionally comprising a pharmaceutically acceptable carrier. Suitable pharmaceutically acceptable carriers include, for example, one or more of water, saline, phosphate buffered saline, dextrose, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of the binding proteins. The compositions of the injection may, as is well known in the art, be formulated so as to provide quick, sustained or delayed release of the active ingredient after administration to the mammal.

The present invention also includes kits for inhibiting tumor growth and/or angiogenesis comprising a therapeutically effective amount of a human anti-KDR antibody. The kits can further contain any suitable antagonist of, for example, another growth factor receptor involved in tumorigenesis or angiogenesis (e.g., VEGFR-1/Flt-1, EGFR, PDGFR, IGFR, NGFR, FGFR, etc, as described above). Alternatively, or in addition, the kits of the present invention can further comprise an antineoplastic agent. Examples of suitable antineoplastic agents in the context of the present invention have been described herein. The kits of the present invention can further comprise an adjuvant, examples have also been described above.

In another aspect of the invention, an anti-KDR antibody of the invention can be chemically or biosynthetically linked to one or more antineoplastic or antiangiogenic agents.

The invention further contemplates anti-KDR antibodies to which target or reporter moieties are linked. Target moieties are first members of binding pairs. Antineoplastic agents, for example, are conjugated to second members of such pairs and are thereby directed to the site where the anti-KDR antibody is bound. A common example of such a binding pair is adivin and biotin. In a preferred embodiment, biotin is conjugated to an anti-KDR antibody, and thereby provides a target for an antineoplastic agent or other moiety which is conjugated to avidin or streptavidin. Alternatively, biotin or another such moiety is linked to an anti-KDR antibody of the invention and used as a reporter, for example in a diagnostic system where a detectable signal-producing agent is conjugated to avidin or streptavidin.

Accordingly, the present receptor antagonists thus can be used in vivo and in vitro for investigative, diagnostic, prophylactic, or treatment methods, which are well known in the art. Of course, it is to be understood and expected that variations in the principles of invention herein disclosed can be made by one skilled in the art and it is intended that such modifications are to be included within the scope of the present invention.

All references mentioned herein are incorporated in their entirety.

EXAMPLES

The Examples which follow are set forth to aid in understanding the invention but are not intended to, and should not be construed to, limit its scope in any way. The Examples do not include detailed descriptions of conventional methods, such as those employed in the construction of vectors and plasmids, the insertion of genes encoding polypeptides into such vectors and plasmids, or the introduction of plasmids into host cells. Such methods are well known to those of ordinary skill in the art and are described in numerous publications including Sambrook, J., and Russell, D. W. (2001) Molecular Cloning: A Laboratory Manual, 3rd edition, Cold Spring Harbor Laboratory Press.

Example I

Production of Human Fab

Example I(a)

Proteins and Cell Lines

Primary-cultured HUVEC were obtained from Dr. S. Rafii at Cornell Medical Center, New York, and maintained in EBM-2 medium (Clonetics, Walkersville, Md.) at 37° C., 5%. $CO_2$. The soluble fusion proteins, KDR-alkaline phosphatase (AP), its immunoglobulin (Ig) domain-deletion variants, and Flk-1-AP, were expressed in stably transfected NIH 3T3 and purified from cell culture supernatants by affinity chromatography using immobilized monoclonal antibody to AP as described by Lu et al., *J. Biol. Chem.* 275: 14321-30 (2000). $VEGF_{165}$ protein was expressed in baculovirus and purified following the procedures described in Zhu et al., *Cancer Res.* 58: 3209-14 (1998). The leukemia cell lines, HL60 and HEL, were maintained in RPMI containing 10% fetal calf serum.

Example I(b)

Phage ELISA

Individual TG1 clones were picked and grown at 37° C. in 96 well plates and rescued with M13K07 helper phage as described above. The amplified phage preparation was blocked with 1/6 volume of 18% milk/PBS at RT for 1 h and added to Maxi-sorp 96-well microtiter plates (Nunc) coated with KDR-AP or AP (1 µg/ml×100 µl). After incubation at RT for 1 h the plates were washed 3 times with PBST and incubated with a rabbit anti-M13 phage-HRP conjugate (Amersharn Pharmacia Biotech, Piscataway, N.J.). The plates were washed 5 times, TMB peroxidase substrate (KPL, Gaithersburg, Md.) added, and the absorbance at 450 nm read using a microplate reader (Molecular Devices, Sunnyvale, Calif.).

Example I(c)

DNA BstN I Pattern Analysis and Nucleotide Sequencing

The diversity of the anti-KDR Fab clones after each round of selection was analyzed by restriction enzyme digestion patterns (i.e., DNA fingerprints). The Fab gene insert of individual clones was PCR amplified using primers: PUC19 reverse, 5' AGCGGATAACAATTTCACACAGG 3'; and fdtet seq, 5' GTCGTCTTTCCAGACGTTAGT 3'. The amplified product was digested with a frequent-cutting enzyme, BstN I, and analyzed on a 3% agarose gel. DNA sequences of representative clones from each digestion pattern were determined by dideoxynucleotide sequencing.

Example I(d)

Expression and Purification of Soluble Fab Fragments

Plasmids of individual clones were used to transform a nonsuppressor *E. coli* host HB2151. Expression of the Fab fragments in HB32151 was induced by culturing the cells in 2YTA medium containing 1 mM isopropyl-1-thio-β-D-galactopyranoside (IPTG, Sigma) at 30° C. A periplasmic extract of the cells was prepared by resuspending the cell pellet in 25 mM Tris (pH 7.5) containing 20% (w/v) sucrose, 200 MM NaCl, 1 mM EDTA and 0.1 mM PMSF, followed by incubation at 4° C. with gentle shaking for 1 h. After centrifugation at 15,000 rpm for 15 min, the soluble Fab protein was purified from the supernatant by affinity chromatography using a Protein G column followed the manufacturer's protocol (Amersham Pharmacia Biotech).

Example I(e)

Selection of Human Anti-KDR Fab from Phage Display Library

A large human Fab phage display library containing 3.7× $10^{10}$ clones (DeHaard et al., *J. Biol. Chem.* 274: 18218-30

(1999)) was used for the selection. The library consists of PCR-amplified antibody variable light chain genes and variable heavy chain genes fused to human constant light chain genes (κ and λ) and DNA encoding the IgG1 heavy chain $C_H1$ domain, respectively. Both heavy and light chain constructs are preceded by a signal sequence—pelB for the light chain and gene III signal sequence for the heavy chain. Heavy chain constructs further encode a portion of the gene III protein for phage display, a hexahistidine tag, and an 11 amino-acid-long c-myc tag, followed by an amber codon (TAG). The hexahistidine and c-myc tags can be used for purification or detection. The amber codon allows for phage display using suppressor hosts (such as TG1 cells) or production of Fab fragments in soluble form when transformed into a nonsuppressor host (such as HB2151 cells).

The library stock was grown to log phase, rescued with M13-KO7 helper phage and amplified overnight in 2YTAK medium (2YT containing 100 µg/ml of ampicillin and 50 µg/ml of kanamycin) at 30° C. The phage preparation was precipitated in 4% PEG/0.5M NaCl, resuspended in 3% fat-free milk/PBS containing 500 µg/ml of AP protein and incubated at 37° C. for 1 h to capture phage displaying anti-AP Fab fragments and to block other nonspecific binding.

KDR-AP (10 µg/ml in PBS) coated Maxisorp Star tubes (Nunc, Rosklide, Denmark) were first blocked with 3% milk/PBS at 37° C. for 1 h, and then incubated with the phage preparation at RT for 1 h. The tubes were washed 10 times with PBST (PBS containing 0.1% Tween-20) followed by 10 times with PBS. Bound phage were eluted at RT for 10 min with 1 ml of a freshly prepared solution of 100 mM triethylamine (Sigma, St. Louis, Mo.). The eluted phage were incubated with 10 ml of mid-log phase TG1 cells at 37° C. for 30 min stationary and 30 min shaking. The infected TG1 cells were pelleted and plated onto several large 2YTAG plates and incubated overnight at 30° C. All the colonies grown on the plates were scraped into 3 to 5 ml of 2YTA medium, mixed with glycerol (10% final concentration), aliquoted and stored at −70° C. For the next round selection, 100 µl of the phage stock was added to 25 ml of 2YTAG medium and grown to mid-log phase. The culture was rescued with M13K07 helper phage, amplified, precipitated, and used for selection followed the procedure described above, with reduced concentrations of KDR-AP immobilized on the immunotube and increased number of washes after the binding process.

A total of three rounds of selection were performed on immobilized KDR, with varying protein concentrations and number of washings after the initial binding process. After each round selection, 93 clones were randomly picked and tested by phage ELISA for binding to KDR. Seventy out of the 93 clones (75%) picked after the second selection, and greater than 90% of the recovered clones after the third selection were positive in KDR binding, suggesting a high efficiency of the selection process. DNA segments encoding the Fab from all the 70 binders identified in the second selection were amplified, digested with BstN I, and compared for fingerprint patterns. A total of 42 different patterns were observed, indicating an excellent diversity of the isolated anti-KDR Fab. Cross-reactivity examination demonstrated that 19 out of the 42 antibodies were specific KDR-binders, whereas the rest 23 antibodies bound to both KDR and its murine homologue, Flk-1. Further selection was achieved with a competitive VEGF-binding assay in which the binding of soluble KDR to immobilized VEGF in the presence or absence of the anti-KDR Fab fragments was determined. The assay identified four Fab clones that were capable of blocking the binding between VEGF and KDR. Three were KDR-specific binders and one cross-reacted with Flk-1. DNA fingerprinting and sequencing analysis confirmed that all four KDR/VEGF blocking antibodies were different (FIG. 1A) with unique DNA and amino acid sequences.

The amino acid sequences for CDR1, CDR2 and CDR3 of $V_H$ and $V_L$ for the four clones are given in Table 1.

TABLE 1

CDR sequences of selected KDR-binding human Fabs

| Clone | CDR1 | CDR2 | CDR3 |
|---|---|---|---|
| *Light Chain* | | | |
| D2C6 | RASQSVSSYLA (SEQ ID NO:1) | DSSNRAT (SEQ ID NO:2) | LQHNTFPPT (SEQ ID NO:3) |
| D2H2 | RASQGISSRLA (SEQ ID NO:4) | AASSLQT (SEQ ID NO:5) | QQANRFPPT (SEQ ID NO:6) |
| D1H4 | AGTTTDLTYYDLVS (SEQ ID NO:7) | DGNKRPS (SEQ ID NO:8) | NSYVSSRFYV (SEQ ID NO:9) |
| D1F7 | SGSTSNIGTNTAN (SEQ ID NO:10) | NNNQRPS (SEQ ID NO:11) | AAWDDSLNGHWV (SEQ ID NO:12) |
| *Heavy Chain* | | | |
| D2C6 | GFTFSSYSMN (SEQ ID NO:13) | SISSSSSYIYYADS VKG (SEQ ID NO:14) | VTDAFDI (SEQ ID NO:15) |
| D2H2 | GFTFSSYSMN (SEQ ID NO:13) | SISSSSSYIYYADS VKG (SEQ ID NO:14) | VTDAFDI (SEQ ID NO:15) |
| D1H4 | GFTFSSYSMN (SEQ ID NO:13) | SISSSSSYIYYADS VKG (SEQ ID NO:14) | VTDAFDI (SEQ ID NO:15) |
| D1F7 | GGTFSSYAIS (SEQ ID NO:16) | GGIIPIFGTANYAQ KFQG (SEQ ID NO:17) | GYDYYDSSGVAS PFDY (SEQ ID NO:18) |

Complete sequences for the $V_H$ and $V_L$ chains are presented in the Sequence Listing. For D1F7, the nucleotide and amino acid sequences for $V_H$ are represented by SEQ ID NOS:19 and 20 respectively, and the nucleotide and amino acid sequences for $V_L$ are represented by SEQ ID NOS: 21 and 22.

For D2C6, the nucleotide and amino acid sequences for $V_H$ are represented by SEQ ID NOS: 23 and 24 respectively, and the nucleotide and amino acid sequences for $V_L$ are represented by SEQ ID NOS: 25 and 26.

For D2H2, the nucleotide and amino acid sequences for $V_H$ are represented by SEQ ID NOS: 30 and 31 respectively, and the nucleotide and amino acid sequences for $V_L$ are represented by SEQ ID NOS: 32 and 33.

For D1H4, the nucleotide and amino acid sequences for $V_H$ are represented by SEQ ID NOS: 27 and 24 respectively, and the nucleotide and amino acid sequences for $V_L$ are represented by SEQ ID NOS: 28 and 29.

A second library was created combining the single heavy chain of D2C6 with a diverse population of light chains derived from the original library. Ten additional Fabs were identified, designated SA1, SA3, SB10, SB5, SC7, SD2, SD5, SF2, SF7, and 1121. The nucleotide and amino acid sequences for $V_L$ of the ten Fabs are represented as follows. For SA1, the nucleotide and amino acid sequences for $V_L$ are represented by SEQ ID NOS: 34 and 35. For SA3, the nucleotide and amino acid sequences for $V_L$ are represented by SEQ ID NOS: 36 and 37. For SB10, the nucleotide and amino acid sequences for $V_L$ are represented by SEQ ID NOS: 38 and 39. For SB5, the nucleotide and amino acid sequences for $V_L$ are represented by SEQ ID NOS: 40 and 41. For SC7, the nucleotide and amino acid sequences for $V_L$ are represented by SEQ ID NOS: 42 and 43. For SD2, the nucleotide and amino acid sequences for $V_L$ are represented by SEQ ID NOS: 44 and 45. For SD5, the nucleotide and amino acid sequences for $V_L$ are represented by SEQ ID NOS: 46 and 47. For SF2, the nucleotide and amino acid sequences for $V_L$ are represented by SEQ ID NOS: 48 and 49. For SF7, the nucleotide and amino acid sequences for $V_L$ are represented by SEQ ID NOS: 50 and 51. For 1121, the nucleotide and amino acid sequences for $V_L$ are represented by SEQ ID NOS: 52 and 53.

The $V_L$ CDR sequences are presented in Table 2.

TABLE 2

Light chain CDR sequences of KDR-binding human Fabs

| Clone | CDR1 | CDR2 | CDR3 |
|---|---|---|---|
| SA1 | TGSHSNFGAGTDV (SEQ ID NO:54) | GDSNRPS (SEQ ID NO:55) | QSYDYGLRGWV (SEQ ID NO:56) |
| SA3 | RASQNINNYLN (SEQ ID NO:57) | AASTLQS (SEQ ID NO:58) | QQYSRYPPT (SEQ ID NO:59) |
| SB10 | TGSSTDVGNYNYIS (SEQ ID NO:60) | DVTSRPS (SEQ ID NO:61) | NSYSATDTLV (SEQ ID NO:62) |
| SB5 | TGQSSNIGADYDVH (SEQ ID NO:63) | GHNNRPS (SEQ ID NO:64) | QSYDSSLSGLV (SEQ ID NO:65) |
| SC7 | RASQDISSWLA (SEQ ID NO:66) | AASLLQS (SEQ ID NO:67) | QQADSFPPT (SEQ ID NO:68) |
| SD2 | RASQSIKRWLA (SEQ ID NO:69) | AASTLQS (SEQ ID NO:70) | QQANSFPPT (SEQ ID NO:71) |
| SD5 | SGSRSNIGAHYEVQ (SEQ ID NO:72) | GDTNRPS (SEQ ID NO:73) | QSYDTSLRGPV (SEQ ID NO:74) |
| SF2 | TGSSSNIGTGYDVH (SEQ ID NO:75) | AYTNRPS (SEQ ID NO:76) | QSFDDSLNGLV (SEQ ID NO:77) |
| SF7 | TGSHSNFGAGTDVH (SEQ ID NO:78) | GDTHRPS (SEQ ID NO:79) | QSYDYGLRGWV (SEQ ID NO:80) |
| 1121 | RASQGIDNWLG (SEQ ID NO:81) | DASNLDT (SEQ ID NO:82) | QQAKAFPPT (SEQ ID NO:83) |

Example II

Assays

Example II(a)

Quantitative KDR Binding and Blocking of KDR/VEGF Interaction

In a direct binding assay, various amounts of soluble Fab proteins were added to KDR-coated 96-well Maxi-sorp microtiter plates and incubated at RT for 1 h, after which the plates were washed 3 times with PBST. The plates were then incubated at RT for 1 h with 100 µl of a rabbit anti-human Fab antibody-HRP conjugate (Jackson ImmunoResearch Laboratory Inc., West Grove, Pa.). The plates were washed and developed following the procedure described above for the phage ELISA. In a competitive KDR/VEGF blocking assay, various amounts of Fab proteins were mixed with a fixed amount of KDR-AP (100 ng) and incubated at RT for 1 h. The mixtures were then transferred to 96-well microtiter plates precoated with $VEGF_{165}$ (200 ng/well) and incubated at RT for an additional 2 h, after which the plates were washed 5 times and the substrate for AP (p-nitrophenyl phosphate, Sigma) was added. Absorbance at 405 nm was measured to quantify the bound KDR-AP molecules (8). $IC_{50}$, i.e., the Fab protein concentration required for 50% inhibition of KDR binding to VEGF, was then calculated.

The four VEGF-blocking clones (D2C6, D2H2, D1H4, D1F7) were expressed as soluble Fab and purified from periplasmic extracts of E. coli by Protein G affinity chromatography. The yield of purified Fab proteins of these clones ranged from 60 to 400 µg/liter culture. SDS-PAGE analysis of each purified Fab preparation yielded a single protein band with expected molecular size (FIG. 1B).

Figure 2:
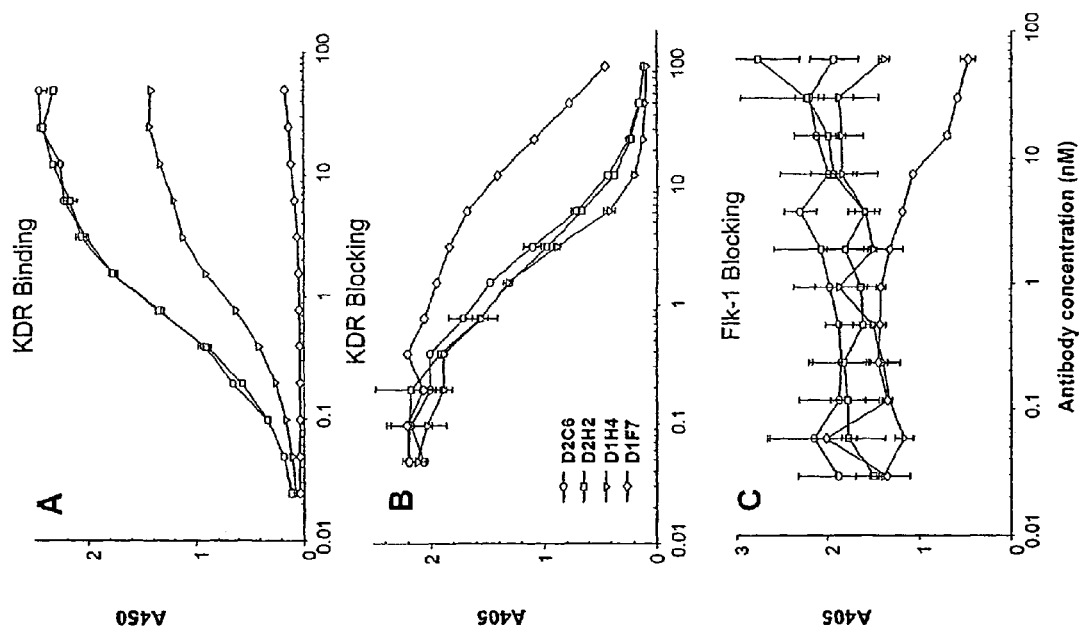
FIG. 2 depicts binding to KDR, blocking of KDR/VEGF interaction and blocking of Flk-1/VEGF interaction by human anti-KDR Fab fragments.

FIG. 2 shows the dose-dependent binding of the anti-KDR Fab fragments to immobilized receptor as assayed by a direct binding ELISA. Clone D2C6 and D2H2 are more efficient binders, followed by clone D1H4 and D1F7. All four Fabs also block KDR binding to immobilized VEGF (FIG. 2B). The antibody concentrations required for 50% of inhibition of KDR binding to VEGF are approximately 2 nM for clones D2C6, D2H2, and D1H4 and 20 nM for clone D1F7. Only clone D1F7 blocks VEGF from binding to Flk-1 (FIG. 2C), with an $IC_{50}$ of approximately 15 nM.

Example II(b)

BIAcore Analysis of the Soluble scfv

The binding kinetics of soluble Fab proteins to KDR were measured by surface plasmon resonance using a BIAcore biosensor (Pharmacia Biosensor). KDR-AP fusion protein was immobilized onto a sensor chip and soluble Fab proteins were injected at concentrations ranging from 1.5 nM to 100 nM. Sensorgrams were obtained at each concentration and were evaluated using a program, BIA Evaluation 2.0, to determine the rate constants kon and koff. Kd was calculated from the ratio of rate constants koff/kon.

All three KDR-specific Fab fragments bind to immobilized receptor with Kd of 2 to 4 nM (Table 3). The cross-reactive clone, D1F7, has a Kd of 45 nM, which is about 10- to 15-fold weaker than those of the KDR-specific clones. It is noteworthy that, although the overall Kd for the three KDR-specific Fab fragments are similar, the individual binding kinetics, i.e., the kon and koff, for these antibodies are quite different, e.g., D2C6 possesses the fastest on-rate, while D1H4 has the slowest off-rate (Table 3).

TABLE 3

Binding kinetics of the four neutralizing human anti-KDR Fab fragments

| Clone | kon ($10^4 M^{-1}S^{-1}$) | koff ($10^{-4} S^{-1}$) | Kd (nM) |
|---|---|---|---|
| Hu-2C6 Fab | 27.3 ± 8.6* | 5.38 ± 0.54 | 1.97 |
| Hu-2H2 Fab | 12.4 ± 2.9 | 4.87 ± 0.18 | 3.93 |
| Hu-1H4 Fab | 5.55 ± 0.59 | 1.53 ± 0.22 | 2.76 |
| Hu-1F7 Fab | 4.14 ± 1.21 | 18.7 ± 2.12 | 45.2 |

*All numbers are determined by BIAcore analysis and represent the mean ± SE from at least three separate determinations.

Example II(c)

Binding Epitope Mapping

The production of KDR extracellular Ig-like domain deletion variants has been previously described (Lu et al. (2000)). In an epitope-mapping assay, full length KDR-AP, Ap fusions of two KDR Ig-domain deletion variants, and Flk-1-AP were first immobilized onto a 96-well plate (Nunc) using a rabbit anti-AP antibody (DAKO-immunoglobulins, Glostrup, Denmark) as the capture reagent. The plate was then incubated with various anti-KDR Fab proteins at RT for 1 h, followed by incubation with a rabbit anti-human Fab antibody-HRP conjugate. The plate was washed and developed as described above.

Figure 3:
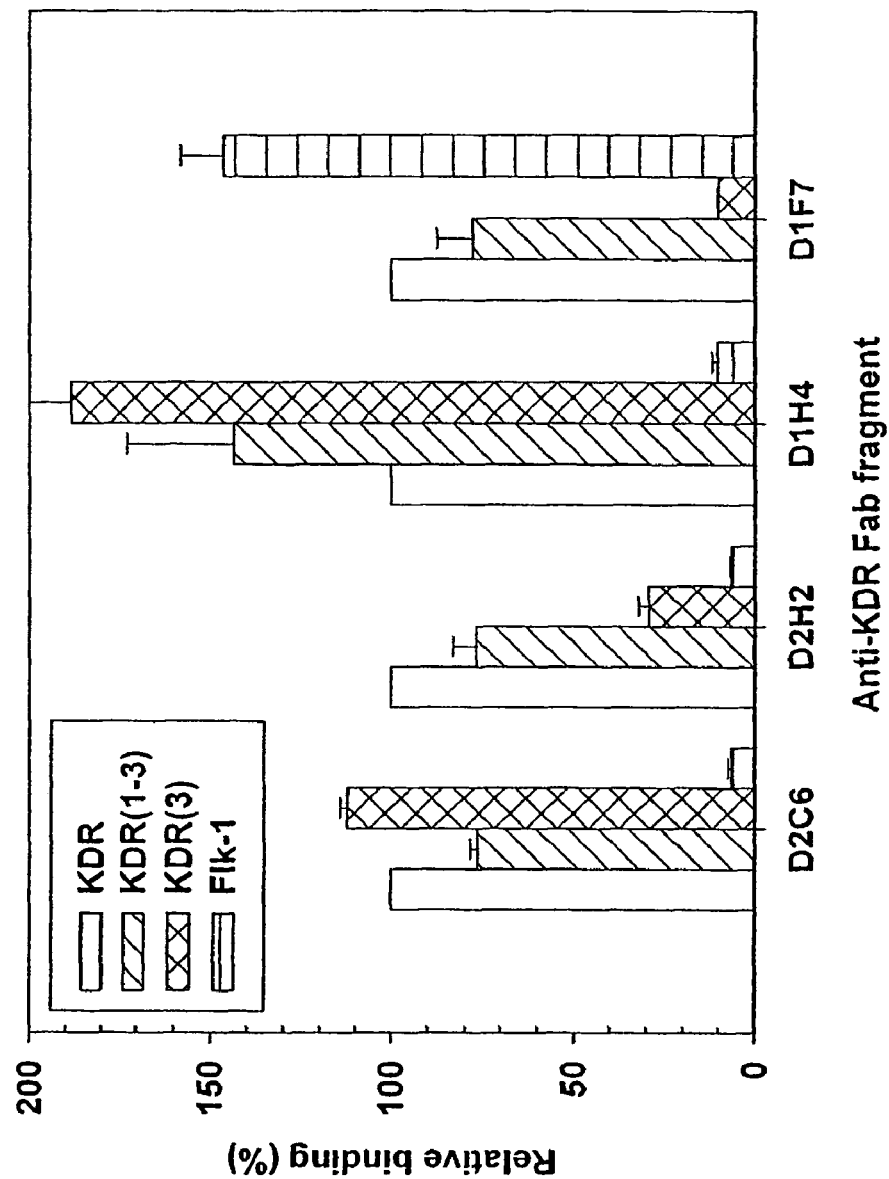
FIG. 3 depicts epitope mapping for the anti-KDR Fab fragments. KDR-AP, its domain deletion-AP variants, and Flk-1-AP were captured on a 96-well plate and incubated with human anti-KDR Fab fragments. Data are presented relative to binding of the Fab fragments to full-length KDR.

The binding epitopes of the anti-KDR Fab fragments were mapped using the full-length KDR and two KDR Ig domain-deletion variants. KDR(1-3) is a KDR variant containing the first three N-terminal Ig domains. KDR(3) is a variant containing only the third Ig domain. As shown in FIG. 3, clones D2C6 and D1H4 bind equally well to KDR, KDR(1-3) and KDR(3), thus locating their binding epitope(s) within Ig domain 3. Clones D2H2 and D1F7 bind much more efficiently to full-length KDR and KDR(1-3), indicating a broader binding epitope(s) within KDR Ig domains 1 to 3. Only clone D1F7 cross-reacts with Flk-1.

Example II(d)

Anti-mitogenic Assay

HUVEC ($5 \times 10^3$ cells/well) were plated onto 96-well tissue culture plates (Wallach, Inc., Gaithersburg, Md.) in 200 μl of EBM-2 medium without VEGF, basic fibroblast growth factor (bFGF) or epidermal growth factor (EGF) and incubated at 37° C. for 72 h. Various amounts of Fab proteins were added to duplicate wells and pre-incubated at 37° C. for 1 h, after which $VEGF_{165}$ was added to a final concentration of 16 ng/ml. After 18 h of incubation, 0.25 μCi of [$^3$H]TdR (Amersham) was added to each well and incubated for an additional 4 h. The cells were washed once with PBS, trypsinized and harvested onto a glass filter (Printed Filtermat A, Walach) with a cell harvester (Harvester 96, MACH m, TOMTEC, Orange, Conn.). The membrane was washed three times with $H_2O$ and air-dried. Scintillation fluid was added and DNA incorporated radioactivity was determined on a scintillation counter (Wallach, Model 1450 Microbeta Scintillation Counter).

Figure 4:
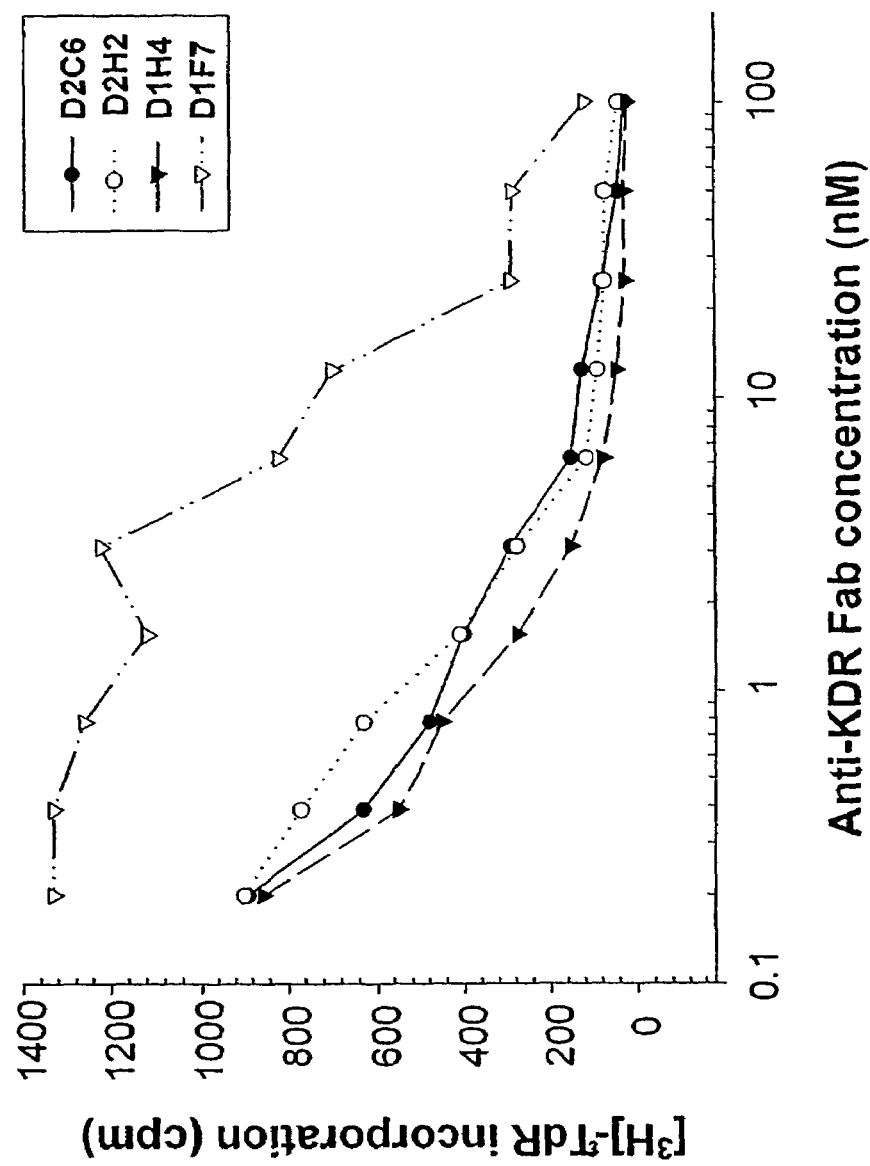
FIG. 4 depicts inhibition of VEGF-induced HUVEC mitogenesis by human anti-KDR Fab fragments. Various amounts of anti-KDR Fab fragments were added to duplicate wells and incubated at 37° C. for 1 h, after which VEGF was added to the wells to a final concentration of 16 ng/ml. Cells were harvested and DNA incorporated radioactivity was determined.

The ability of human anti-KDR Fab to block VEGF-stimulated mitogenic activity on HUVEC is shown in FIG. 4. All four human Fab fragments inhibited VEGF induced DNA synthesis in HUVEC in a dose-dependent manner. The Fab concentration that inhibited 50% ($EC_{50}$) of VEGF-stimulated [$^3$H]-TdR incorporation in HUVEC, is approximately 0.5 nM for clones D2C6 and D1H4, 0.8 nM for clone D2H2, and 15 nM for clone D1F7. Controls included VEGF only (1500 cpm) and plain medium (60 cpm). Duplicate wells were assayed. The data shown are representative of at least three separate experiments.

Example II(e)

Leukenia Migration Assay

HL60 and HEL cells were washed three times with serum-free plain RPMI 1640 medium and suspended in the medium at $1 \times 10^6$/ml. Aliquots of 100 μl cell suspension were added to either 3-μm-pore transwell inserts for HL60 cells, or 8-μm-pore transwell inserts for HEL cells (Costar®, Corning Incorporated, Corning, N.Y.) and incubated with the anti-KDR Fab proteins (5 μg/ml) for 30 min at 37° C. The inserts were then placed into the wells of 24-well plates containing 0.5 ml of serum-free RPMI 1640 with or without $VEGF_{165}$. The migration was carried out at 37° C., 5% $CO_2$ for 16-18 h for HL60 cells, or for 4 h for HEL cells. Migrated cells were collected from the lower compartments and counted with a Coulter counter (Model Z1, Coulter Electronics Ltd., Luton, England).

Figure 5:
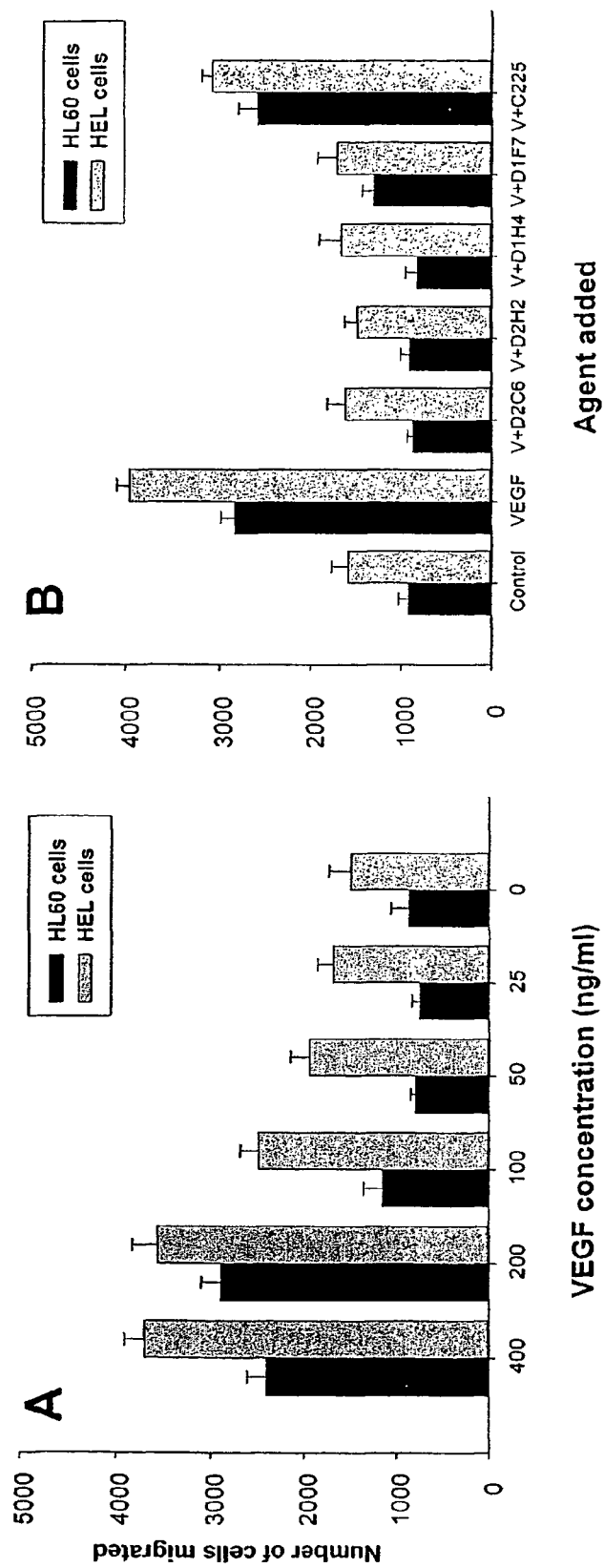
FIG. 5 depicts inhibition of VEGF-stimulated migration of human leukemia cells by the anti-KDR Fab fragments.

VEGF induced migration of HL60 and HEL cells in a dose-dependent manner with maximum stimulation achieved at 200 ng/ml (FIG. 5A). All the anti-KDR Fab fragments significantly inhibited VEGF-stimulated migration of HL60 and HEL cells (FIG. 5B). As a control, a Fab fragment of C225, an antibody directed against EGF receptor, did not show significant inhibitory effect in this assay.

Example III

Production of IgG

Example III(a)

Construction of Vectors for Expression of IgG

Separate vectors for expression of IgG light chain and heavy chains were constructed. Cloned $V_L$ genes were digested and ligated into the vector pKN100 (MRC. Cloned $V_H$ genes were digested and ligated into the vector pGID105 containing the human IgGl (γ) heavy chain constant domain. pKN100 and pGID105 are available from the MRC. Constructs were examined by restriction enzyme digestion and verified by dideoxynucleotide sequencing. In both cases expression is under control of the HCMV promoter and terminated by an artificial termination sequence.

The assembled heavy and light chain genes were then cloned into Lonza GS expression vectors pEE6.1 and pEE12.1. Heavy and light chain vectors were recombined into a single vectors for stable transfection of CHO cells and NS0 cells. Transfected cells were cultured in glutamine minus medium and expressed antibodies at levels as high as 1 g/L.

Example III(b)

Production and Characterization of Human Anti-KDR IgG

Both IMC-2C6 and IMC-1121 were produced in stably transfected NS0 cell lines grown under serum-free conditions, and were purified from batch cell culture using Protein A affinity chromatography. The purity of the antibody preparations were analyzed by SDS-PAGE, and the concentrations were determined by ELISA, using an anti-human Fc antibody as the capturing agent and an anti-human κ chain antibody-horseradish peroxidase (BRP) conjugate as the detection agent. A clinical grade antibody, IMC-C225, was used as the standard for calibration. The endotoxin level of each antibody preparations was examined to ensure the products were free of endotxin contamination.

Figure 6:
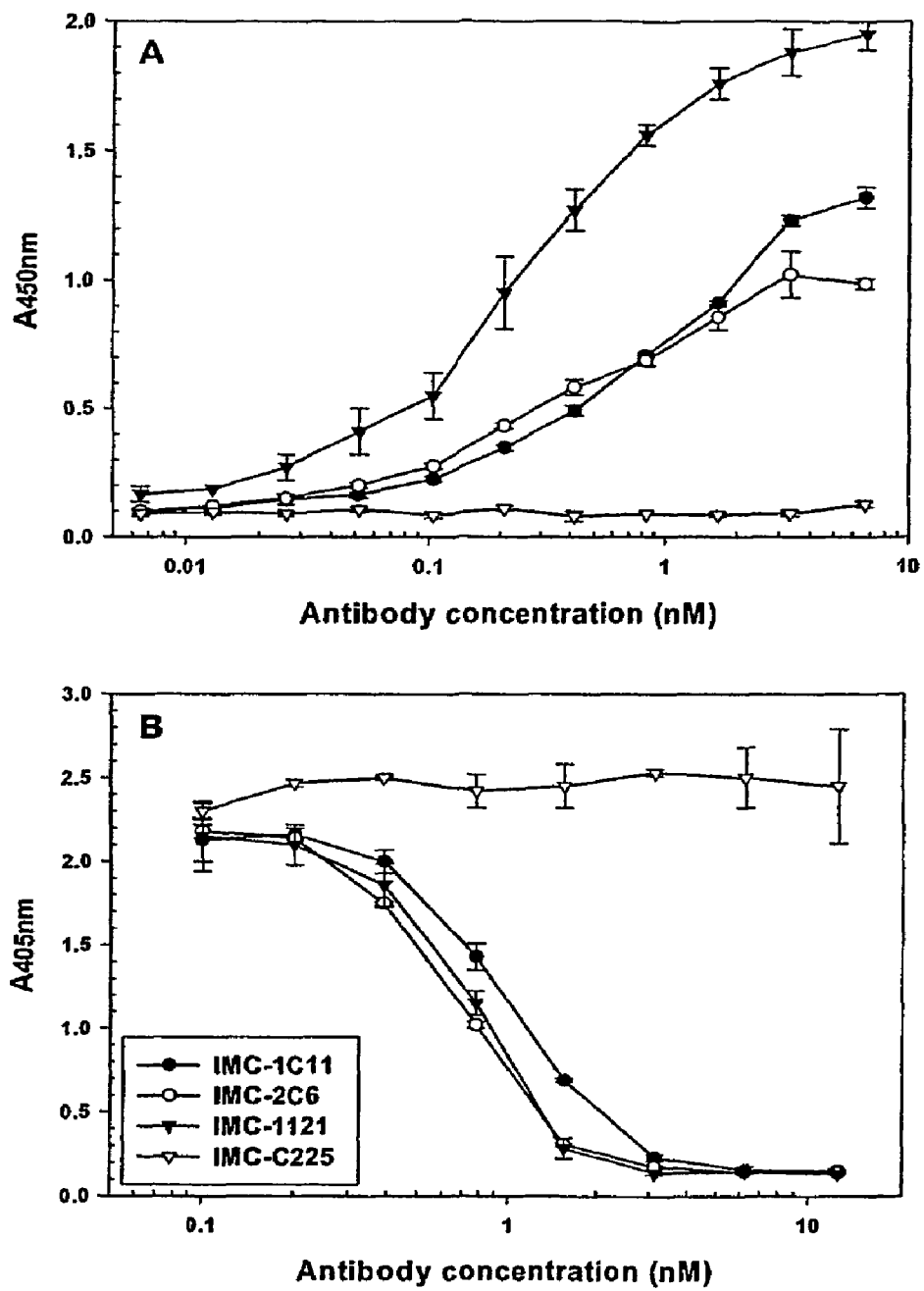
FIG. 6 depicts binding to KDR and blocking of KDR/VEGF interaction by human anti-KDR antibodies.

Anti-KDR antibodies were assessed for KDR binding and blocking of VEGF binding. In the direct binding assay, various amounts of antibodies were added to KDR-coated 96-well Maxi-sorp microtiter plates (Nunc, Roskilde, Denmark) and incubated at room temperature (RT) for 1 h, after which the plates were washed 3 times with PBS containing 0.1% Tween-20. The plates were then incubated at RT for 1 h with 100 μl of a rabbit anti-human IgG Fc-HRP conjugate (Jackson ImmunoResearch Laboratory Inc., West Grove, Pa.). The plates were washed and developed as above. Human antibodies IMC-2C6 and IMC-1121 were compared with IMC-1C11 (a mouse antibody specific for KDR) and IMC-C225 a chimeric antibody specific for EGFR). The anti-KDR antibodies bind to KDR in a dose-dependent manner, with IMC-1121 being the strongest binder (FIG. 6A).

The efficacy of the anti-KDR antibodies for blocking KDR from binding to VEGF was measured with a competition assay. Various amounts of antibodies were mixed with a fixed amount of KDR-AP (100 ng) and incubated at RT for 1 h. The mixtures were then transferred to 96-well microtiter plates precoated with VEGF$_{165}$ (200 ng/well) and incubated at RT for an additional 2 h, after which the plates were washed 5 times and the substrate for AP (p-nitrophenyl phosphate, Sigma) was added, followed by reading the absorbance at 405 nm to quantify the bound KDR-AP molecules. IC$_{50}$, i.e., the antibody concentration required for 50% inhibition of KDR binding to VEGF, was then calculated. The anti-KDR antibodies strongly blocked KDR from binding to VEGF (FIG. 6B), with similar potency. The IC$_{50}$ is approximately 0.8 to 1.0 nM for all three antibodies. The control antibody, IMC-C225 (anti-human EGFR) does not bind KDR, and does not block KDR/VEGF interaction.

Antibody affinity or avidity was determined by BIAcore analysis, as above. The binding kinetics, i.e., the association rate constant ($k_{on}$) and the dissociation rate constant ($k_{off}$), of the anti-KDR antibodies were measured and the dissociation constant, K$_d$, was calculated (Table 4).

TABLE 4

Binding kinetics of anti-KDR antibodies

| Antibody | kon (10$^4$ M$^{-1}$S$^{-1}$) | koff (10$^{-4}$ S$^{-1}$) | Kd (nM) |
| --- | --- | --- | --- |
| p1C11 scFv | 7.7 ± 2.1* | 1.0 ± 0.09 | 1.4 ± 0.3 |
| IMC-1C11 | 13.4 ± 2.9 | 0.37 ± 0.13 | 0.27 ± 0.06 |
| Hu-2C6 Fab | 17.1 ± 5.7 | 5.5 ± 0.76 | 3.6 ± 1.7 |
| IMC-2C6 IgG | 21.2 ± 8.1 | 0.43 ± 0.03 | 0.20 ± 0.01 |
| Hu-1121 Fab | 29.6 ± 7.3 | 0.31 ± 0.06 | 0.11 ± 0.02 |
| IMC-1121 IgG | 47.9 ± 2.4 | 0.25 ± 0.04 | 0.05 ± 0.01 |

*All numbers are determined by BIAcore analysis and represent the mean ± SE from at least three separate determinations.

IMC-1C11 binds to immobilized KDR with a dissociation constant (Kd) of 0.27 nM, about 5-fold higher than its Fab counterpart. The Kd for IMC-2C6 is 0.2 nM, which is about 18-fold higher than that of the monovalent Hu-2C6 Fab, mainly due to an improvement in the off-rate. Affinity maturation of Hu-2C6 led to Hu-1121 Fab with a 33-fold improvement in Kd (from 3.6 nM to 0.11 nM). Converting Hu-1121 Fab into bivalent IgG, IMC-1121, resulted in about 2-fold increase in overall binding avidity.

Example III(c)

Inhibition of VEGF Binding to Cells and VEGF-stimulated Mitogenesis of HUVEC

Figure 7:
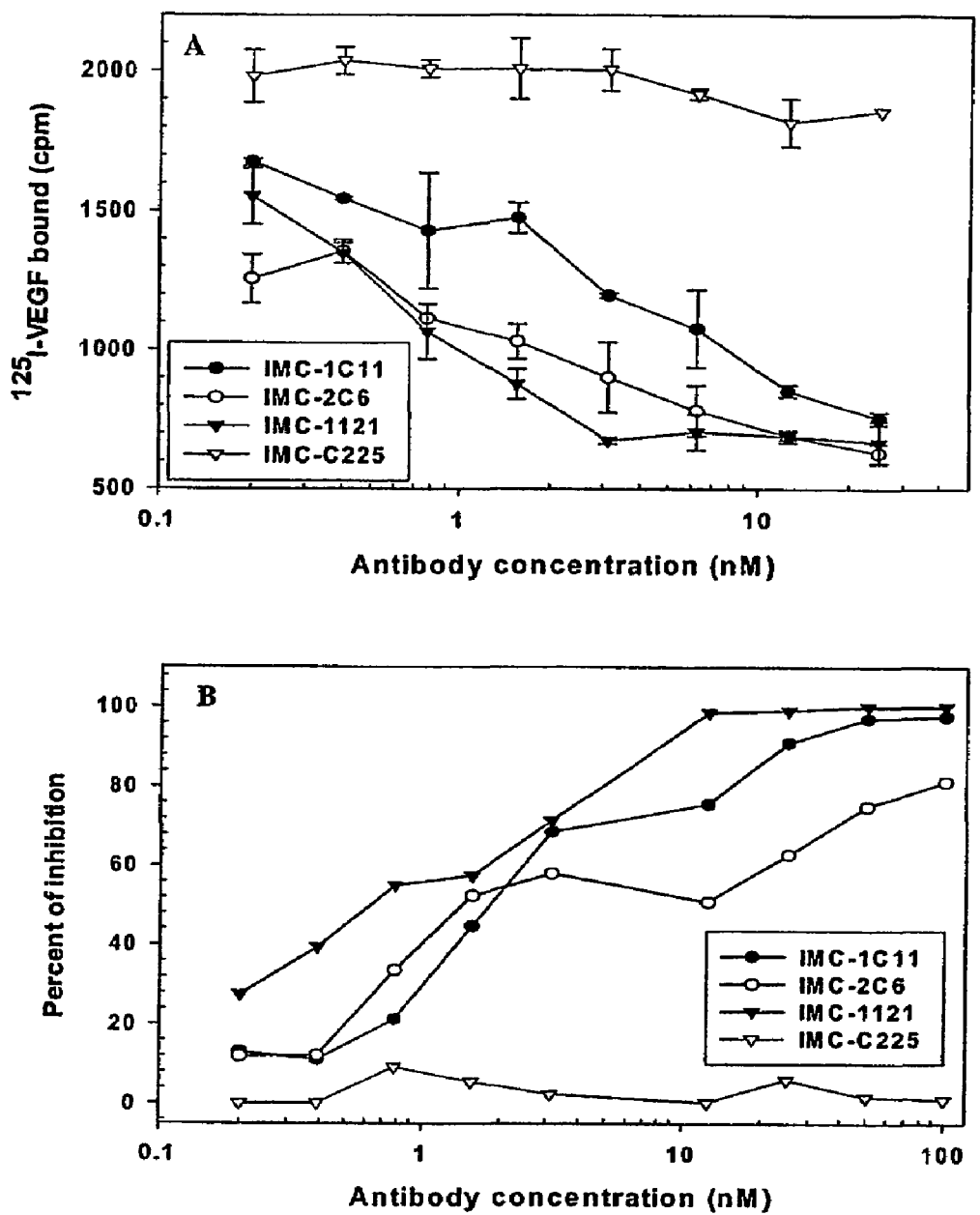
FIG. 7 depicts inhibition of VEGF binding and VEGF-induced mitogenesis of HUVEC.

In a cell-based radioimmunoassay, various amounts of anti-KDR antibodies were mixed with a fixed amount (2 ng) of $^{125}$I labeled VEGF$_{165}$ (R & D Systems) and added to a 80-90% confluent monolayer of HUVEC grown in a 96-well microtiter plate. The plate was incubated at RT for 2 h, washed 5 times with cold PBS, and the amounts of radioactivity that bound to the endothelial cells were counted. As shown in FIG. 7A, anti-KDR antibodies competed efficiently with radiolabeled VEGF for binding to HUVEC. The data represent the means±SD for triplicate determinations.

The antibodies also blocked VEGF-stimulated HUVEC mitogenesis in a dose-dependent manner (FIG. 7B). As described above for Fabs, various amounts of the anti-KDR antibodies were first pre-incubated with growth factor-starved HUVEC (5×10$^3$ cells/well) at 37° C. for 1 h, after which VEGF$_{165}$ was added to a final concentration of 16 ng/ml. After 18 h of incubation, 0.25 µCi of [$^3$H]-TdR (Amersham) was added to each well and incubated for an additional 4 h. The cells were washed, harvested, and DNA incorporated radioactivity was determined on a scintillation counter. IMC-1121, the antibody with the highest affinity, is the most efficacious inhibitor with an ED$_{50}$, i.e., the concentration that results in 50% of inhibition of [$^3$H]-TdR incorporation, of about 0.7 nM, in comparison to that of 1.5 nM for both IMC-1C11 and IMC-2C6.

Example IV

Inhibition of Leukemian Cells and Leukemia Progression

Example IV(a)

Expression of VEGF and KIDR by Leukemia Cells

Figure 8:
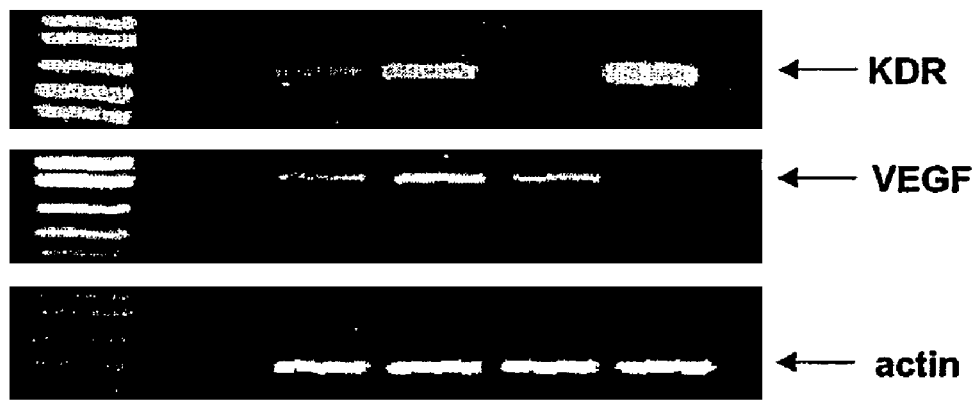
FIG. 8 depicts expression of KDR and VEGF by human leukemia cells.
Figure 8:
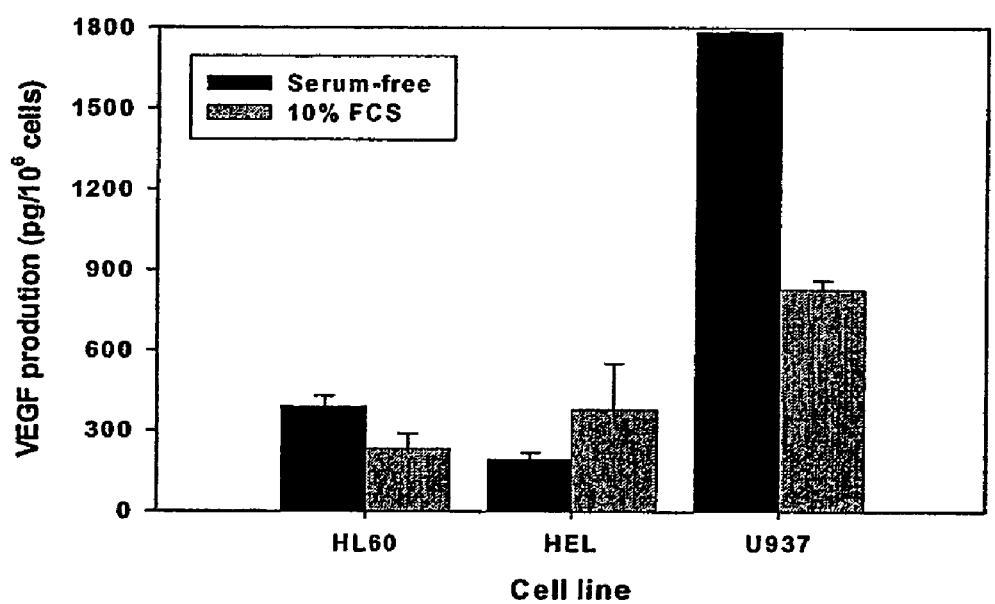

We examined VEGF and KDR expression, by RT-PCR, in three myeloid leukemia cell lines: HL60 (promyelocytic); HEL (megakaryocytic); and U937 (histiocytic). The following primers were used to amplify VEGF, Flt-1, KDR and the internal control, α-actin: VEGF forward: 5'-TCGGGCCTC-CGAAACCATGA-3' (SEQ ID NO:86), and reverse: 5'-CCTGGTGAGAGATCTGGTTC-3' (SEQ ID NO:87); Flt-1 forward: 5'-TTTGTGATTTTGGCCTTGC-3' (SEQ ID NO:88), and reverse: 5'-CAGGCTCATGAACTTGAAAGC-3' (SEQ ID NO:89); KDR forward: 5'-GTGACCAACATG-GAGTCGTG-3' (SEQ ID NO:90), and reverse: 5'-CCA-GAGATTCCATGCCACTT-3' (SEQ ID NO:91); α-actin forward: 5'-TCATGTTTGAGACCTTCAA-3' (SEQ ID NO:92), and reverse: 5'-GTCTTTGCGGATGTCCACG-3' (SEQ ID NO:93). The PCR products were analyzed on a 1% agarose gel. As shown in FIG. 8A, all three lines are positive for VEGF expression, and HL60 and BEL, but not U937, are also positive for KDR expression. The three cell lines are also positive for Flt-1 expression as detected by RT-PCT (not shown).

VEGF production was examined for the three leukemia cell lines cultured under either 10% FCS or serum-free conditions. The leukemia cells were collected, washed with plain RPMI 1640 medium and seeded in 24-well plates at density of 5×10$^5$/ml, with or without the addition of 10% FCS. The cells were cultured at 37° C. for 72 hr, after which total numbers of cells were counted using a Coulter counter (Model Z1, Coulter Electronics Ltd., Luton, England) and the VEGF concentration in the supernatant was determined using an ELISA kit (Biosource International, Camarillo, Calif.). The leukemia cells secrete significant amount of VEGF when cultured in in vitro (FIG. 8B), and both HL60 and U937 cells produced more VEGF under serum-starving conditions.

Example IV(b)

Inhibition of VEGF-induced Leukemia Cell Migration

Leukemia cell migration assays, as described in Example II(e), were performed with the three leukemia cell lines. The migration was carried out for 16-18 h for HL60 cells, or for 4 h for HEL and U937 cells.

Figure 9:
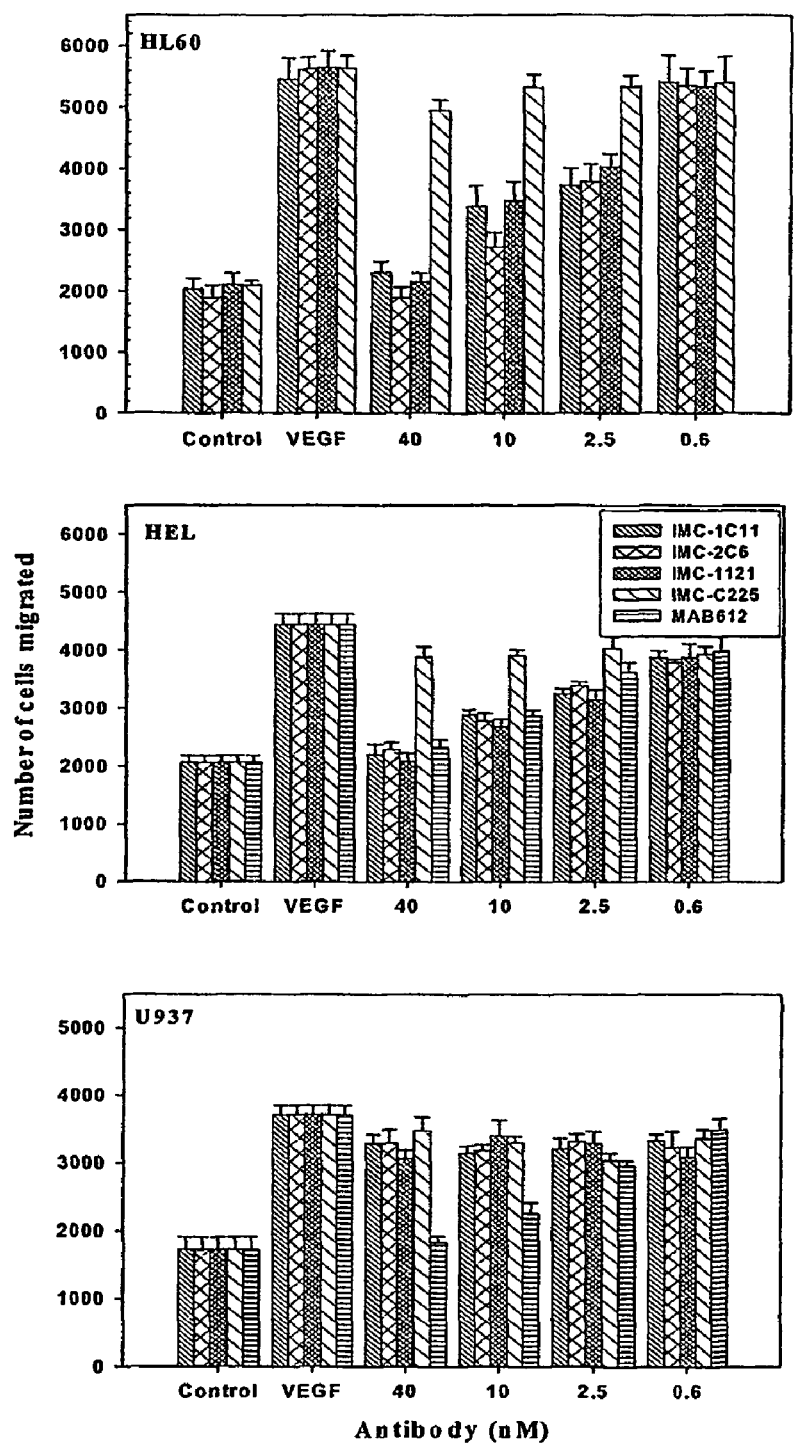
FIG. 9 depicts inhibition of VEGF-stimulated migration of human leukemia cells by human anti-KDR antibodies.

All three leukemia cell lines migrate in response to VEGF (FIG. 9). Incubation with anti-KDR antibodies inhibited, in a dose-dependent manner, VEGF-induced migration of HL60 and HEL cells (FIGS. 9A and 9B), but had no effect on migration of U937 cells that does not express KDR (FIG. 9C). The VEGF-induced migration of U937 cells was, however, efficiently inhibited by an anti-human Flt-1 antibody, Mab 612 (FIG. 9C). As expected, the anti-EGFR antibody, IMC-C225, showed no effect on VEGF-induced migration of human leukemia cells.

Example IV(b)

Inhibition of Leukemia Growth in Vivo 6 to 8-week-old sex-matched (female) NOD-SCID mice were used in all the experiments. The mice were irradiated with 3.5 Gy from a $^{137}$Cs gamma-ray source at a dose rate of about 0.9 Gy/min and intravenously inoculated with $2\times10^7$ HL60 cells. Three days after tumor inoculation, groups of 7 to 9 mice were treated twice weekly with various doses of IMC-1C11, IMC-2C6 or IMC-1121 antibodies via intraperitoneal injection. Mice were observed daily for signs of toxicity and recorded for time of survival. For statistical analysis, the non-parametric one-tailed Mann-Whitney Rank Sum test was used.

Figure 10:
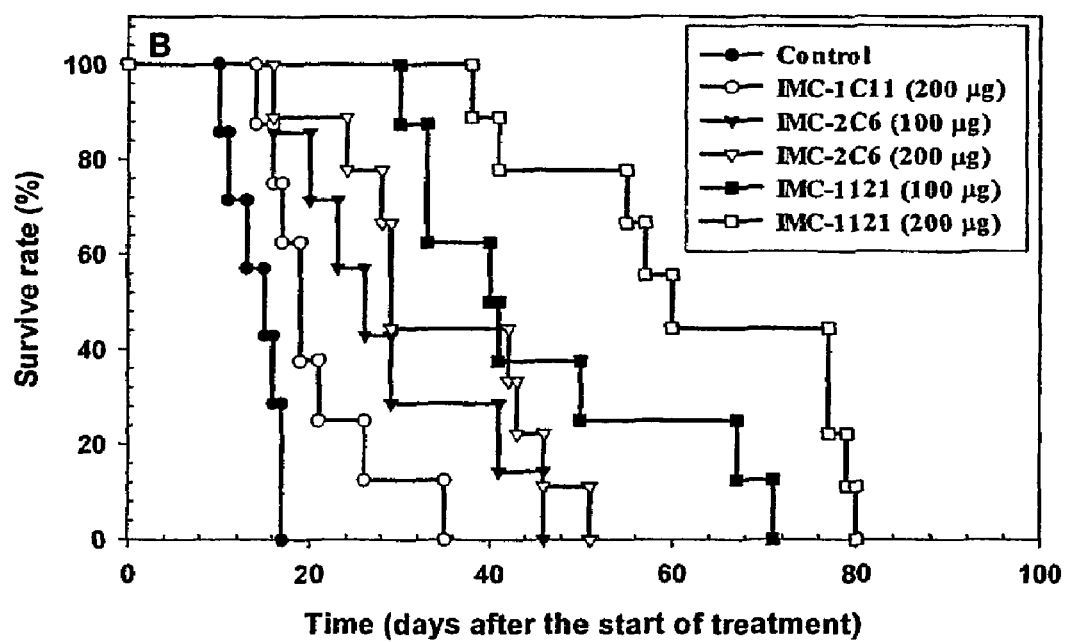
FIG. 10 depicts inhibition of leukemia advancement in vivo as determined by survival rates. Sublethally irradiated NOD-SCID mice were innoculated with 2×10$^7$ HL60 cells and treated with various doses of IMC-1C11, IMC-2C6 or IMC-1121 via intraperitoneal injection.

All untreated mice died within 17 days (FIG. 10, mean time of survival, 14±3 days). At this high tumor load, treatment with IMC-1C11 at 200 µg/mouse/injection moderately increased the survival but all mice died within 35 days (mean survival: 21±7 days; median survival 19 days, respectively. p=0.03 compared to the control group). IMC-2C6, given at the same dose of 200 µg/mouse/injection, significantly prolonged the mouse survival to 34±12 days (median=29 days. p<0.01 compared to the control and p=0.01 compared to the IMC-1C11-treated group). The antibody with the highest affinity, IMC-1121, demonstrated a much stronger anti-leukemia effect, particularly with respect to IMC-1C11. The mice treated with IMC-1121 survived 63±12 days (median=60 days. p<0.001 compared to both IMC-1C11 and IMC-2C6-treated groups). At a lower antibody dose tested (100 µg/mouse/injection), IMC-1121 was also more efficacious. Mice treated with the lower dose of IMC-1121 survived 46±16 days (median=41 days). No overt toxicities were observed in any of the antibody-treated animals throughout the course of the experiment.

Throughout this application, various publications, patents, and patent applications have been referred to. The teachings and disclosures of these publications, patents, and patent applications in their entireties are hereby incorporated by reference into this application to more fully describe the state of the art to which the present invention pertains.

It is to be understood and expected that variations in the principles of invention herein disclosed may be made by one skilled in the art and it is intended that such modifications are to be included within the scope of the present invention.

What is claimed is:

1. An isolated human antibody or fragment thereof which binds selectively to KDR, comprising complementarity determining regions represented by amino acid sequences selected from the group consisting of:

(a) SEQ ID NO:1 at CDRL1, SEQ ID NO:2 at CDRL2, SEQ ID NO:3 at CDRL3, SEQ ID NO:13 at CDRH1, SEQ ID NO:14 at CDRH2, and SEQ ID NO:15 at CDRH3;

(b) SEQ ID NO:4 at CDRL1, SEQ ID NO:5 at CDRL2, SEQ ID NO:6 at CDRL3, SEQ ID NO:13 at CDRH1, SEQ ID NO:14 at CDRH2, and SEQ ID NO:15 at CDRH3;

(c) SEQ ID NO:7 at CDRL1, SEQ ID NO:8 at CDRL2, SEQ ID NO:9 at CDRL3, SEQ ID NO:13 at CDRH1, SEQ ID NO:14 at CDRH2, and SEQ ID NO:15 at CDRH3;

(d) SEQ ID NO:10 at CDRL1, SEQ ID NO:11 at CDRL2, SEQ ID NO:12 at CDRL3, SEQ ID NO:16 at CDRH1, SEQ ID NO:17 at CDRH2, and SEQ ID NO:18 at CDRH3;

(e) SEQ ID NO:54 at CDRL1, SEQ ID NO:55 at CDRL2, SEQ ID NO:56 at CDRL3, SEQ ID NO:13 at CDRH1, SEQ ID NO:14 at CDRH2, and SEQ ID NO:15 at CDRH3;

(f) SEQ ID NO:57 at CDRL1, SEQ ID NO:58 at CDRL2, SEQ ID NO:59 at CDRL3, SEQ ID NO:13 at CDRH1, SEQ ID NO:14 at CDRH2, and SEQ ID NO:15 at CDRH3;

(g) SEQ ID NO:60 at CDRL1, SEQ ID NO:61 at CDRL2, SEQ ID NO:62 at CDRL3, SEQ ID NO:13 at CDRH1, SEQ ID NO:14 at CDRH2, and SEQ ID NO:15 at CDRH3;

81

(h) SEQ ID NO:63 at CDRL1, SEQ ID NO:64 at CDRL2, SEQ ID NO:65 at CDRL3, SEQ ID NO:13 at CDRH1, SEQ ID NO:14 at CDRH2, and SEQ ID NO:15 at CDRH3;

i) SEQ ID NO:66 at CDRL1, SEQ ID NO:67 at CDRL2, SEQ ID NO:68 at CDRL3, SEQ ID NO:13 at CDRH1, SEQ ID NO:14 at CDRH2, and SEQ ID NO:15 at CDRH3;

(j) SEQ ID NO:69 at CDRL1, SEQ ID NO:70 at CDRL2, SEQ ID NO:71 at CDRL3, SEQ ID NO:13 at CDRH1, SEQ ID NO:14 at CDRH2, and SEQ ID NO:15 at CDRH3;

(k) SEQ ID NO:72 at CDRL1, SEQ ID NO:73 at CDRL2, SEQ ID NO:74 at CDRL3, SEQ ID NO:13 at CDRH1, SEQ ID NO:14 at CDRH2, and SEQ ID NO:15 at CDRH3;

(l) SEQ ID NO:75 at CDRL1, SEQ ID NO:76 at CDRL2, SEQ ID NO:77 at CDRL3, SEQ ID NO:13 at CDRH1, SEQ ID NO:14 at CDRH2, and SEQ ID NO:15 at CDRH3;

(m) SEQ ID NO:78 at CDRL1, SEQ ID NO:79 at CDRL2, SEQ ID NO:80 at CDRL3, SEQ ID NO:13 at CDRH1, SEQ ID NO:14 at CDRH2, and SEQ ID NO:15 at CDRH3; and (n) SEQ ID NO:81 at CDRL1, SEQ ID NO:82 at CDRL2, SEQ ID NO:83 at CDRL3, SEQ ID NO:13 at CDRH1, SEQ ID NO:14 at CDRH2, and SEQ ID NO:15 at CDRH3.

2. The antibody of claim 1, wherein the fragment is selected from the group consisting of a single chain antibody, a Fab, a single chain Fv, a diabody, and a triabody.

3. The antibody of claim 1, wherein the antibody or fragment thereof inhibits binding of VEGF to KDR.

4. The antibody of claim 1, wherein the antibody comprises complementarity determining regions represented by SEQ ID NO:1 at CDRL1; SEQ ID NO:2 at CDRL2; SEQ ID NO:3 at CDRL3; SEQ ID NO:13 at CDRH1; SEQ ID NO:14 at CDRH2; and SEQ ID NO:15 at CDRH3.

5. The antibody of claim 4, wherein the antibody comprises a light chain variable domain represented by SEQ ID NO:26 and a heavy chain variable domain represented by SEQ ID NO:24.

6. The antibody of claim 1, wherein the antibody comprises complementarity determining regions represented by SEQ ID NO:81 at CDRL1; SEQ ID NO:82 at CDRl2; SEQ ID NO:83 at CDRL3; SEQ ID NO:13 at CDRH1; SEQ ID NO:14 at CDRH2; and SEQ ID NO:15 at CDRH3.

7. The antibody of claim 6, wherein the antibody comprises a light chain variable domain represented by SEQ ID NO:53 and a heavy chain variable domain represented by SEQ ID NO:24.

8. The antibody of claim 1, wherein the antibody comprises a heavy chain variable domain selected from the group consisting of SEQ ID NO:20, SEQ ID NO:24, and SEQ ID NO:31.

9. The antibody of claim 1, wherein the antibody comprises a light chain variable domain selected from the group consisting of SEQ ID NO:22, SEQ ID NO:26, SEQ ID NO:29, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, and SEQ ID NO:53.

10. An isolated polynucleotide which comprises a nucleotide sequence that encodes an amino acid sequence selected from the group consisting of SEQ ID NO:20, SEQ ID NO:22, SEQ ID NO:24, SEQ ID NO:26, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, and SEQ ID NO:53.

82

11. The polynucleotide of claim 10, wherein the nucleotide sequence is SEQ ID NO:23.

12. The polynucleotide of claim 10, wherein the nucleotide sequence is SEQ ID NO:25.

13. The polynucleotide of claim 10, wherein the nucleotide sequence is SEQ ID NO:52.

14. An expression vector comprising the polynucleotide of claim 10.

15. A isolated recombinant host cell comprising the expression vector of claim 14.

16. The isolated recombinant host cell of claim 15 which produces a polypeptide comprising SEQ ID NO:24 and a polypeptide comprising SEQ ID NO:26.

17. The isolated recombinant host cell of claim 15 which produces a polypeptide comprising SEQ ID NO:24 and a polypeptide comprising SEQ ID NO:53.

18. The antibody of claim 1, wherein the antibody comprises complementarity determining regions represented by SEQ ID NO:4 at CDRL1, SEQ ID NO:5 at CDRL2, SEQ ID NO:6 at CDRL3, SEQ ID NO:13 at CDRH1, SEQ ID NO:14 at CDRH2, and SEQ ID NO:15 at CDRH3.

19. The antibody of claim 18, wherein the antibody comprises a light chain variable domain represented by SEQ ID NO:33 and a heavy chain variable domain represented by SEQ ID NO:31.

20. The antibody of claim 1, wherein the antibody comprises complementarity determining regions represented by SEQ ID NO:7 at CDRL1, SEQ ID NO:8 at CDRL2, SEQ ID NO:9 at CDRL3, SEQ ID NO:13 at CDRH1, SEQ ID NO:14 at CDRH2, and SEQ ID NO:15 at CDRH3.

21. The antibody of claim 20, wherein the antibody comprises a light chain variable domain represented by SEQ ID NO:29 and a heavy chain variable domain represented by SEQ ID NO:24.

22. The antibody of claim 1, wherein the antibody comprises complementarity determining regions represented by SEQ ID NO:10 at CDRL1, SEQ ID NO:11 at CDRL2, SEQ ID NO:12 at CDRL3, SEQ ID NO:16 at CDRH1, SEQ ID NO:17 at CDRH2, and SEQ ID NO:18 at CDRH3.

23. The antibody of claim 22, wherein the antibody comprises a light chain variable domain represented by SEQ ID NO:22 and a heavy chain variable domain represented by SEQ ID NO:20.

24. The antibody of claim 1, wherein the antibody comprises complementarity determining regions represented by SEQ ID NO:54 at CDRL1, SEQ ID NO:55 at CDRL2, SEQ ID NO:56 at CDRL3, SEQ ID NO:13 at CDRH1, SEQ ID NO:14 at CDRH2, and SEQ ID NO:15 at CDRH3.

25. The antibody of claim 24, wherein the antibody comprises a light chain variable domain represented by SEQ ID NO:35 and a heavy chain variable domain represented by SEQ ID NO:24.

26. The antibody of claim 1, wherein the antibody comprises complementarity determining regions represented by SEQ ID NO:57 at CDRL1, SEQ ID NO:58 at CDRL2, SEQ ID NO:59 at CDRL3, SEQ ID NO:13 at CDRH1, SEQ ID NO:14 at CDRH2, and SEQ ID NO:15 at CDRH3.

27. The antibody of claim 26, wherein the antibody comprises a light chain variable domain represented by SEQ ID NO:37 and a heavy chain variable domain represented by SEQ ID NO:24.

28. The antibody of claim 1, wherein the antibody comprises complementarity determining regions represented by SEQ ID NO:60 at CDRL1, SEQ ID NO:61 at CDRL2, SEQ ID NO:62 at CDRL3, SEQ ID NO:13 at CDRH1, SEQ ID NO:14 at CDRH2, and SEQ ID NO:15 at CDRH3.

29. The antibody of claim 28, wherein the antibody comprises a light chain variable domain represented by SEQ ID NO:39 and a heavy chain variable domain represented by SEQ ID NO:24.

30. The antibody of claim 1, wherein the antibody comprises complementarity determining regions represented by SEQ ID NO:63 at CDRL1, SEQ ID NO:64 at CDRL2, SEQ ID NO:65 at CDRL3, SEQ ID NO:13 at CDRH1, SEQ ID NO:14 at CDRH2, and SEQ ID NO:15 at CDRH3.

31. The antibody of claim 30, wherein the antibody comprises a light chain variable domain represented by SEQ ID NO:41 and a heavy chain variable domain represented by SEQ ID NO:24.

32. The antibody of claim 1, wherein the antibody comprises complementarity determining regions represented by SEQ ID NO:66 at CDRL1, SEQ ID NO:67 at CDRL2, SEQ ID NO:68 at CDRL3, SEQ ID NO:13 at CDRH1, SEQ ID NO:14 at CDRH2, and SEQ ID NO:15 at CDRH3.

33. The antibody of claim 32, wherein the antibody comprises a light chain variable domain represented by SEQ ID NO:43 and a heavy chain variable domain represented by SEQ ID NO:24.

34. The antibody of claim 1, wherein the antibody comprises complementarity determining regions represented by SEQ ID NO:69 at CDRL1, SEQ ID NO:70 at CDRL2, SEQ ID NO:71 at CDRL3, SEQ ID NO:13 at CDRH1, SEQ ID NO:14 at CDRH2, and SEQ ID NO:15 at CDRH3.

35. The antibody of claim 34, wherein the antibody comprises a light chain variable domain represented by SEQ ID NO:45 and a heavy chain variable domain represented by SEQ ID NO:24.

36. The antibody of claim 1, wherein the antibody comprises complementarity determining regions represented by SEQ ID NO:72 at CDRL1, SEQ ID NO:73 at CDRL2, SEQ ID NO:74 at CDRL3, SEQ ID NO:13 at CDRH1, SEQ ID NO:14 at CDRH2, and SEQ ID NO:15 at CDRH3.

37. The antibody of claim 36, wherein the antibody comprises a light chain variable domain represented by SEQ ID NO:47 and a heavy chain variable domain represented by SEQ ID NO:24.

38. The antibody of claim 1, wherein the antibody comprises complementarity determining regions represented by SEQ ID NO:75 at CDRL1, SEQ ID NO:76 at CDRL2, SEQ ID NO:77 at CDRL3, SEQ ID NO:13 at CDRH1, SEQ ID NO:14 at CDRH2, and SEQ ID NO:15 at CDRH3.

39. The antibody of claim 38, wherein the antibody comprises a light chain variable domain represented by SEQ ID NO:49 and a heavy chain variable domain represented by SEQ ID NO:24.

40. The antibody of claim 1, wherein the antibody comprises complementarity determining regions represented by SEQ ID NO:78 at CDRL1, SEQ ID NO:79 at CDRL2, SEQ ID NO:80 at CDRL3, SEQ ID NO:13 at CDRH1, SEQ ID NO:14 at CDRH2, and SEQ ID NO:15 at CDRH3.

41. The antibody of claim 40, wherein the antibody comprises a light chain variable domain represented by SEQ ID NO:51 and a heavy chain variable domain represented by SEQ ID NO:24.

42. A isolated recombinant host cell of claim 15 which produces a polypeptide comprising SEQ ID NO:31 and a polypeptide comprising SEQ ID NO:33.

43. A isolated recombinant host cell of claim 15 which produces a polypeptide comprising SEQ ID NO:29 and a polypeptide comprising SEQ ID NO:24.

44. A isolated recombinant host cell of claim 15 which produces a polypeptide comprising SEQ ID NO:20 and a polypeptide comprising SEQ ID NO:22.

45. A isolated recombinant host cell of claim 15 which produces a polypeptide comprising SEQ ID NO:35 and a polypeptide comprising SEQ ID NO:24.

46. A isolated recombinant host cell of claim 15 which produces a polypeptide comprising SEQ ID NO:37 and a polypeptide comprising SEQ ID NO:24.

47. A isolated recombinant host cell of claim 15 which produces a polypeptide comprising SEQ ID NO:39 and a polypeptide comprising SEQ ID NO:24.

48. A isolated recombinant host cell of claim 15 which produces a polypeptide comprising SEQ ID NO:41 and a polypeptide comprising SEQ ID NO:24.

49. A isolated recombinant host cell of claim 15 which produces a polypeptide comprising SEQ ID NO:43 and a polypeptide comprising SEQ ID NO:24.

50. A isolated recombinant host cell of claim 15 which produces a polypeptide comprising SEQ ID NO:45 and a polypeptide comprising SEQ ID NO:24.

51. A isolated recombinant host cell of claim 15 which produces a polypeptide comprising SEQ ID NO:47 and a polypeptide comprising SEQ ID NO:24.

52. A isolated recombinant host cell of claim 15 which produces a polypeptide comprising SEQ ID NO:49 and a polypeptide comprising SEQ ID NO:24.

53. A isolated recombinant host cell of claim 15 which produces a polypeptide comprising SEQ ID NO:51 and a polypeptide comprising SEQ ID NO:24.

* * * * *

UNITED STATES PATENT AND TRADEMARK OFFICE
CERTIFICATE OF CORRECTION

PATENT NO.       : 7,498,414 B2
APPLICATION NO.  : 10/506997
DATED            : March 3, 2009
INVENTOR(S)      : Zhenping Zhu Page 1 of 1

It is certified that error appears in the above-identified patent and that said Letters Patent is hereby corrected as shown below:

Issued Patent

| Column | Line | Description of Error |
|---|---|---|
| On the Title Page Col. 2 (Abstract) | 1 | Delete "an" prior to "antibodies that bind" |
| On the Title Page Col. 2 (Abstract) | 3 | Delete "s" after "neutralize" |

In the Specification

| Column | Line | Description of Error |
|---|---|---|
| 4 | 22 | Delete "DKR" and insert -- KDR -- |
| 17 | 60 | Insert -- of the -- prior to "23" |
| 21 | 56 | Delete "Leukenia" prior to "Migration Assay" and insert -- Lukemia -- |
| 22 | 34 | Delete "s" after "vector" |
| 22 | 53 | Delete "s" after "preparation" |
| 24 | 21 | Delete "KIDR" and insert -- KDR -- |

In the Claims

| Column | Line | Description of Error |
|---|---|---|
| 81 | 36 | In Claim 4, delete "I" prior to "SEQ ID NO:2" and insert -- 1 -- |
| 81 | 45 | In Claim 6, delete "I" prior to "SEQ ID NO:82" and insert -- 1 -- |
| 81 | 45 | In Claim 6, delete "I" in "CDRI2" and insert -- L -- |

Signed and Sealed this
Sixteenth Day of December, 2014

Michelle K. Lee
*Deputy Director of the United States Patent and Trademark Office*

```
                       SEQUENCE LISTING

<160> NUMBER OF SEQ ID NOS: 93

<210> SEQ ID NO 1
<211> LENGTH: 11
<212> TYPE: PRT
<213> ORGANISM: Human

<400> SEQUENCE: 1

Arg Ala Ser Gln Ser Val Ser Ser Tyr Leu Ala
                5                   10

<210> SEQ ID NO 2
<211> LENGTH: 7
<212> TYPE: PRT
<213> ORGANISM: Human

<400> SEQUENCE: 2

Asp Ser Ser Asn Arg Ala Thr
                5

<210> SEQ ID NO 3
<211> LENGTH: 9
<212> TYPE: PRT
<213> ORGANISM: Human

<400> SEQUENCE: 3

Leu Gln His Asn Thr Phe Pro Pro Thr
                5

<210> SEQ ID NO 4
<211> LENGTH: 11
<212> TYPE: PRT
<213> ORGANISM: Human

<400> SEQUENCE: 4
```

Arg Ala Ser Gln Gly Ile Ser Ser Arg Leu Ala
                5                   10

<210> SEQ ID NO 5
<211> LENGTH: 7
<212> TYPE: PRT
<213> ORGANISM: Human

<400> SEQUENCE: 5

Ala Ala Ser Ser Leu Gln Thr
                5

<210> SEQ ID NO 6
<211> LENGTH: 9
<212> TYPE: PRT
<213> ORGANISM: Human

<400> SEQUENCE: 6

Gln Gln Ala Asn Arg Phe Pro Pro Thr
                5

<210> SEQ ID NO 7
<211> LENGTH: 14
<212> TYPE: PRT
<213> ORGANISM: Human

<400> SEQUENCE: 7

Ala Gly Thr Thr Thr Asp Leu Thr Tyr Tyr Asp Leu Val Ser
                5                   10

<210> SEQ ID NO 8
<211> LENGTH: 7
<212> TYPE: PRT
<213> ORGANISM: Human

<400> SEQUENCE: 8

Asp Gly Asn Lys Arg Pro Ser
                5

<210> SEQ ID NO 9
<211> LENGTH: 10
<212> TYPE: PRT
<213> ORGANISM: Human

<400> SEQUENCE: 9

Asn Ser Tyr Val Ser Ser Arg Phe Tyr Val
                5                   10

<210> SEQ ID NO 10
<211> LENGTH: 13
<212> TYPE: PRT
<213> ORGANISM: Human

<400> SEQUENCE: 10

Ser Gly Ser Thr Ser Asn Ile Gly Thr Asn Thr Ala Asn
                5                   10

<210> SEQ ID NO 11
<211> LENGTH: 7
<212> TYPE: PRT
<213> ORGANISM: Human

<400> SEQUENCE: 11

Asn Asn Asn Gln Arg Pro Ser

```
<210> SEQ ID NO 12
<211> LENGTH: 12
<212> TYPE: PRT
<213> ORGANISM: Human

<400> SEQUENCE: 12

Ala Ala Trp Asp Asp Ser Leu Asn Gly His Trp Val
                 5                   10

<210> SEQ ID NO 13
<211> LENGTH: 10
<212> TYPE: PRT
<213> ORGANISM: Human

<400> SEQUENCE: 13

Gly Phe Thr Phe Ser Ser Tyr Ser Met Asn
                 5                   10

<210> SEQ ID NO 14
<211> LENGTH: 17
<212> TYPE: PRT
<213> ORGANISM: Human

<400> SEQUENCE: 14

Ser Ile Ser Ser Ser Ser Ser Tyr Ile Tyr Tyr Ala Asp Ser Val Lys
                 5                   10                  15

Gly
 17

<210> SEQ ID NO 15
<211> LENGTH: 7
<212> TYPE: PRT
<213> ORGANISM: Human

<400> SEQUENCE: 15

Val Thr Asp Ala Phe Asp Ile
                 5

<210> SEQ ID NO 16
<211> LENGTH: 10
<212> TYPE: PRT
<213> ORGANISM: Human

<400> SEQUENCE: 16

Gly Gly Thr Phe Ser Ser Tyr Ala Ile Ser
                 5                   10

<210> SEQ ID NO 17
<211> LENGTH: 18
<212> TYPE: PRT
<213> ORGANISM: Human

<400> SEQUENCE: 17

Gly Gly Ile Ile Pro Ile Phe Gly Thr Ala Asn Tyr Ala Gln Lys Phe
                 5                   10                  15

Gln Gly
     18

<210> SEQ ID NO 18
<211> LENGTH: 16
<212> TYPE: PRT
<213> ORGANISM: Human
```

<400> SEQUENCE: 18

Gly Tyr Asp Tyr Tyr Asp Ser Ser Gly Val Ala Ser Pro Phe Asp Tyr
              5                   10                  15

<210> SEQ ID NO 19
<211> LENGTH: 375
<212> TYPE: DNA
<213> ORGANISM: Human

<400> SEQUENCE: 19 gag gtc cag ctg gtg cag tct ggg gct gag gtg aag aag cct ggg gcc      48
Glu Val Gln Leu Val Gln Ser Gly Ala Glu Val Lys Lys Pro Gly Ala
              5                   10                  15 tca gtg aag gtc tcc tgc aag gct tct gga ggc acc ttc agc agc tat      96
Ser Val Lys Val Ser Cys Lys Ala Ser Gly Gly Thr Phe Ser Ser Tyr
         20                  25                  30 gct atc agc tgg gtg cga cag gcc cct gga caa ggg ctt gag tgg atg     144
Ala Ile Ser Trp Val Arg Gln Ala Pro Gly Gln Gly Leu Glu Trp Met
     35                  40                  45 gga ggg atc atc cct atc ttt ggt aca gca aac tac gca cag aag ttc     192
Gly Gly Ile Ile Pro Ile Phe Gly Thr Ala Asn Tyr Ala Gln Lys Phe
 50                  55                  60 cag ggc aga gtc act ttt acc gcg gac aaa tcc acg agt aca gcc tat     240
Gln Gly Arg Val Thr Phe Thr Ala Asp Lys Ser Thr Ser Thr Ala Tyr
65                   70                  75                  80 atg gag ttg agg agc ctg aga tct gac gac acg gcc gtg tat tac tgt     288
Met Glu Leu Arg Ser Leu Arg Ser Asp Asp Thr Ala Val Tyr Tyr Cys
                 85                  90                  95 gcg aga gga tac gat tac tat gat agt agt ggc gtg gct tcc ccc ttt     336
Ala Arg Gly Tyr Asp Tyr Tyr Asp Ser Ser Gly Val Ala Ser Pro Phe
            100                 105                 110 gac tac tgg ggc cag gga acc ctg gtc acc gtc tca agc                 375
Asp Tyr Trp Gly Gln Gly Thr Leu Val Thr Val Ser Ser
        115                 120                 125

<210> SEQ ID NO 20
<211> LENGTH: 125
<212> TYPE: PRT
<213> ORGANISM: Human

<400> SEQUENCE: 20

Glu Val Gln Leu Val Gln Ser Gly Ala Glu Val Lys Lys Pro Gly Ala
              5                   10                  15

Ser Val Lys Val Ser Cys Lys Ala Ser Gly Gly Thr Phe Ser Ser Tyr
         20                  25                  30

Ala Ile Ser Trp Val Arg Gln Ala Pro Gly Gln Gly Leu Glu Trp Met
     35                  40                  45

Gly Gly Ile Ile Pro Ile Phe Gly Thr Ala Asn Tyr Ala Gln Lys Phe
 50                  55                  60

Gln Gly Arg Val Thr Phe Thr Ala Asp Lys Ser Thr Ser Thr Ala Tyr
65                   70                  75                  80

Met Glu Leu Arg Ser Leu Arg Ser Asp Asp Thr Ala Val Tyr Tyr Cys
                 85                  90                  95

Ala Arg Gly Tyr Asp Tyr Tyr Asp Ser Ser Gly Val Ala Ser Pro Phe
            100                 105                 110

Asp Tyr Trp Gly Gln Gly Thr Leu Val Thr Val Ser Ser
        115                 120                 125

<210> SEQ ID NO 21
<211> LENGTH: 333
<212> TYPE: DNA
<213> ORGANISM: Human

<400> SEQUENCE: 21

| cag | tct | gtg | ctg | act | cag | cca | ccc | tca | gcg | tct | ggg | acc | ccc | ggg | cag | 48 |
| Gln | Ser | Val | Leu | Thr | Gln | Pro | Pro | Ser | Ala | Ser | Gly | Thr | Pro | Gly | Gln | |
| | | | | 5 | | | | | 10 | | | | | 15 | | |

| agg | gtc | acc | atc | tct | tgt | tct | gga | agc | acc | tcc | aac | atc | ggt | act | aat | 96 |
| Arg | Val | Thr | Ile | Ser | Cys | Ser | Gly | Ser | Thr | Ser | Asn | Ile | Gly | Thr | Asn | |
| | | | 20 | | | | | 25 | | | | | 30 | | | |

| act | gca | aac | tgg | ttc | cag | cag | ctc | cca | gga | acg | gcc | ccc | aaa | ctc | ctc | 144 |
| Thr | Ala | Asn | Trp | Phe | Gln | Gln | Leu | Pro | Gly | Thr | Ala | Pro | Lys | Leu | Leu | |
| | | 35 | | | | | 40 | | | | | 45 | | | | |

| atc | cac | aat | aat | aat | cag | cgg | ccc | tca | ggg | gtc | cct | gac | cga | ttc | tct | 192 |
| Ile | His | Asn | Asn | Asn | Gln | Arg | Pro | Ser | Gly | Val | Pro | Asp | Arg | Phe | Ser | |
| | 50 | | | | | 55 | | | | | 60 | | | | | |

| ggc | tcc | aag | tct | ggc | acc | tca | gcc | tcc | ctg | gcc | atc | agt | ggg | ctc | cag | 240 |
| Gly | Ser | Lys | Ser | Gly | Thr | Ser | Ala | Ser | Leu | Ala | Ile | Ser | Gly | Leu | Gln | |
| 65 | | | | | 70 | | | | | 75 | | | | | 80 | |

| tct | gag | gat | gag | gct | gat | tat | tac | tgt | gca | gca | tgg | gat | gac | agc | ctg | 288 |
| Ser | Glu | Asp | Glu | Ala | Asp | Tyr | Tyr | Cys | Ala | Ala | Trp | Asp | Asp | Ser | Leu | |
| | | | | 85 | | | | | 90 | | | | | 95 | | |

| aat | ggc | cat | tgg | gtg | ttc | ggc | gga | ggg | acc | aag | ctg | acc | gtc | ctg | | 333 |
| Asn | Gly | His | Trp | Val | Phe | Gly | Gly | Gly | Thr | Lys | Leu | Thr | Val | Leu | | |
| | | | 100 | | | | | 105 | | | | | 110 | | | |

<210> SEQ ID NO 22
<211> LENGTH: 111
<212> TYPE: PRT
<213> ORGANISM: Human

<400> SEQUENCE: 22

Gln Ser Val Leu Thr Gln Pro Pro Ser Ala Ser Gly Thr Pro Gly Gln
              5                      10                 15

Arg Val Thr Ile Ser Cys Ser Gly Ser Thr Ser Asn Ile Gly Thr Asn
           20                   25                   30

Thr Ala Asn Trp Phe Gln Gln Leu Pro Gly Thr Ala Pro Lys Leu Leu
      35                      40                   45

Ile His Asn Asn Asn Gln Arg Pro Ser Gly Val Pro Asp Arg Phe Ser
  50                      55                   60

Gly Ser Lys Ser Gly Thr Ser Ala Ser Leu Ala Ile Ser Gly Leu Gln
65                   70                   75                 80

Ser Glu Asp Glu Ala Asp Tyr Tyr Cys Ala Ala Trp Asp Asp Ser Leu
              85                   90                 95

Asn Gly His Trp Val Phe Gly Gly Gly Thr Lys Leu Thr Val Leu
          100                 105               110

<210> SEQ ID NO 23
<211> LENGTH: 348
<212> TYPE: DNA
<213> ORGANISM: Human

<400> SEQUENCE: 23

| gag | gtg | cag | ctg | gtg | cag | tct | ggg | gga | ggc | ctg | gtc | aag | cct | ggg | ggg | 48 |
| Glu | Val | Gln | Leu | Val | Gln | Ser | Gly | Gly | Gly | Leu | Val | Lys | Pro | Gly | Gly | |
| | | | | 5 | | | | | 10 | | | | | 15 | | |

| tcc | ctg | aga | ctc | tcc | tgt | gca | gcc | tct | gga | ttc | acc | ttc | agt | agc | tat | 96 |
| Ser | Leu | Arg | Leu | Ser | Cys | Ala | Ala | Ser | Gly | Phe | Thr | Phe | Ser | Ser | Tyr | |
| | | | 20 | | | | | 25 | | | | | 30 | | | |

```
agc atg aac tgg gtc cgc cag gct cca ggg aag ggg ctg gag tgg gtc      144
Ser Met Asn Trp Val Arg Gln Ala Pro Gly Lys Gly Leu Glu Trp Val
        35                  40                  45 tca tcc att agt agt agt agt agt tac ata tac tac gca gac tca gtg      192
Ser Ser Ile Ser Ser Ser Ser Ser Tyr Ile Tyr Tyr Ala Asp Ser Val
 50                  55                  60 aag ggc cga ttc acc atc tcc aga gac aac gcc aag aac tca ctg tat      240
Lys Gly Arg Phe Thr Ile Ser Arg Asp Asn Ala Lys Asn Ser Leu Tyr
 65                  70                  75                  80 ctg caa atg aac agc ctg aga gcc gag gac acg gct gtg tat tac tgt      288
Leu Gln Met Asn Ser Leu Arg Ala Glu Asp Thr Ala Val Tyr Tyr Cys
                85                  90                  95 gcg aga gtc aca gat gct ttt gat atc tgg ggc caa ggg aca atg gtc      336
Ala Arg Val Thr Asp Ala Phe Asp Ile Trp Gly Gln Gly Thr Met Val
            100                 105                 110 acc gtc tca agc                                                      348
Thr Val Ser Ser
        115

<210> SEQ ID NO 24
<211> LENGTH: 116
<212> TYPE: PRT
<213> ORGANISM: Human

<400> SEQUENCE: 24

Glu Val Gln Leu Val Gln Ser Gly Gly Gly Leu Val Lys Pro Gly Gly
                 5                  10                  15

Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Val Thr Asp Ala Phe Asp Ile Trp Gly Gln Gly Thr Met Val
            100                 105                 110

Thr Val Ser Ser
        115

<210> SEQ ID NO 25
<211> LENGTH: 321
<212> TYPE: DNA
<213> ORGANISM: Human

<400> SEQUENCE: 25 gaa att gtg atg aca cag tct cca gcc acc ctg tct ttg tct cca ggg       48
Glu Ile Val Met Thr Gln Ser Pro Ala Thr Leu Ser Leu Ser Pro Gly
                 5                  10                  15 gaa aga gcc acc ctc tcc tgc agg gcc agt cag agt gtt agc agc tac       96
Glu Arg Ala Thr Leu Ser Cys Arg Ala Ser Gln Ser Val Ser Ser Tyr
                20                  25                  30 tta gcc tgg tac caa cag aaa cct ggc cag gct ccc agg ctc ctc atc      144
Leu Ala Trp Tyr Gln Gln Lys Pro Gly Gln Ala Pro Arg Leu Leu Ile
        35                  40                  45 tat gat tca tcc aac agg gcc act ggc atc cca gcc agg ttc agt ggc      192
Tyr Asp Ser Ser Asn Arg Ala Thr Gly Ile Pro Ala Arg Phe Ser Gly
```

```
                50                    55                    60
agt ggg tct ggg aca gac ttc act ctc acc atc agc agc cta gag cct    240
Ser Gly Ser Gly Thr Asp Phe Thr Leu Thr Ile Ser Ser Leu Glu Pro
 65                  70                  75                  80 gaa gat ttt gca act tat tac tgt cta cag cat aac act ttt cct ccg    288
Glu Asp Phe Ala Thr Tyr Tyr Cys Leu Gln His Asn Thr Phe Pro Pro
                 85                  90                  95 acg ttc ggc caa ggg acc aag gtg gaa atc aaa                        321
Thr Phe Gly Gln Gly Thr Lys Val Glu Ile Lys
            100                 105

<210> SEQ ID NO 26
<211> LENGTH: 107
<212> TYPE: PRT
<213> ORGANISM: Human

<400> SEQUENCE: 26

Glu Ile Val Met Thr Gln Ser Pro Ala Thr Leu Ser Leu Ser Pro Gly
                  5                  10                  15

Glu Arg Ala Thr Leu Ser Cys Arg Ala Ser Gln Ser Val Ser Ser Tyr
             20                  25                  30

Leu Ala Trp Tyr Gln Gln Lys Pro Gly Gln Ala Pro Arg Leu Leu Ile
         35                  40                  45

Tyr Asp Ser Ser Asn Arg Ala Thr Gly Ile Pro Ala Arg Phe Ser Gly
     50                  55                  60

Ser Gly Ser Gly Thr Asp Phe Thr Leu Thr Ile Ser Ser Leu Glu Pro
 65                  70                  75                  80

Glu Asp Phe Ala Thr Tyr Tyr Cys Leu Gln His Asn Thr Phe Pro Pro
                 85                  90                  95

Thr Phe Gly Gln Gly Thr Lys Val Glu Ile Lys
            100                 105

<210> SEQ ID NO 27
<211> LENGTH: 348
<212> TYPE: DNA
<213> ORGANISM: Human

<400> SEQUENCE: 27 gag gtc cag ctg gtg cag tct ggg gga ggc ctg gtc aag cct ggg ggg     48
Glu Val Gln Leu Val Gln Ser Gly Gly Gly Leu Val Lys Pro Gly Gly
                  5                  10                  15 tcc ctg aga ctc tcc tgt gca gcc tct gga ttc acc ttc agt agc tat     96
Ser Leu Arg Leu Ser Cys Ala Ala Ser Gly Phe Thr Phe Ser Ser Tyr
             20                  25                  30 agc atg aac tgg gtc cgc cag gct cca ggg aag ggg ctg gag tgg gtc    144
Ser Met Asn Trp Val Arg Gln Ala Pro Gly Lys Gly Leu Glu Trp Val
         35                  40                  45 tca tcc att agt agt agt agt agt tac ata tac tac gca gac tca gtg    192
Ser Ser Ile Ser Ser Ser Ser Ser Tyr Ile Tyr Tyr Ala Asp Ser Val
     50                  55                  60 aag ggc cga ttc acc atc tcc aga gac aac gcc aag aac tca ctg tat    240
Lys Gly Arg Phe Thr Ile Ser Arg Asp Asn Ala Lys Asn Ser Leu Tyr
 65                  70                  75                  80 ctg caa atg aac agc ctg aga gcc gag gac acg gct gtg tat tac tgt    288
Leu Gln Met Asn Ser Leu Arg Ala Glu Asp Thr Ala Val Tyr Tyr Cys
                 85                  90                  95 gcg aga gtc aca gat gct ttt gat atc tgg ggc caa ggg aca atg gtc    336
Ala Arg Val Thr Asp Ala Phe Asp Ile Trp Gly Gln Gly Thr Met Val
            100                 105                 110
```

```
                                                    -continued
acc gtc tca agc                                          348
Thr Val Ser Ser
        115

<210> SEQ ID NO 28
<211> LENGTH: 330
<212> TYPE: DNA
<213> ORGANISM: Human

<400> SEQUENCE: 28 cag tct gcc ctg act cag cct gcc tcc ctg tct ggg tct cct gga cag     48
Gln Ser Ala Leu Thr Gln Pro Ala Ser Leu Ser Gly Ser Pro Gly Gln
                 5                  10                  15 tcg atc acc atc tcc tgc gct gga acc acc act gat ctt aca tat tat     96
Ser Ile Thr Ile Ser Cys Ala Gly Thr Thr Thr Asp Leu Thr Tyr Tyr
             20                  25                  30 gac ctt gtc tcc tgg tac caa cag cac cca ggc caa gca ccc aaa ctc    144
Asp Leu Val Ser Trp Tyr Gln Gln His Pro Gly Gln Ala Pro Lys Leu
         35                  40                  45 gtg att tat gac ggc aat aag cgg ccc tca gga gtt tct aat cgc ttc    192
Val Ile Tyr Asp Gly Asn Lys Arg Pro Ser Gly Val Ser Asn Arg Phe
     50                  55                  60 tct ggc tcc aag tct ggc aac acg gcc tcc ctg aca atc tct gga ctc    240
Ser Gly Ser Lys Ser Gly Asn Thr Ala Ser Leu Thr Ile Ser Gly Leu
 65                  70                  75                  80 cag gct gag gac gag gct gat tat tac tgc aac tca tat gta agc agc    288
Gln Ala Glu Asp Glu Ala Asp Tyr Tyr Cys Asn Ser Tyr Val Ser Ser
                 85                  90                  95 agg ttt tat gtc ttc gga act ggg acc aag gtc acc gtc cta             330
Arg Phe Tyr Val Phe Gly Thr Gly Thr Lys Val Thr Val Leu
            100                 105                 110

<210> SEQ ID NO 29
<211> LENGTH: 110
<212> TYPE: PRT
<213> ORGANISM: Human

<400> SEQUENCE: 29

Gln Ser Ala Leu Thr Gln Pro Ala Ser Leu Ser Gly Ser Pro Gly Gln
                 5                  10                  15

Ser Ile Thr Ile Ser Cys Ala Gly Thr Thr Thr Asp Leu Thr Tyr Tyr
             20                  25                  30

Asp Leu Val Ser Trp Tyr Gln Gln His Pro Gly Gln Ala Pro Lys Leu
         35                  40                  45

Val Ile Tyr Asp Gly Asn Lys Arg Pro Ser Gly Val Ser Asn Arg Phe
     50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Asn Ser Tyr Val Ser Ser
                 85                  90                  95

Arg Phe Tyr Val Phe Gly Thr Gly Thr Lys Val Thr Val Leu
            100                 105                 110

<210> SEQ ID NO 30
<211> LENGTH: 348
<212> TYPE: DNA
<213> ORGANISM: Human

<400> SEQUENCE: 30 gaa gtg cag ctg gtg cag tct ggg gga ggc ctg gtc aag cct ggg ggg     48
Glu Val Gln Leu Val Gln Ser Gly Gly Gly Leu Val Lys Pro Gly Gly
```

-continued

```
            5                   10                  15
tcc ctg aga ctc tcc tgt gca gcc tct gga ttc acc ttc agt agc tat      96
Ser Leu Arg Leu Ser Cys Ala Ala Ser Gly Phe Thr Phe Ser Ser Tyr
            20                  25                  30 agc atg aac tgg gtc cgc cag gct cca ggg aag ggg ctg gag tgg gtc     144
Ser Met Asn Trp Val Arg Gln Ala Pro Gly Lys Gly Leu Glu Trp Val
        35                  40                  45 tca tcc att agt agt agt agt agt tac ata tac tac gca gac tca gtg     192
Ser Ser Ile Ser Ser Ser Ser Ser Tyr Ile Tyr Tyr Ala Asp Ser Val
    50                  55                  60 aag ggc cga ttc acc atc tcc aga gac aac gcc aag gac tca ctg tat     240
Lys Gly Arg Phe Thr Ile Ser Arg Asp Asn Ala Lys Asp Ser Leu Tyr
65                  70                  75                  80 ctg caa atg aac agc ctg aga gcc gag gac acg gct gtg tat tac tgt     288
Leu Gln Met Asn Ser Leu Arg Ala Glu Asp Thr Ala Val Tyr Tyr Cys
                85                  90                  95 gcg aga gtc aca gat gct ttt gat atc tgg ggc caa ggg aca atg gtc    336
Ala Arg Val Thr Asp Ala Phe Asp Ile Trp Gly Gln Gly Thr Met Val
                100                 105                 110 acc gtc tca agc                                                     348
Thr Val Ser Ser
        115

<210> SEQ ID NO 31
<211> LENGTH: 116
<212> TYPE: PRT
<213> ORGANISM: Human

<400> SEQUENCE: 31

Glu Val Gln Leu Val Gln Ser Gly Gly Gly Leu Val Lys Pro Gly Gly
                5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asp Ser Leu Tyr
65                  70                  75                  80

Leu Gln Met Asn Ser Leu Arg Ala Glu Asp Thr Ala Val Tyr Tyr Cys
                85                  90                  95

Ala Arg Val Thr Asp Ala Phe Asp Ile Trp Gly Gln Gly Thr Met Val
                100                 105                 110

Thr Val Ser Ser
        115

<210> SEQ ID NO 32
<211> LENGTH: 321
<212> TYPE: DNA
<213> ORGANISM: Human

<400> SEQUENCE: 32 gac atc cag ttg acc cag tct cca tct tct gtg tct gca tct gta gga      48
Asp Ile Gln Leu Thr Gln Ser Pro Ser Ser Val Ser Ala Ser Val Gly
                5                   10                  15 gac aga gtc acc atc act tgt cgg gcg agt cag ggt att agt agc cgg      96
Asp Arg Val Thr Ile Thr Cys Arg Ala Ser Gln Gly Ile Ser Ser Arg
            20                  25                  30 tta gcc tgg tat cag cag aaa cca ggg aaa gcc cct aag ctc ctg atc     144
```

```
Leu Ala Trp Tyr Gln Gln Lys Pro Gly Lys Ala Pro Lys Leu Leu Ile
         35                  40                  45 tat gct gca tcc agt ttg caa act ggg gtc cca tca agg ttc agc ggc       192
Tyr Ala Ala Ser Ser Leu Gln Thr Gly Val Pro Ser Arg Phe Ser Gly
 50                  55                  60 agt gga tct ggg aca gat ttc act ctc act atc agc agc ctg cag cct       240
Ser Gly Ser Gly Thr Asp Phe Thr Leu Thr Ile Ser Ser Leu Gln Pro
65                  70                  75                  80 gaa gat ttt gca act tac tat tgt caa cag gct aac agg ttc cct ccg       288
Glu Asp Phe Ala Thr Tyr Tyr Cys Gln Gln Ala Asn Arg Phe Pro Pro
                 85                  90                  95 act ttc ggc cct ggg acc aaa gtg gat atc aaa                           321
Thr Phe Gly Pro Gly Thr Lys Val Asp Ile Lys
             100                 105

<210> SEQ ID NO 33
<211> LENGTH: 107
<212> TYPE: PRT
<213> ORGANISM: Human

<400> SEQUENCE: 33

Asp Ile Gln Leu Thr Gln Ser Pro Ser Ser Val Ser Ala Ser Val Gly
                 5                  10                  15

Asp Arg Val Thr Ile Thr Cys Arg Ala Ser Gln Gly Ile Ser Ser Arg
             20                  25                  30

Leu Ala Trp Tyr Gln Gln Lys Pro Gly Lys Ala Pro Lys Leu Leu Ile
         35                  40                  45

Tyr Ala Ala Ser Ser Leu Gln Thr Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Arg Phe Pro Pro
                 85                  90                  95

Thr Phe Gly Pro Gly Thr Lys Val Asp Ile Lys
             100                 105

<210> SEQ ID NO 34
<211> LENGTH: 333
<212> TYPE: DNA
<213> ORGANISM: Human

<400> SEQUENCE: 34 cag tct gtc gtg acg cag ccg ccc tca gtg tct ggg gcc cca ggg cag        48
Gln Ser Val Val Thr Gln Pro Pro Ser Val Ser Gly Ala Pro Gly Gln
                 5                  10                  15 agg gtc acc atc tcc tgc act ggg agc cac tcc aac ttc ggg gca gga        96
Arg Val Thr Ile Ser Cys Thr Gly Ser His Ser Asn Phe Gly Ala Gly
             20                  25                  30 act gat gta cat tgg tac caa cac ctt cca gga aca gcc ccc aga ctc       144
Thr Asp Val His Trp Tyr Gln His Leu Pro Gly Thr Ala Pro Arg Leu
         35                  40                  45 ctc att cat gga gac agt aat cgg ccc tcc ggg gtc cct gac cga ttc       192
Leu Ile His Gly Asp Ser Asn Arg Pro Ser Gly Val Pro Asp Arg Phe
 50                  55                  60 tct ggc tcc agg tct ggc acc tca gcc tcc ctg gcc atc act ggg ctc       240
Ser Gly Ser Arg Ser Gly Thr Ser Ala Ser Leu Ala Ile Thr Gly Leu
65                  70                  75                  80 cgg gtt gag gat gag gct gat tat tac tgt cag tcg tat gac tat ggc       288
Arg Val Glu Asp Glu Ala Asp Tyr Tyr Cys Gln Ser Tyr Asp Tyr Gly
                 85                  90                  95
```

```
ctg aga ggt tgg gtg ttc ggc ggc ggg acc aag ctg acc gtc ctt      333
Leu Arg Gly Trp Val Phe Gly Gly Gly Thr Lys Leu Thr Val Leu
        100                 105                 110

<210> SEQ ID NO 35
<211> LENGTH: 111
<212> TYPE: PRT
<213> ORGANISM: Human

<400> SEQUENCE: 35

Gln Ser Val Val Thr Gln Pro Pro Ser Val Ser Gly Ala Pro Gly Gln
                5                   10                  15

Arg Val Thr Ile Ser Cys Thr Gly Ser His Ser Asn Phe Gly Ala Gly
            20                  25                  30

Thr Asp Val His Trp Tyr Gln His Leu Pro Gly Thr Ala Pro Arg Leu
        35                  40                  45

Leu Ile His Gly Asp Ser Asn Arg Pro Ser Gly Val Pro Asp Arg Phe
    50                  55                  60

Ser Gly Ser Arg Ser Gly Thr Ser Ala Ser Leu Ala Ile Thr Gly Leu
65                  70                  75                  80

Arg Val Glu Asp Glu Ala Asp Tyr Tyr Cys Gln Ser Tyr Asp Tyr Gly
                85                  90                  95

Leu Arg Gly Trp Val Phe Gly Gly Gly Thr Lys Leu Thr Val Leu
            100                 105                 110

<210> SEQ ID NO 36
<211> LENGTH: 321
<212> TYPE: DNA
<213> ORGANISM: Human

<400> SEQUENCE: 36 gat gtt gtg atg act cag tct cca tcg tcc ctg tct gca tct gta ggg      48
Asp Val Val Met Thr Gln Ser Pro Ser Ser Leu Ser Ala Ser Val Gly
                5                   10                  15 gac aga gtc acc atc act tgc cgg gca agt cag aac att aac aac tat      96
Asp Arg Val Thr Ile Thr Cys Arg Ala Ser Gln Asn Ile Asn Asn Tyr
            20                  25                  30 tta aat tgg tat caa cag aaa cca gga aaa gcc cct aag ctc ctg atc     144
Leu Asn Trp Tyr Gln Gln Lys Pro Gly Lys Ala Pro Lys Leu Leu Ile
        35                  40                  45 tat gct gcc tcc act ttg caa agt ggg gtc cca tca agg ttc agt ggc     192
Tyr Ala Ala Ser Thr Leu Gln Ser Gly Val Pro Ser Arg Phe Ser Gly
    50                  55                  60 agt gga tct ggg aca gat ttc act ctc acc atc acc agc cta cag cct     240
Ser Gly Ser Gly Thr Asp Phe Thr Leu Thr Ile Thr Ser Leu Gln Pro
65                  70                  75                  80 gaa gat tct gca act tat tac tgc caa cag tat tcc cgt tat cct ccc     288
Glu Asp Ser Ala Thr Tyr Tyr Cys Gln Gln Tyr Ser Arg Tyr Pro Pro
                85                  90                  95 act ttc ggc gga ggg acc aag gtg gag atc aca                         321
Thr Phe Gly Gly Gly Thr Lys Val Glu Ile Thr
            100                 105

<210> SEQ ID NO 37
<211> LENGTH: 107
<212> TYPE: PRT
<213> ORGANISM: Human

<400> SEQUENCE: 37

Asp Val Val Met Thr Gln Ser Pro Ser Ser Leu Ser Ala Ser Val Gly
```

-continued

```
                  5                   10                  15
Asp Arg Val Thr Ile Thr Cys Arg Ala Ser Gln Asn Ile Asn Asn Tyr
                    20                  25                  30

Leu Asn Trp Tyr Gln Gln Lys Pro Gly Lys Ala Pro Lys Leu Leu Ile
                35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Thr Ser Leu Gln Pro
 65                  70                  75                  80

Glu Asp Ser Ala Thr Tyr Tyr Cys Gln Gln Tyr Ser Arg Tyr Pro Pro
                    85                  90                  95

Thr Phe Gly Gly Gly Thr Lys Val Glu Ile Thr
                100                 105

<210> SEQ ID NO 38
<211> LENGTH: 330
<212> TYPE: DNA
<213> ORGANISM: Human

<400> SEQUENCE: 38 cag tct gcc ctg act cag cct gcc tcc gtg tct ggg tct cgt gga cag    48
Gln Ser Ala Leu Thr Gln Pro Ala Ser Val Ser Gly Ser Arg Gly Gln
              5                   10                  15 tcg atc acc ctc tcc tgc acc ggc tcc agc act gat gtg ggt aat tat    96
Ser Ile Thr Leu Ser Cys Thr Gly Ser Ser Thr Asp Val Gly Asn Tyr
                20                  25                  30 aac tat atc tcc tgg tac caa caa cac cca ggc caa gcc ccc aaa ctc   144
Asn Tyr Ile Ser Trp Tyr Gln Gln His Pro Gly Gln Ala Pro Lys Leu
            35                  40                  45 ttg att tac gat gtc act agt cgg ccc tca ggt gtt tct gat cgc ttc   192
Leu Ile Tyr Asp Val Thr Ser Arg Pro Ser Gly Val Ser Asp Arg Phe
         50                  55                  60 tct ggc tcc aag tca ggc ctc acg gcc tcc ctg acc atc tct gga ctc   240
Ser Gly Ser Lys Ser Gly Leu Thr Ala Ser Leu Thr Ile Ser Gly Leu
 65                  70                  75                  80 cag cct gaa gac gag gct gac tat tac tgc aac tcc tat tct gcc acc   288
Gln Pro Glu Asp Glu Ala Asp Tyr Tyr Cys Asn Ser Tyr Ser Ala Thr
                    85                  90                  95 gac act ctt gtt ttt ggc gga ggg acc aag ctg acc gtc cta           330
Asp Thr Leu Val Phe Gly Gly Gly Thr Lys Leu Thr Val Leu
                100                 105                 110

<210> SEQ ID NO 39
<211> LENGTH: 110
<212> TYPE: PRT
<213> ORGANISM: Human

<400> SEQUENCE: 39

Gln Ser Ala Leu Thr Gln Pro Ala Ser Val Ser Gly Ser Arg Gly Gln
              5                   10                  15

Ser Ile Thr Leu Ser Cys Thr Gly Ser Ser Thr Asp Val Gly Asn Tyr
                20                  25                  30

Asn Tyr Ile Ser Trp Tyr Gln Gln His Pro Gly Gln Ala Pro Lys Leu
            35                  40                  45

Leu Ile Tyr Asp Val Thr Ser Arg Pro Ser Gly Val Ser Asp Arg Phe
         50                  55                  60

Ser Gly Ser Lys Ser Gly Leu Thr Ala Ser Leu Thr Ile Ser Gly Leu
 65                  70                  75                  80
```

```
Gln Pro Glu Asp Glu Ala Asp Tyr Tyr Cys Asn Ser Tyr Ser Ala Thr
                85                  90                  95

Asp Thr Leu Val Phe Gly Gly Gly Thr Lys Leu Thr Val Leu
            100                 105                 110

<210> SEQ ID NO 40
<211> LENGTH: 333
<212> TYPE: DNA
<213> ORGANISM: Human

<400> SEQUENCE: 40 cag gct gtg ctg act cag ccg tcc tca gtg tct ggg gcc cca gga cag      48
Gln Ala Val Leu Thr Gln Pro Ser Ser Val Ser Gly Ala Pro Gly Gln
            5                   10                  15 agg gtc acc atc tcc tgc act ggg caa agc tcc aat atc ggg gca gat      96
Arg Val Thr Ile Ser Cys Thr Gly Gln Ser Ser Asn Ile Gly Ala Asp
        20                  25                  30 tat gat gta cat tgg tac cag caa ttt cca gga aca gcc ccc aaa ctc     144
Tyr Asp Val His Trp Tyr Gln Gln Phe Pro Gly Thr Ala Pro Lys Leu
    35                  40                  45 ctc atc tat ggt cac aac aat cgg ccc tca ggg gtc cct gac cga ttc     192
Leu Ile Tyr Gly His Asn Asn Arg Pro Ser Gly Val Pro Asp Arg Phe
50                  55                  60 tct ggc tcc aag tct ggc acc tca gtc tcc ctg gtc atc agt ggg ctc     240
Ser Gly Ser Lys Ser Gly Thr Ser Val Ser Leu Val Ile Ser Gly Leu
65                  70                  75                  80 cag gct gag gat gag gct gat tat tat tgc cag tcc tat gac agc agt     288
Gln Ala Glu Asp Glu Ala Asp Tyr Tyr Cys Gln Ser Tyr Asp Ser Ser
                85                  90                  95 cta agt ggt ttg gta ttc ggc gga ggg acc aag gtg acc gtc cta         333
Leu Ser Gly Leu Val Phe Gly Gly Gly Thr Lys Val Thr Val Leu
            100                 105                 110

<210> SEQ ID NO 41
<211> LENGTH: 111
<212> TYPE: PRT
<213> ORGANISM: Human

<400> SEQUENCE: 41

Gln Ala Val Leu Thr Gln Pro Ser Ser Val Ser Gly Ala Pro Gly Gln
            5                   10                  15

Arg Val Thr Ile Ser Cys Thr Gly Gln Ser Ser Asn Ile Gly Ala Asp
        20                  25                  30

Tyr Asp Val His Trp Tyr Gln Gln Phe Pro Gly Thr Ala Pro Lys Leu
    35                  40                  45

Leu Ile Tyr Gly His Asn Asn Arg Pro Ser Gly Val Pro Asp Arg Phe
50                  55                  60

Ser Gly Ser Lys Ser Gly Thr Ser Val Ser Leu Val Ile Ser Gly Leu
65                  70                  75                  80

Gln Ala Glu Asp Glu Ala Asp Tyr Tyr Cys Gln Ser Tyr Asp Ser Ser
                85                  90                  95

Leu Ser Gly Leu Val Phe Gly Gly Gly Thr Lys Val Thr Val Leu
            100                 105                 110

<210> SEQ ID NO 42
<211> LENGTH: 321
<212> TYPE: DNA
<213> ORGANISM: Human

<400> SEQUENCE: 42
```

```
gac atc cag ttg acc cag tct cca tct tct gtg tct gca tct gtt gga        48
Asp Ile Gln Leu Thr Gln Ser Pro Ser Ser Val Ser Ala Ser Val Gly
                 5                  10                  15 gac agc gtc acc atc act tgt cgg gcg agt cag gat att agc agc tgg        96
Asp Ser Val Thr Ile Thr Cys Arg Ala Ser Gln Asp Ile Ser Ser Trp
             20                  25                  30 tta gcc tgg tat caa cag aaa cca ggg gag gcc cct aag ctc ctg atc       144
Leu Ala Trp Tyr Gln Gln Lys Pro Gly Glu Ala Pro Lys Leu Leu Ile
         35                  40                  45 tat gct gca tcc ctt ctt caa agt ggg gtc cca tca cgg ttc agc ggc       192
Tyr Ala Ala Ser Leu Leu Gln Ser Gly Val Pro Ser Arg Phe Ser Gly
     50                  55                  60 agt gga tct ggg aca gat ttc gct ctc act atc aac agc ctg cag cct       240
Ser Gly Ser Gly Thr Asp Phe Ala Leu Thr Ile Asn Ser Leu Gln Pro
 65                  70                  75                  80 gaa gat ttt gca act tac ttt tgt caa cag gct gac agt ttc cct ccc       288
Glu Asp Phe Ala Thr Tyr Phe Cys Gln Gln Ala Asp Ser Phe Pro Pro
                 85                  90                  95 acc ttc ggc caa ggg aca cgg ctg gag att aaa                           321
Thr Phe Gly Gln Gly Thr Arg Leu Glu Ile Lys
             100                 105

<210> SEQ ID NO 43
<211> LENGTH: 107
<212> TYPE: PRT
<213> ORGANISM: Human

<400> SEQUENCE: 43

Asp Ile Gln Leu Thr Gln Ser Pro Ser Ser Val Ser Ala Ser Val Gly
                 5                  10                  15

Asp Ser Val Thr Ile Thr Cys Arg Ala Ser Gln Asp Ile Ser Ser Trp
             20                  25                  30

Leu Ala Trp Tyr Gln Gln Lys Pro Gly Glu Ala Pro Lys Leu Leu Ile
         35                  40                  45

Tyr Ala Ala Ser Leu Leu Gln Ser Gly Val Pro Ser Arg Phe Ser Gly
     50                  55                  60

Ser Gly Ser Gly Thr Asp Phe Ala Leu Thr Ile Asn Ser Leu Gln Pro
 65                  70                  75                  80

Glu Asp Phe Ala Thr Tyr Phe Cys Gln Gln Ala Asp Ser Phe Pro Pro
                 85                  90                  95

Thr Phe Gly Gln Gly Thr Arg Leu Glu Ile Lys
             100                 105

<210> SEQ ID NO 44
<211> LENGTH: 321
<212> TYPE: DNA
<213> ORGANISM: Human

<400> SEQUENCE: 44 gac atc gag ttg acc cag tct cca tct tcc gtg tct gca tct gtg gga        48
Asp Ile Glu Leu Thr Gln Ser Pro Ser Ser Val Ser Ala Ser Val Gly
                 5                  10                  15 gac aga gtc acc ctc act tgt cgg gcg agt cag agt att aag agg tgg        96
Asp Arg Val Thr Leu Thr Cys Arg Ala Ser Gln Ser Ile Lys Arg Trp
             20                  25                  30 tta gcc tgg tat cag cag aaa cca ggg aag gcc cct agg ctc ctc atc       144
Leu Ala Trp Tyr Gln Gln Lys Pro Gly Lys Ala Pro Arg Leu Leu Ile
         35                  40                  45 tat gct gca tcc act ttg caa agt ggg gtc cca tca agg ttc agc ggc       192
Tyr Ala Ala Ser Thr Leu Gln Ser Gly Val Pro Ser Arg Phe Ser Gly
```

-continued

```
                  50                  55                  60
ggt gga tct ggg aca gat ttc act ctc acc atc aac agc ctg cag cct    240
Gly Gly Ser Gly Thr Asp Phe Thr Leu Thr Ile Asn Ser Leu Gln Pro
 65                  70                  75                  80 gaa gat ttt gca att tac tac tgt caa cag gct aac agt ttc cct ccc    288
Glu Asp Phe Ala Ile Tyr Tyr Cys Gln Gln Ala Asn Ser Phe Pro Pro
                 85                  90                  95 act ttc ggc cct ggg acc aaa gtg gat atc aaa                        321
Thr Phe Gly Pro Gly Thr Lys Val Asp Ile Lys
            100                 105

<210> SEQ ID NO 45
<211> LENGTH: 107
<212> TYPE: PRT
<213> ORGANISM: Human

<400> SEQUENCE: 45

Asp Ile Glu Leu Thr Gln Ser Pro Ser Ser Val Ser Ala Ser Val Gly
                  5                  10                  15

Asp Arg Val Thr Leu Thr Cys Arg Ala Ser Gln Ser Ile Lys Arg Trp
             20                  25                  30

Leu Ala Trp Tyr Gln Gln Lys Pro Gly Lys Ala Pro Arg Leu Leu Ile
         35                  40                  45

Tyr Ala Ala Ser Thr Leu Gln Ser Gly Val Pro Ser Arg Phe Ser Gly
     50                  55                  60

Gly Gly Ser Gly Thr Asp Phe Thr Leu Thr Ile Asn Ser Leu Gln Pro
 65                  70                  75                  80

Glu Asp Phe Ala Ile Tyr Tyr Cys Gln Gln Ala Asn Ser Phe Pro Pro
                 85                  90                  95

Thr Phe Gly Pro Gly Thr Lys Val Asp Ile Lys
            100                 105

<210> SEQ ID NO 46
<211> LENGTH: 333
<212> TYPE: DNA
<213> ORGANISM: Human

<400> SEQUENCE: 46 cag tct gtc gtg acg cag ccg ccc tca gtg tct ggg gcc cca ggg cag     48
Gln Ser Val Val Thr Gln Pro Pro Ser Val Ser Gly Ala Pro Gly Gln
                  5                  10                  15 agg gtc acc atc tcc tgc agt ggg agc agg tcc aac atc ggg gca cac     96
Arg Val Thr Ile Ser Cys Ser Gly Ser Arg Ser Asn Ile Gly Ala His
             20                  25                  30 tat gaa gtc cag tgg tac cag cag ttt ccg gga gca gcc ccc aaa ctc    144
Tyr Glu Val Gln Trp Tyr Gln Gln Phe Pro Gly Ala Ala Pro Lys Leu
         35                  40                  45 ctc atc tat ggt gac acc aat cgg ccc tca ggg gtc cct gac cga ttc    192
Leu Ile Tyr Gly Asp Thr Asn Arg Pro Ser Gly Val Pro Asp Arg Phe
     50                  55                  60 tct gcc tcc cac tct ggc acc tca gcc tcc ctt gcc atc aca ggg ctc    240
Ser Ala Ser His Ser Gly Thr Ser Ala Ser Leu Ala Ile Thr Gly Leu
 65                  70                  75                  80 cag gct gag gat gag gct gat tat tac tgc cag tcg tat gac acc agt    288
Gln Ala Glu Asp Glu Ala Asp Tyr Tyr Cys Gln Ser Tyr Asp Thr Ser
                 85                  90                  95 cta cgt ggt ccg gtg ttc ggc gga ggg acc aag ctg acc gtc cta        333
Leu Arg Gly Pro Val Phe Gly Gly Gly Thr Lys Leu Thr Val Leu
            100                 105                 110
```

```
<210> SEQ ID NO 47
<211> LENGTH: 111
<212> TYPE: PRT
<213> ORGANISM: Human

<400> SEQUENCE: 47

Gln Ser Val Val Thr Gln Pro Pro Ser Val Ser Gly Ala Pro Gly Gln
                5                   10                  15

Arg Val Thr Ile Ser Cys Ser Gly Ser Arg Ser Asn Ile Gly Ala His
            20                  25                  30

Tyr Glu Val Gln Trp Tyr Gln Gln Phe Pro Gly Ala Ala Pro Lys Leu
        35                  40                  45

Leu Ile Tyr Gly Asp Thr Asn Arg Pro Ser Gly Val Pro Asp Arg Phe
    50                  55                  60

Ser Ala Ser His Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Thr Ser
                85                  90                  95

Leu Arg Gly Pro Val Phe Gly Gly Gly Thr Lys Leu Thr Val Leu
            100                 105                 110

<210> SEQ ID NO 48
<211> LENGTH: 333
<212> TYPE: DNA
<213> ORGANISM: Human

<400> SEQUENCE: 48 cag tct gtc gtg acg cag ccg ccc tca gtg tct ggg gcc cca ggg cag      48
Gln Ser Val Val Thr Gln Pro Pro Ser Val Ser Gly Ala Pro Gly Gln
                5                   10                  15 agg gtc acc atc tcc tgc act ggg agc agc tcc aac atc ggg aca ggt      96
Arg Val Thr Ile Ser Cys Thr Gly Ser Ser Ser Asn Ile Gly Thr Gly
            20                  25                  30 tat gat gta cat tgg tac cag cag gtt cca gga tca gcc ccc aaa ctc     144
Tyr Asp Val His Trp Tyr Gln Gln Val Pro Gly Ser Ala Pro Lys Leu
        35                  40                  45 ctc atc tat gct tac acc aat cgg ccc tca ggg gtc cct gac cga ttc     192
Leu Ile Tyr Ala Tyr Thr Asn Arg Pro Ser Gly Val Pro Asp Arg Phe
    50                  55                  60 tct ggc tcc aag tct ggc atg tca gcc tcc ctg gtc atc ggt ggt ctc     240
Ser Gly Ser Lys Ser Gly Met Ser Ala Ser Leu Val Ile Gly Gly Leu
65                  70                  75                  80 cag gct gag gat gag gct gat tat tac tgc cag tcc ttt gac gac agc     288
Gln Ala Glu Asp Glu Ala Asp Tyr Tyr Cys Gln Ser Phe Asp Asp Ser
                85                  90                  95 ctg aat ggt ctt gtc ttc gga cct ggg acc tcg gtc acc gtc ctc         333
Leu Asn Gly Leu Val Phe Gly Pro Gly Thr Ser Val Thr Val Leu
            100                 105                 110

<210> SEQ ID NO 49
<211> LENGTH: 111
<212> TYPE: PRT
<213> ORGANISM: Human

<400> SEQUENCE: 49

Gln Ser Val Val Thr Gln Pro Pro Ser Val Ser Gly Ala Pro Gly Gln
                5                   10                  15

Arg Val Thr Ile Ser Cys Thr Gly Ser Ser Ser Asn Ile Gly Thr Gly
            20                  25                  30
```

```
Tyr Asp Val His Trp Tyr Gln Gln Val Pro Gly Ser Ala Pro Lys Leu
         35                  40                  45

Leu Ile Tyr Ala Tyr Thr Asn Arg Pro Ser Gly Val Pro Asp Arg Phe
     50                  55                  60

Ser Gly Ser Lys Ser Gly Met Ser Ala Ser Leu Val Ile Gly Gly Leu
 65                  70                  75                  80

Gln Ala Glu Asp Glu Ala Asp Tyr Tyr Cys Gln Ser Phe Asp Asp Ser
             85                  90                  95

Leu Asn Gly Leu Val Phe Gly Pro Gly Thr Ser Val Thr Val Leu
            100                 105                 110

<210> SEQ ID NO 50
<211> LENGTH: 333
<212> TYPE: DNA
<213> ORGANISM: Human

<400> SEQUENCE: 50
```

| | | | | | | | | | | | | | | | | |
|---|---|---|---|---|---|---|---|---|---|---|---|---|---|---|---|---|
| cag | tct | gtg | ttg | acg | cag | ccg | ccc | tca | gtg | tct | ggg | gcc | cca | ggg | cag | 48 |
| Gln | Ser | Val | Leu | Thr | Gln | Pro | Pro | Ser | Val | Ser | Gly | Ala | Pro | Gly | Gln | |
| | | | | 5 | | | | | 10 | | | | | 15 | | |
| agg | gtc | acc | atc | tcc | tgc | act | ggg | agc | cac | tcc | aac | ttc | ggg | gca | ggt | 96 |
| Arg | Val | Thr | Ile | Ser | Cys | Thr | Gly | Ser | His | Ser | Asn | Phe | Gly | Ala | Gly | |
| | | | 20 | | | | | 25 | | | | | 30 | | | |
| act | gat | gtc | cat | tgg | tac | caa | cac | ctt | cca | gga | aca | gcc | ccc | aga | ctc | 144 |
| Thr | Asp | Val | His | Trp | Tyr | Gln | His | Leu | Pro | Gly | Thr | Ala | Pro | Arg | Leu | |
| | | 35 | | | | | 40 | | | | | 45 | | | | |
| ctc | att | cat | gga | gac | act | cat | cgg | ccc | tcc | ggg | gtc | gct | gac | cga | ttc | 192 |
| Leu | Ile | His | Gly | Asp | Thr | His | Arg | Pro | Ser | Gly | Val | Ala | Asp | Arg | Phe | |
| | 50 | | | | | 55 | | | | | 60 | | | | | |
| tct | ggc | tcc | agg | tct | ggc | gcc | tca | gcc | tcc | ctg | gcc | atc | act | ggg | ctc | 240 |
| Ser | Gly | Ser | Arg | Ser | Gly | Ala | Ser | Ala | Ser | Leu | Ala | Ile | Thr | Gly | Leu | |
| 65 | | | | | 70 | | | | | 75 | | | | | 80 | |
| cgg | gtt | gag | gat | gag | gct | gat | tat | tac | tgt | cag | tcg | tat | gac | tat | ggc | 288 |
| Arg | Val | Glu | Asp | Glu | Ala | Asp | Tyr | Tyr | Cys | Gln | Ser | Tyr | Asp | Tyr | Gly | |
| | | | | 85 | | | | | 90 | | | | | 95 | | |
| ctg | aga | ggt | tgg | gtg | ttc | ggc | ggc | ggg | acc | aag | ctg | acc | gtc | ctt | | 333 |
| Leu | Arg | Gly | Trp | Val | Phe | Gly | Gly | Gly | Thr | Lys | Leu | Thr | Val | Leu | | |
| | | | 100 | | | | | 105 | | | | | 110 | | | |

```
<210> SEQ ID NO 51
<211> LENGTH: 111
<212> TYPE: PRT
<213> ORGANISM: Human

<400> SEQUENCE: 51

Gln Ser Val Leu Thr Gln Pro Pro Ser Val Ser Gly Ala Pro Gly Gln
              5                  10                  15

Arg Val Thr Ile Ser Cys Thr Gly Ser His Ser Asn Phe Gly Ala Gly
         20                  25                  30

Thr Asp Val His Trp Tyr Gln His Leu Pro Gly Thr Ala Pro Arg Leu
     35                  40                  45

Leu Ile His Gly Asp Thr His Arg Pro Ser Gly Val Ala Asp Arg Phe
 50                  55                  60

Ser Gly Ser Arg Ser Gly Ala Ser Ala Ser Leu Ala Ile Thr Gly Leu
65                  70                  75                  80

Arg Val Glu Asp Glu Ala Asp Tyr Tyr Cys Gln Ser Tyr Asp Tyr Gly
             85                  90                  95

Leu Arg Gly Trp Val Phe Gly Gly Gly Thr Lys Leu Thr Val Leu
            100                 105                 110
```

<210> SEQ ID NO 52
<211> LENGTH: 321
<212> TYPE: DNA
<213> ORGANISM: Human

<400> SEQUENCE: 52

```
gac atc cag atg acc cag tct cca tct tcc gtg tct gca tct ata gga      48
Asp Ile Gln Met Thr Gln Ser Pro Ser Ser Val Ser Ala Ser Ile Gly
              5                  10                  15 gac aga gtc acc atc act tgt cgg gcg agt cag ggt att gac aac tgg      96
Asp Arg Val Thr Ile Thr Cys Arg Ala Ser Gln Gly Ile Asp Asn Trp
         20                  25                  30 tta ggc tgg tat cag cag aaa cct ggg aaa gcc cct aaa ctc ctg atc     144
Leu Gly Trp Tyr Gln Gln Lys Pro Gly Lys Ala Pro Lys Leu Leu Ile
     35                  40                  45 tac gat gca tcc aat ttg gac aca ggg gtc cca tca agg ttc agt gga     192
Tyr Asp Ala Ser Asn Leu Asp Thr Gly Val Pro Ser Arg Phe Ser Gly
 50                  55                  60 agt gga tct ggg aca tat ttt act ctc acc atc agt agc ctg caa gct     240
Ser Gly Ser Gly Thr Tyr Phe Thr Leu Thr Ile Ser Ser Leu Gln Ala
 65                  70                  75                  80 gaa gat ttt gca gtt tat ttc tgt caa cag gct aaa gct ttt cct ccc     288
Glu Asp Phe Ala Val Tyr Phe Cys Gln Gln Ala Lys Ala Phe Pro Pro
                 85                  90                  95 act ttc ggc gga ggg acc aag gtg gac atc aaa                         321
Thr Phe Gly Gly Gly Thr Lys Val Asp Ile Lys
            100                 105
```

<210> SEQ ID NO 53
<211> LENGTH: 107
<212> TYPE: PRT
<213> ORGANISM: Human

<400> SEQUENCE: 53

```
Asp Ile Gln Met Thr Gln Ser Pro Ser Ser Val Ser Ala Ser Ile Gly
              5                  10                  15

Asp Arg Val Thr Ile Thr Cys Arg Ala Ser Gln Gly Ile Asp Asn Trp
         20                  25                  30

Leu Gly Trp Tyr Gln Gln Lys Pro Gly Lys Ala Pro Lys Leu Leu Ile
     35                  40                  45

Tyr Asp Ala Ser Asn Leu Asp Thr Gly Val Pro Ser Arg Phe Ser Gly
 50                  55                  60

Ser Gly Ser Gly Thr Tyr Phe Thr Leu Thr Ile Ser Ser Leu Gln Ala
 65                  70                  75                  80

Glu Asp Phe Ala Val Tyr Phe Cys Gln Gln Ala Lys Ala Phe Pro Pro
                 85                  90                  95

Thr Phe Gly Gly Gly Thr Lys Val Asp Ile Lys
            100                 105
```

<210> SEQ ID NO 54
<211> LENGTH: 13
<212> TYPE: PRT
<213> ORGANISM: Human

<400> SEQUENCE: 54

```
Thr Gly Ser His Ser Asn Phe Gly Ala Gly Thr Asp Val
              5                  10
```

<210> SEQ ID NO 55

```
<211> LENGTH: 7
<212> TYPE: PRT
<213> ORGANISM: Human

<400> SEQUENCE: 55

Gly Asp Ser Asn Arg Pro Ser
                5

<210> SEQ ID NO 56
<211> LENGTH: 11
<212> TYPE: PRT
<213> ORGANISM: Human

<400> SEQUENCE: 56

Gln Ser Tyr Asp Tyr Gly Leu Arg Gly Trp Val
                5                  10

<210> SEQ ID NO 57
<211> LENGTH: 11
<212> TYPE: PRT
<213> ORGANISM: Human

<400> SEQUENCE: 57

Arg Ala Ser Gln Asn Ile Asn Asn Tyr Leu Asn
                5                  10

<210> SEQ ID NO 58
<211> LENGTH: 7
<212> TYPE: PRT
<213> ORGANISM: Human

<400> SEQUENCE: 58

Ala Ala Ser Thr Leu Gln Ser
                5

<210> SEQ ID NO 59
<211> LENGTH: 9
<212> TYPE: PRT
<213> ORGANISM: Human

<400> SEQUENCE: 59

Gln Gln Tyr Ser Arg Tyr Pro Pro Thr
                5

<210> SEQ ID NO 60
<211> LENGTH: 14
<212> TYPE: PRT
<213> ORGANISM: Human

<400> SEQUENCE: 60

Thr Gly Ser Ser Thr Asp Val Gly Asn Tyr Asn Tyr Ile Ser
                5                  10

<210> SEQ ID NO 61
<211> LENGTH: 7
<212> TYPE: PRT
<213> ORGANISM: Human

<400> SEQUENCE: 61

Asp Val Thr Ser Arg Pro Ser
                5

<210> SEQ ID NO 62
<211> LENGTH: 10
<212> TYPE: PRT
```

<213> ORGANISM: Human

<400> SEQUENCE: 62

Asn Ser Tyr Ser Ala Thr Asp Thr Leu Val
                 5                   10

<210> SEQ ID NO 63
<211> LENGTH: 14
<212> TYPE: PRT
<213> ORGANISM: Human

<400> SEQUENCE: 63

Thr Gly Gln Ser Ser Asn Ile Gly Ala Asp Tyr Asp Val His
                 5                   10

<210> SEQ ID NO 64
<211> LENGTH: 7
<212> TYPE: PRT
<213> ORGANISM: Human

<400> SEQUENCE: 64

Gly His Asn Asn Arg Pro Ser
                 5

<210> SEQ ID NO 65
<211> LENGTH: 11
<212> TYPE: PRT
<213> ORGANISM: Human

<400> SEQUENCE: 65

Gln Ser Tyr Asp Ser Ser Leu Ser Gly Leu Val
                 5                   10

<210> SEQ ID NO 66
<211> LENGTH: 11
<212> TYPE: PRT
<213> ORGANISM: Human

<400> SEQUENCE: 66

Arg Ala Ser Gln Asp Ile Ser Ser Trp Leu Ala
                 5                   10

<210> SEQ ID NO 67
<211> LENGTH: 7
<212> TYPE: PRT
<213> ORGANISM: Human

<400> SEQUENCE: 67

Ala Ala Ser Leu Leu Gln Ser
                 5

<210> SEQ ID NO 68
<211> LENGTH: 9
<212> TYPE: PRT
<213> ORGANISM: Human

<400> SEQUENCE: 68

Gln Gln Ala Asp Ser Phe Pro Pro Thr
                 5

<210> SEQ ID NO 69
<211> LENGTH: 11
<212> TYPE: PRT
<213> ORGANISM: Human

<400> SEQUENCE: 69

Arg Ala Ser Gln Ser Ile Lys Arg Trp Leu Ala
                 5                   10

<210> SEQ ID NO 70
<211> LENGTH: 7
<212> TYPE: PRT
<213> ORGANISM: Human

<400> SEQUENCE: 70

Ala Ala Ser Thr Leu Gln Ser
                 5

<210> SEQ ID NO 71
<211> LENGTH: 9
<212> TYPE: PRT
<213> ORGANISM: Human

<400> SEQUENCE: 71

Gln Gln Ala Asn Ser Phe Pro Pro Thr
                 5

<210> SEQ ID NO 72
<211> LENGTH: 14
<212> TYPE: PRT
<213> ORGANISM: Human

<400> SEQUENCE: 72

Ser Gly Ser Arg Ser Asn Ile Gly Ala His Tyr Glu Val Gln
                 5                   10

<210> SEQ ID NO 73
<211> LENGTH: 7
<212> TYPE: PRT
<213> ORGANISM: Human

<400> SEQUENCE: 73

Gly Asp Thr Asn Arg Pro Ser
                 5

<210> SEQ ID NO 74
<211> LENGTH: 11
<212> TYPE: PRT
<213> ORGANISM: Human

<400> SEQUENCE: 74

Gln Ser Tyr Asp Thr Ser Leu Arg Gly Pro Val
                 5                   10

<210> SEQ ID NO 75
<211> LENGTH: 14
<212> TYPE: PRT
<213> ORGANISM: Human

<400> SEQUENCE: 75

Thr Gly Ser Ser Ser Asn Ile Gly Thr Gly Tyr Asp Val His
                 5                   10

<210> SEQ ID NO 76
<211> LENGTH: 7
<212> TYPE: PRT
<213> ORGANISM: Human

<400> SEQUENCE: 76

-continued

Ala Tyr Thr Asn Arg Pro Ser
                5

<210> SEQ ID NO 77
<211> LENGTH: 11
<212> TYPE: PRT
<213> ORGANISM: Human

<400> SEQUENCE: 77

Gln Ser Phe Asp Asp Ser Leu Asn Gly Leu Val
                5                   10

<210> SEQ ID NO 78
<211> LENGTH: 14
<212> TYPE: PRT
<213> ORGANISM: Human

<400> SEQUENCE: 78

Thr Gly Ser His Ser Asn Phe Gly Ala Gly Thr Asp Val His
                5                   10

<210> SEQ ID NO 79
<211> LENGTH: 7
<212> TYPE: PRT
<213> ORGANISM: Human

<400> SEQUENCE: 79

Gly Asp Thr His Arg Pro Ser
                5

<210> SEQ ID NO 80
<211> LENGTH: 11
<212> TYPE: PRT
<213> ORGANISM: Human

<400> SEQUENCE: 80

Gln Ser Tyr Asp Tyr Gly Leu Arg Gly Trp Val
                5                   10

<210> SEQ ID NO 81
<211> LENGTH: 11
<212> TYPE: PRT
<213> ORGANISM: Human

<400> SEQUENCE: 81

Arg Ala Ser Gln Gly Ile Asp Asn Trp Leu Gly
                5                   10

<210> SEQ ID NO 82
<211> LENGTH: 7
<212> TYPE: PRT
<213> ORGANISM: Human

<400> SEQUENCE: 82

Asp Ala Ser Asn Leu Asp Thr
                5

<210> SEQ ID NO 83
<211> LENGTH: 9
<212> TYPE: PRT
<213> ORGANISM: Human

<400> SEQUENCE: 83

Gln Gln Ala Lys Ala Phe Pro Pro Thr
                5

<210> SEQ ID NO 84
<211> LENGTH: 2351
<212> TYPE: DNA
<213> ORGANISM: Human

<400> SEQUENCE: 84

| | | | | | | | |
|---|---|---|---|---|---|---|---|
| ggtaccgag | aaagaaccgg | ctcccgagtt | ctgggcattt | cgcccggctc | gaggtgcagg | | 59 |

| | | | | | | | | | | | | | | | | |
|---|---|---|---|---|---|---|---|---|---|---|---|---|---|---|---|---|
| atg | cag | agc | aag | gtg | ctg | ctg | gcc | gtc | gcc | ctg | tgg | ctc | tgc | gtg | gag | 107 |
| Met | Gln | Ser | Lys | Val | Leu | Leu | Ala | Val | Ala | Leu | Trp | Leu | Cys | Val | Glu | |
| | | | 5 | | | | | 10 | | | | | 15 | | | |

| | | | | | | | | | | | | | | | | |
|---|---|---|---|---|---|---|---|---|---|---|---|---|---|---|---|---|
| acc | cgg | gcc | gcc | tct | gtg | ggt | ttg | cct | agt | gtt | tct | ctt | gat | ctg | ccc | 155 |
| Thr | Arg | Ala | Ala | Ser | Val | Gly | Leu | Pro | Ser | Val | Ser | Leu | Asp | Leu | Pro | |
| | | | 20 | | | | | 25 | | | | | 30 | | | |

| | | | | | | | | | | | | | | | | |
|---|---|---|---|---|---|---|---|---|---|---|---|---|---|---|---|---|
| agg | ctc | agc | ata | caa | aaa | gac | ata | ctt | aca | att | aag | gct | aat | aca | act | 203 |
| Arg | Leu | Ser | Ile | Gln | Lys | Asp | Ile | Leu | Thr | Ile | Lys | Ala | Asn | Thr | Thr | |
| | | 35 | | | | | 40 | | | | | 45 | | | | |

| | | | | | | | | | | | | | | | | |
|---|---|---|---|---|---|---|---|---|---|---|---|---|---|---|---|---|
| ctt | caa | att | act | tgc | agg | gga | cag | agg | gac | ttg | gac | tgg | ctt | tgg | ccc | 251 |
| Leu | Gln | Ile | Thr | Cys | Arg | Gly | Gln | Arg | Asp | Leu | Asp | Trp | Leu | Trp | Pro | |
| | 50 | | | | | 55 | | | | | 60 | | | | | |

| | | | | | | | | | | | | | | | | |
|---|---|---|---|---|---|---|---|---|---|---|---|---|---|---|---|---|
| aat | aat | cag | agt | ggc | agt | gag | caa | agg | gtg | gag | gtg | act | gag | tgc | agc | 299 |
| Asn | Asn | Gln | Ser | Gly | Ser | Glu | Gln | Arg | Val | Glu | Val | Thr | Glu | Cys | Ser | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| gat | ggc | ctc | ttc | tgt | aag | aca | ctc | aca | att | cca | aaa | gtg | atc | gga | aat | 347 |
| Asp | Gly | Leu | Phe | Cys | Lys | Thr | Leu | Thr | Ile | Pro | Lys | Val | Ile | Gly | Asn | |
| | | | | 85 | | | | | 90 | | | | | 95 | | |

| | | | | | | | | | | | | | | | | |
|---|---|---|---|---|---|---|---|---|---|---|---|---|---|---|---|---|
| gac | act | gga | gcc | tac | aag | tgc | ttc | tac | cgg | gaa | act | gac | ttg | gcc | tcg | 395 |
| Asp | Thr | Gly | Ala | Tyr | Lys | Cys | Phe | Tyr | Arg | Glu | Thr | Asp | Leu | Ala | Ser | |
| | | | 100 | | | | | 105 | | | | | 110 | | | |

| | | | | | | | | | | | | | | | | |
|---|---|---|---|---|---|---|---|---|---|---|---|---|---|---|---|---|
| gtc | att | tat | gtc | tat | gtt | caa | gat | tac | aga | tct | cca | ttt | att | gct | tct | 443 |
| Val | Ile | Tyr | Val | Tyr | Val | Gln | Asp | Tyr | Arg | Ser | Pro | Phe | Ile | Ala | Ser | |
| | | 115 | | | | | 120 | | | | | 125 | | | | |

| | | | | | | | | | | | | | | | | |
|---|---|---|---|---|---|---|---|---|---|---|---|---|---|---|---|---|
| gtt | agt | gac | caa | cat | gga | gtc | gtg | tac | att | act | gag | aac | aaa | aac | aaa | 491 |
| Val | Ser | Asp | Gln | His | Gly | Val | Val | Tyr | Ile | Thr | Glu | Asn | Lys | Asn | Lys | |
| | 130 | | | | | 135 | | | | | 140 | | | | | |

| | | | | | | | | | | | | | | | | |
|---|---|---|---|---|---|---|---|---|---|---|---|---|---|---|---|---|
| act | gtg | gtg | att | cca | tgt | ctc | ggg | tcc | att | tca | aat | ctc | aac | gtg | tca | 539 |
| Thr | Val | Val | Ile | Pro | Cys | Leu | Gly | Ser | Ile | Ser | Asn | Leu | Asn | Val | Ser | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| ctt | tgt | gca | aga | tac | cca | gaa | aag | aga | ttt | gtt | cct | gat | ggt | aac | aga | 587 |
| Leu | Cys | Ala | Arg | Tyr | Pro | Glu | Lys | Arg | Phe | Val | Pro | Asp | Gly | Asn | Arg | |
| | | | | 165 | | | | | 170 | | | | | 175 | | |

| | | | | | | | | | | | | | | | | |
|---|---|---|---|---|---|---|---|---|---|---|---|---|---|---|---|---|
| att | tcc | tgg | gac | agc | aag | aag | ggc | ttt | act | att | ccc | agc | tac | atg | atc | 635 |
| Ile | Ser | Trp | Asp | Ser | Lys | Lys | Gly | Phe | Thr | Ile | Pro | Ser | Tyr | Met | Ile | |
| | | | 180 | | | | | 185 | | | | | 190 | | | |

| | | | | | | | | | | | | | | | | |
|---|---|---|---|---|---|---|---|---|---|---|---|---|---|---|---|---|
| agc | tat | gct | ggc | atg | gtc | ttc | tgt | gaa | gca | aaa | att | aat | gat | gaa | agt | 683 |
| Ser | Tyr | Ala | Gly | Met | Val | Phe | Cys | Glu | Ala | Lys | Ile | Asn | Asp | Glu | Ser | |
| | | 195 | | | | | 200 | | | | | 205 | | | | |

| | | | | | | | | | | | | | | | | |
|---|---|---|---|---|---|---|---|---|---|---|---|---|---|---|---|---|
| tac | cag | tct | att | atg | tac | ata | gtt | gtc | gtt | gta | ggg | tat | agg | att | tat | 731 |
| Tyr | Gln | Ser | Ile | Met | Tyr | Ile | Val | Val | Val | Gly | Tyr | Arg | Ile | Tyr | |
| | 210 | | | | | 215 | | | | | 220 | | | | | |

| | | | | | | | | | | | | | | | | |
|---|---|---|---|---|---|---|---|---|---|---|---|---|---|---|---|---|
| gat | gtg | gtt | ctg | agt | ccg | tct | cat | gga | att | gaa | cta | tct | gtt | gga | gaa | 779 |
| Asp | Val | Val | Leu | Ser | Pro | Ser | His | Gly | Ile | Glu | Leu | Ser | Val | Gly | Glu | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| aag | ctt | gtc | tta | aat | tgt | aca | gca | aga | act | gaa | cta | aat | gtg | ggg | att | 827 |
| Lys | Leu | Val | Leu | Asn | Cys | Thr | Ala | Arg | Thr | Glu | Leu | Asn | Val | Gly | Ile | |
| | | | | 245 | | | | | 250 | | | | | 255 | | |

| | | | | | | | | | | | | | | | | |
|---|---|---|---|---|---|---|---|---|---|---|---|---|---|---|---|---|
| gac | ttc | aac | tgg | gaa | tac | cct | tct | tcg | aag | cat | cag | cat | aag | aaa | ctt | 875 |
| Asp | Phe | Asn | Trp | Glu | Tyr | Pro | Ser | Ser | Lys | His | Gln | His | Lys | Lys | Leu | |
| | | | 260 | | | | | 265 | | | | | 270 | | | |

|   |   |
|---|---|
| gta aac cga gac cta aaa acc cag tct ggg agt gag atg aag aaa ttt<br>Val Asn Arg Asp Leu Lys Thr Gln Ser Gly Ser Glu Met Lys Lys Phe<br>275 280 285 | 923 |
| ttg agc acc tta act ata gat ggt gta acc cgg agt gac caa gga ttg<br>Leu Ser Thr Leu Thr Ile Asp Gly Val Thr Arg Ser Asp Gln Gly Leu<br>290 295 300 | 971 |
| tac acc tgt gca gca tcc agt ggg ctg atg acc aag aag aac agc aca<br>Tyr Thr Cys Ala Ala Ser Ser Gly Leu Met Thr Lys Lys Asn Ser Thr<br>305 310 315 320 | 1019 |
| ttt gtc agg gtc cat gaa aaa cct ttt gtt gct ttt gga agt ggc atg<br>Phe Val Arg Val His Glu Lys Pro Phe Val Ala Phe Gly Ser Gly Met<br>325 330 335 | 1067 |
| gaa tct ctg gtg gaa gcc acg gtg ggg gag cgt gtc aga atc cct gcg<br>Glu Ser Leu Val Glu Ala Thr Val Gly Glu Arg Val Arg Ile Pro Ala<br>340 345 350 | 1115 |
| aag tac ctt ggt tac cca ccc cca gaa ata aaa tgg tat aaa aat gga<br>Lys Tyr Leu Gly Tyr Pro Pro Pro Glu Ile Lys Trp Tyr Lys Asn Gly<br>355 360 365 | 1163 |
| ata ccc ctt gag tcc aat cac aca att aaa gcg ggg cat gta ctg acg<br>Ile Pro Leu Glu Ser Asn His Thr Ile Lys Ala Gly His Val Leu Thr<br>370 375 380 | 1211 |
| att atg gaa gtg agt gaa aga gac aca gga aat tac act gtc atc ctt<br>Ile Met Glu Val Ser Glu Arg Asp Thr Gly Asn Tyr Thr Val Ile Leu<br>385 390 395 400 | 1259 |
| acc aat ccc att tca aag gag aag cag agc cat gtg gtc tct ctg gtt<br>Thr Asn Pro Ile Ser Lys Glu Lys Gln Ser His Val Val Ser Leu Val<br>405 410 415 | 1307 |
| gtg tat gtc cca ccc cag att ggt gag aaa tct cta atc tct cct gtg<br>Val Tyr Val Pro Pro Gln Ile Gly Glu Lys Ser Leu Ile Ser Pro Val<br>420 425 430 | 1355 |
| gat tcc tac cag tac ggc acc act caa acg ctg aca tgt acg gtc tat<br>Asp Ser Tyr Gln Tyr Gly Thr Thr Gln Thr Leu Thr Cys Thr Val Tyr<br>435 440 445 | 1403 |
| gcc att cct ccc ccg cat cac atc cac tgg tat tgg cag ttg gag gaa<br>Ala Ile Pro Pro Pro His His Ile His Trp Tyr Trp Gln Leu Glu Glu<br>450 455 460 | 1451 |
| gag tgc gcc aac gag ccc agc cat gct gtc tca gtg aca aac cca tac<br>Glu Cys Ala Asn Glu Pro Ser His Ala Val Ser Val Thr Asn Pro Tyr<br>465 470 475 480 | 1499 |
| cct tgt gaa gaa tgg aga agt gtg gag gac ttc cag gga gga aat aaa<br>Pro Cys Glu Glu Trp Arg Ser Val Glu Asp Phe Gln Gly Gly Asn Lys<br>485 490 495 | 1547 |
| att gaa gtt aat aaa aat caa ttt gct cta att gaa gga aaa aac aaa<br>Ile Glu Val Asn Lys Asn Gln Phe Ala Leu Ile Glu Gly Lys Asn Lys<br>500 505 510 | 1595 |
| act gta agt acc ctt gtt atc caa gcg gca aat gtg tca gct ttg tac<br>Thr Val Ser Thr Leu Val Ile Gln Ala Ala Asn Val Ser Ala Leu Tyr<br>515 520 525 | 1643 |
| aaa tgt gaa gcg gtc aac aaa gtc ggg aga gga gag agg gtg atc tcc<br>Lys Cys Glu Ala Val Asn Lys Val Gly Arg Gly Glu Arg Val Ile Ser<br>530 535 540 | 1691 |
| ttc cac gtg acc agg ggt cct gaa att act ttg caa cct gac atg cag<br>Phe His Val Thr Arg Gly Pro Glu Ile Thr Leu Gln Pro Asp Met Gln<br>545 550 555 560 | 1739 |
| ccc act gag cag gag agc gtg tct ttg tgg tgc act gca gac aga tct<br>Pro Thr Glu Gln Glu Ser Val Ser Leu Trp Cys Thr Ala Asp Arg Ser<br>565 570 575 | 1787 |
| acg ttt gag aac ctc aca tgg tac aag ctt ggc cca cag cct ctg cca<br>Thr Phe Glu Asn Leu Thr Trp Tyr Lys Leu Gly Pro Gln Pro Leu Pro<br>580 585 590 | 1835 |

| | |
|---|---|
| atc cat gtg gga gag ttg ccc aca cct gtt tgc aag aac ttg gat act<br>Ile His Val Gly Glu Leu Pro Thr Pro Val Cys Lys Asn Leu Asp Thr<br>595              600                  605 | 1883 |
| ctt tgg aaa ttg aat gcc acc atg ttc tct aat agc aca aat gac att<br>Leu Trp Lys Leu Asn Ala Thr Met Phe Ser Asn Ser Thr Asn Asp Ile<br>610              615                  620 | 1931 |
| ttg atc atg gag ctt aag aat gca tcc ttg cag gac caa gga gac tat<br>Leu Ile Met Glu Leu Lys Asn Ala Ser Leu Gln Asp Gln Gly Asp Tyr<br>625              630              635              640 | 1979 |
| gtc tgc ctt gct caa gac agg aag acc aag aaa aga cat tgc gtg gtc<br>Val Cys Leu Ala Gln Asp Arg Lys Thr Lys Lys Arg His Cys Val Val<br>              645              650              655 | 2027 |
| agg cag ctc aca gtc cta gag cgt gtg gca ccc acg atc aca gga aac<br>Arg Gln Leu Thr Val Leu Glu Arg Val Ala Pro Thr Ile Thr Gly Asn<br>660              665                  670 | 2075 |
| ctg gaa aat cag acg aca agt att ggg gaa agc atc gaa gtc tca tgc<br>Leu Glu Asn Gln Thr Thr Ser Ile Gly Glu Ser Ile Glu Val Ser Cys<br>675              680              685 | 2123 |
| acg gca tct ggg aat ccc cct cca cag atc atg tgg tat aaa gat aat<br>Thr Ala Ser Gly Asn Pro Pro Pro Gln Ile Met Trp Phe Lys Asp Asn<br>690              695                  700 | 2171 |
| gag acc ctt gta gaa gac tca ggc att gta ttg aag gat ggg aac cgg<br>Glu Thr Leu Val Glu Asp Ser Gly Ile Val Leu Lys Asp Gly Asn Arg<br>705              710              715              720 | 2219 |
| aac ctc act atc cgc aga gtg agg aag gag gac gaa ggc ctc tac acc<br>Asn Leu Thr Ile Arg Arg Val Arg Lys Glu Asp Glu Gly Leu Tyr Thr<br>              725              730              735 | 2267 |
| tgc cag gca tgc agt gtt ctt ggc tgt gca aaa gtg gag gca ttt ttc<br>Cys Gln Ala Cys Ser Val Leu Gly Cys Ala Lys Val Glu Ala Phe Phe<br>740              745                  750 | 2315 |
| ata ata gaa ggt gcc cag gaa aag acg aac ttg gaa<br>Ile Ile Glu Gly Ala Gln Glu Lys Thr Asn Leu Glu<br>755              760 | 2351 |

<210> SEQ ID NO 85
<211> LENGTH: 764
<212> TYPE: PRT
<213> ORGANISM: Human

<400> SEQUENCE: 85

Met Gln Ser Lys Val Leu Leu Ala Val Ala Leu Trp Leu Cys Val Glu
                    5                      10                    15

Thr Arg Ala Ala Ser Val Gly Leu Pro Ser Val Ser Leu Asp Leu Pro
                    20                    25                    30

Arg Leu Ser Ile Gln Lys Asp Ile Leu Thr Ile Lys Ala Asn Thr Thr
                    35                    40                    45

Leu Gln Ile Thr Cys Arg Gly Gln Arg Asp Leu Asp Trp Leu Trp Pro
          50                    55                    60

Asn Asn Gln Ser Gly Ser Glu Gln Arg Val Glu Val Thr Glu Cys Ser
65                    70                    75                    80

Asp Gly Leu Phe Cys Lys Thr Leu Thr Ile Pro Lys Val Ile Gly Asn
                    85                    90                    95

Asp Thr Gly Ala Tyr Lys Cys Phe Tyr Arg Glu Thr Asp Leu Ala Ser
                  100                  105                110

Val Ile Tyr Val Tyr Val Gln Asp Tyr Arg Ser Pro Phe Ile Ala Ser
              115                  120                125

Val Ser Asp Gln His Gly Val Val Tyr Ile Thr Glu Asn Lys Asn Lys
        130                  135                140

-continued

```
Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
            180                 185                 190

Ser Tyr Ala Gly Met Val Phe Cys Glu Ala Lys Ile Asn Asp Glu Ser
        195                 200                 205

Tyr Gln Ser Ile Met Tyr Ile Val Val Val Gly Tyr Arg Ile Tyr
    210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
            260                 265                 270

Val Asn Arg Asp Leu Lys Thr Gln Ser Gly Ser Glu Met Lys Lys Phe
        275                 280                 285

Leu Ser Thr Leu Thr Ile Asp Gly Val Thr Arg Ser Asp Gln Gly Leu
290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Met
                325                 330                 335

Glu Ser Leu Val Glu Ala Thr Val Gly Glu Arg Val Arg Ile Pro Ala
            340                 345                 350

Lys Tyr Leu Gly Tyr Pro Pro Pro Glu Ile Lys Trp Tyr Lys Asn Gly
        355                 360                 365

Ile Pro Leu Glu Ser Asn His Thr Ile Lys Ala Gly His Val Leu Thr
370                 375                 380

Ile Met Glu Val Ser Glu Arg Asp Thr Gly Asn Tyr Thr Val Ile Leu
385                 390                 395                 400

Thr Asn Pro Ile Ser Lys Glu Lys Gln Ser His Val Val Ser Leu Val
                405                 410                 415

Val Tyr Val Pro Pro Gln Ile Gly Glu Lys Ser Leu Ile Ser Pro Val
            420                 425                 430

Asp Ser Tyr Gln Tyr Gly Thr Thr Gln Thr Leu Thr Cys Thr Val Tyr
        435                 440                 445

Ala Ile Pro Pro Pro His His Ile His Trp Tyr Trp Gln Leu Glu Glu
450                 455                 460

Glu Cys Ala Asn Glu Pro Ser His Ala Val Ser Val Thr Asn Pro Tyr
465                 470                 475                 480

Pro Cys Glu Glu Trp Arg Ser Val Glu Asp Phe Gln Gly Gly Asn Lys
                485                 490                 495

Ile Glu Val Asn Lys Asn Gln Phe Ala Leu Ile Glu Gly Lys Asn Lys
            500                 505                 510

Thr Val Ser Thr Leu Val Ile Gln Ala Ala Asn Val Ser Ala Leu Tyr
        515                 520                 525

Lys Cys Glu Ala Val Asn Lys Val Gly Arg Gly Glu Arg Val Ile Ser
530                 535                 540

Phe His Val Thr Arg Gly Pro Glu Ile Thr Leu Gln Pro Asp Met Gln
545                 550                 555                 560
```

-continued

```
Pro Thr Glu Gln Glu Ser Val Ser Leu Trp Cys Thr Ala Asp Arg Ser
                565                 570                 575
Thr Phe Glu Asn Leu Thr Trp Tyr Lys Leu Gly Pro Gln Pro Leu Pro
            580                 585                 590
Ile His Val Gly Glu Leu Pro Thr Pro Val Cys Lys Asn Leu Asp Thr
        595                 600                 605
Leu Trp Lys Leu Asn Ala Thr Met Phe Ser Asn Ser Thr Asn Asp Ile
    610                 615                 620
Leu Ile Met Glu Leu Lys Asn Ala Ser Leu Gln Asp Gln Gly Asp Tyr
625                 630                 635                 640
Val Cys Leu Ala Gln Asp Arg Lys Thr Lys Lys Arg His Cys Val Val
                645                 650                 655
Arg Gln Leu Thr Val Leu Glu Arg Val Ala Pro Thr Ile Thr Gly Asn
            660                 665                 670
Leu Glu Asn Gln Thr Thr Ser Ile Gly Glu Ser Ile Glu Val Ser Cys
        675                 680                 685
Thr Ala Ser Gly Asn Pro Pro Pro Gln Ile Met Trp Phe Lys Asp Asn
    690                 695                 700
Glu Thr Leu Val Glu Asp Ser Gly Ile Val Leu Lys Asp Gly Asn Arg
705                 710                 715                 720
Asn Leu Thr Ile Arg Arg Val Arg Lys Glu Asp Glu Gly Leu Tyr Thr
                725                 730                 735
Cys Gln Ala Cys Ser Val Leu Gly Cys Ala Lys Val Glu Ala Phe Phe
            740                 745                 750
Ile Ile Glu Gly Ala Gln Glu Lys Thr Asn Leu Glu
    755                 760

<210> SEQ ID NO 86
<211> LENGTH: 20
<212> TYPE: DNA
<213> ORGANISM: Artificial Sequence
<220> FEATURE:
<223> OTHER INFORMATION: amplification primer for VEGF

<400> SEQUENCE: 86
tcgggcctcc gaaaccatga                                          20

<210> SEQ ID NO 87
<211> LENGTH: 20
<212> TYPE: DNA
<213> ORGANISM: Artificial Sequence
<220> FEATURE:
<223> OTHER INFORMATION: amplification primer for VEGF

<400> SEQUENCE: 87
cctggtgaga gatctggttc                                          20

<210> SEQ ID NO 88
<211> LENGTH: 19
<212> TYPE: DNA
<213> ORGANISM: Artificial Sequence
<220> FEATURE:
<223> OTHER INFORMATION: amplification primer for Flt-1

<400> SEQUENCE: 88
tttgtgattt tggccttgc                                           19

<210> SEQ ID NO 89
<211> LENGTH: 21
<212> TYPE: DNA
```

```
<213> ORGANISM: Artificial Sequence
<220> FEATURE:
<223> OTHER INFORMATION: amplification primer for Flt-1

<400> SEQUENCE: 89
caggctcatg aacttgaaag c                                        21

<210> SEQ ID NO 90
<211> LENGTH: 20
<212> TYPE: DNA
<213> ORGANISM: Artificial Sequence
<220> FEATURE:
<223> OTHER INFORMATION: amplification primer for KDR

<400> SEQUENCE: 90
gtgaccaaca tggagtcgtg                                          20

<210> SEQ ID NO 91
<211> LENGTH: 20
<212> TYPE: DNA
<213> ORGANISM: Artificial Sequence
<220> FEATURE:
<223> OTHER INFORMATION: amplification primer for KDR

<400> SEQUENCE: 91
ccagagattc catgccactt                                          20

<210> SEQ ID NO 92
<211> LENGTH: 19
<212> TYPE: DNA
<213> ORGANISM: Artificial Sequence
<220> FEATURE:
<223> OTHER INFORMATION: amplification primer for KDR

<400> SEQUENCE: 92
tcatgtttga gaccttcaa                                           19

<210> SEQ ID NO 93
<211> LENGTH: 19
<212> TYPE: DNA
<213> ORGANISM: Artificial Sequence
<220> FEATURE:
<223> OTHER INFORMATION: amplification primer for KDR

<400> SEQUENCE: 93
gtctttgcgg atgtccacg                                           19
```